(12) United States Patent
Shendure et al.

(10) Patent No.: US 11,299,730 B2
(45) Date of Patent: Apr. 12, 2022

(54) MASSIVELY PARALLEL CONTIGUITY MAPPING

(71) Applicant: University of Washington Through Its Center for Commercialization, Seattle, WA (US)

(72) Inventors: Jay Ashok Shendure, Seattle, WA (US); Jerrod Joseph Schwartz, Seattle, WA (US); Andrew Colin Adey, Seattle, WA (US); Cho li Lee, Seattle, WA (US); Joseph Brian Hiatt, Seattle, WA (US); Jacob Otto Kitzman, Seattle, WA (US); Akash Kumar, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

(21) Appl. No.: 16/665,800

(22) Filed: Oct. 28, 2019

(65) Prior Publication Data

US 2020/0216839 A1    Jul. 9, 2020

Related U.S. Application Data

(63) Continuation of application No. 13/513,309, filed as application No. PCT/US2012/023679 on Feb. 2, 2012, now Pat. No. 10,457,936.

(60) Provisional application No. 61/473,083, filed on Apr. 7, 2011, provisional application No. 61/438,935, filed on Feb. 2, 2011.

(51) Int. Cl.
C12N 15/10 (2006.01)

(52) U.S. Cl.
CPC ........ *C12N 15/1093* (2013.01); *Y02P 20/582* (2015.11)

(58) Field of Classification Search
CPC .......................... C12N 15/1093; Y02P 20/582
See application file for complete search history.

(56) References Cited

U.S. PATENT DOCUMENTS

| | | |
|---|---|---|
| 5,130,238 A | 7/1992 | Malek |
| 5,185,243 A | 2/1993 | Ullman et al. |
| 5,214,587 A | 5/1993 | Green |
| 5,223,414 A | 6/1993 | Zarling et al. |
| 5,455,166 A | 10/1995 | Walker |
| 5,573,907 A | 11/1996 | Carrino et al. |
| 5,599,675 A | 2/1997 | Brenner |
| 5,641,658 A | 6/1997 | Adams et al. |
| 5,679,524 A | 10/1997 | Nikiforov et al. |
| 5,750,341 A | 5/1998 | Macevicz |
| 5,858,671 A | 1/1999 | Jones |
| 5,965,443 A | 10/1999 | Reznikoff et al. |
| 6,210,891 B1 | 4/2001 | Nyren et al. |
| 6,258,568 B1 | 7/2001 | Nyren |
| 6,274,320 B1 | 8/2001 | Rothberg et al. |
| 6,355,431 B1 | 3/2002 | Chee et al. |
| 6,437,109 B1 | 8/2002 | Reznikoff et al. |
| 6,593,113 B1 | 7/2003 | Tenkanen et al. |
| 6,777,187 B2 | 8/2004 | Makarov et al. |
| 6,828,098 B2 | 12/2004 | Langmore et al. |
| 6,846,658 B1 | 1/2005 | Vaisvila et al. |
| 7,001,792 B2 | 2/2006 | Sauer et al. |
| 7,057,026 B2 | 6/2006 | Barnes et al. |
| 7,115,400 B1 | 10/2006 | Adessi et al. |
| 7,138,267 B1 | 11/2006 | Jendrisak et al. |
| 7,211,414 B2 | 5/2007 | Hardin et al. |
| 7,244,559 B2 | 7/2007 | Rothberg et al. |
| 7,315,019 B2 | 1/2008 | Turner et al. |
| 7,329,492 B2 | 2/2008 | Hardin et al. |
| 7,399,590 B2 | 7/2008 | Piepenburg et al. |
| 7,405,281 B2 | 7/2008 | Xu et al. |
| 7,537,897 B2 | 5/2009 | Brenner et al. |
| 7,582,420 B2 | 9/2009 | Oliphant et al. |
| 7,595,883 B1 | 9/2009 | El Gamal et al. |
| 7,611,869 B2 | 11/2009 | Fan |
| 7,670,810 B2 | 3/2010 | Gunderson et al. |
| 7,741,463 B2 | 6/2010 | Gormley et al. |
| 8,003,354 B2 | 8/2011 | Shen et al. |
| 8,383,345 B2 | 2/2013 | Shendure et al. |
| 8,563,477 B2 | 10/2013 | Smith et al. |
| 8,829,171 B2 | 9/2014 | Steemers et al. |
| 9,074,251 B2 | 1/2015 | Steemers et al. |
| 9,644,198 B2 | 5/2017 | Walder et al. |
| 9,644,199 B2 | 5/2017 | Belyaev |

(Continued)

FOREIGN PATENT DOCUMENTS

| | | |
|---|---|---|
| CN | 102264914 A | 11/2011 |
| EP | 0320308 B1 | 11/1993 |

(Continued)

OTHER PUBLICATIONS

Goryshin et al. (Proceedings of the National Academy of Sciences 95.18 (1998): 10716-10721.) (Year: 1998).*
Steiniger et al. (Nucleic acids research 34.9 (2006): 2820-2832. (Year: 2006).*
Skoko et al. (Biochemistry 2004, 43, 13867-13874) (Year: 2004).*
Oh, Julia, et al. "A universal TagModule collection for parallel genetic analysis of microorganisms." Nucleic acids research 38.14 (2010): e146-e146. (Year: 2010).*
Fullwood, M.J., et al., "An oestrogen-receptor-α-bound human chromatin interactome," Nature 462:58-64, 2009.

(Continued)

*Primary Examiner* — Sahana S Kaup
(74) *Attorney, Agent, or Firm* — Christensen O'Connor Johnson Kindness PLLC

(57) ABSTRACT

Contiguity information is important to achieving high-quality de novo assembly of mammalian genomes and the haplotype-resolved resequencing of human genomes. The methods described herein pursue cost-effective, massively parallel capture of contiguity information at different scales.

18 Claims, 42 Drawing Sheets

Specification includes a Sequence Listing.

(56) References Cited

U.S. PATENT DOCUMENTS

| | | | |
|---|---|---|---|
| 2001/0046669 | A1 | 11/2001 | Mccombie et al. |
| 2002/0055100 | A1 | 5/2002 | Kawashima et al. |
| 2004/0002090 | A1 | 1/2004 | Mayer et al. |
| 2004/0096853 | A1 | 5/2004 | Mayer |
| 2004/0110191 | A1 | 6/2004 | Winkler et al. |
| 2004/0259229 | A1 | 12/2004 | Thevelein et al. |
| 2005/0191698 | A1 | 9/2005 | Chee et al. |
| 2006/0024681 | A1 | 2/2006 | Smith et al. |
| 2006/0040297 | A1 | 2/2006 | Leamon et al. |
| 2006/0216309 | A1 | 9/2006 | Holden |
| 2006/0236413 | A1 | 10/2006 | Ivics et al. |
| 2006/0257905 | A1 | 11/2006 | Freije |
| 2006/0292611 | A1 | 12/2006 | Berka et al. |
| 2007/0128610 | A1 | 6/2007 | Buzby |
| 2007/0128624 | A1 | 6/2007 | Gormley et al. |
| 2008/0009420 | A1 | 1/2008 | Schroth et al. |
| 2008/0108082 | A1 | 5/2008 | Rank et al. |
| 2008/0234136 | A1 | 9/2008 | Drmanac et al. |
| 2008/0242560 | A1 | 10/2008 | Gunderson et al. |
| 2009/0026082 | A1 | 1/2009 | Rothberg et al. |
| 2009/0032401 | A1 | 2/2009 | Ronaghi et al. |
| 2009/0047680 | A1 | 2/2009 | Lok |
| 2009/0127589 | A1 | 5/2009 | Rothberg et al. |
| 2009/0176234 | A1 | 7/2009 | Dramanae et al. |
| 2009/0298075 | A1 * | 12/2009 | Travers ............... C12Q 1/6869 435/6.12 |
| 2010/0009871 | A1 * | 1/2010 | Reed ................... B01J 19/0046 506/26 |
| 2010/0022403 | A1 | 1/2010 | Kurn et al. |
| 2010/0069263 | A1 | 3/2010 | Shendure et al. |
| 2010/0111768 | A1 | 5/2010 | Banerjee et al. |
| 2010/0120098 | A1 | 5/2010 | Grunenwald et al. |
| 2010/0137143 | A1 | 6/2010 | Rothberg et al. |
| 2010/0282617 | A1 | 11/2010 | Rothberg |
| 2011/0014657 | A1 | 1/2011 | Rigatti et al. |
| 2011/0059865 | A1 | 3/2011 | Smith et al. |
| 2011/0124518 | A1 | 5/2011 | Cantor |
| 2011/0311506 | A1 | 12/2011 | Craig et al. |
| 2012/0053063 | A1 | 3/2012 | Rigatti et al. |
| 2012/0129704 | A1 | 5/2012 | Gunderson et al. |
| 2012/0208724 | A1 | 5/2012 | Steemers et al. |
| 2012/0208705 | A1 | 8/2012 | Steemers et al. |
| 2012/0270305 | A1 | 10/2012 | Reed et al. |
| 2013/0017978 | A1 | 1/2013 | Kavanagh et al. |
| 2013/0203605 | A1 | 8/2013 | Shendure et al. |
| 2013/0338042 | A1 | 12/2013 | Shen et al. |
| 2014/0079923 | A1 | 3/2014 | George et al. |
| 2014/0093916 | A1 | 4/2014 | Belyaev |
| 2016/0138097 | A1 | 5/2016 | Yotani et al. |

FOREIGN PATENT DOCUMENTS

| | | | |
|---|---|---|---|
| EP | 0336731 | B1 | 5/1994 |
| EP | 0439182 | B1 | 4/1996 |
| EP | 2712931 | A1 | 4/2014 |
| EP | 2635679 | B1 | 4/2017 |
| EP | 2670894 | B1 | 11/2017 |
| JP | 2012-506704 | A | 3/2012 |
| JP | 2013150611 | A | 8/2013 |
| JP | 2013535986 | A | 9/2013 |
| WO | 1989/009835 | | 10/1989 |
| WO | 1989/010977 | | 11/1989 |
| WO | 1989/012696 | | 12/1989 |
| WO | 1990/001069 | | 2/1990 |
| WO | 1991/006678 | | 5/1991 |
| WO | 1995/023875 | | 9/1995 |
| WO | 1998/44151 | | 10/1998 |
| WO | 2004/018497 | | 3/2004 |
| WO | 2004/042078 | | 5/2004 |
| WO | 2005/065814 | | 7/2005 |
| WO | 2005/100585 | | 10/2005 |
| WO | 2006/047183 | A2 | 5/2006 |
| WO | 2007/098279 | | 8/2007 |
| WO | 2007/012744 | | 11/2007 |
| WO | 2008/087040 | A2 | 7/2008 |
| WO | 2010/002883 | A2 | 1/2010 |
| WO | 2010/048605 | | 4/2010 |
| WO | WO-2010048605 | A1 * | 4/2010 ............ C12N 15/66 |
| WO | 2011/106314 | A2 | 9/2011 |
| WO | 2012/025250 | | 3/2012 |
| WO | 2012/058096 | | 5/2012 |
| WO | 2012/061832 | | 5/2012 |
| WO | 2012/103545 | | 8/2012 |
| WO | 2012/106546 | | 8/2012 |
| WO | 2012/108864 | | 8/2012 |
| WO | 2012/027572 | A2 | 3/2013 |
| WO | 2013/177220 | | 11/2013 |
| WO | 2013/184796 | | 12/2013 |
| WO | 2014/108810 | | 7/2014 |
| WO | 2014/136930 | A1 | 9/2014 |
| WO | 2014/142850 | | 9/2014 |
| WO | 2015/031691 | A1 | 3/2015 |
| WO | 205/103339 | A1 | 7/2015 |

OTHER PUBLICATIONS

Gál, J., et al., "Directional cloning of native PCR products with preformed sticky ends (autosticky PCR)," Molecular & General Genetics 260(6):569-573, Jan. 1999.

Geiss, G.K., et al., "Direct multiplexed measurement of gene expression with color-coded probe pairs," Nat Biotechnol 26(3):317-325, 2008.

Gloor, G.B., "Gene targeting in Drosophila," Methods in Molecular Biology 260:97-114, 2004.

Gnerre, S., et al., "High-quality draft assemblies of mammalian genomes from massively parallel sequence data," Proc Natl Acad Sci USA (PNAS), PMID: 21187386, Dec. 27, 2010, 6 pages.

Goodman, A.L., et al., "Identifying genetic determinants needed to establish a human gut symbiont in its habit," Cell Host & Microbe 6:279-289, Sep. 2009.

Goryshin, I.Y., and W.S. Reznikoff, "Tn5 in Vitro Transposition," Journal of Biological Chemistry 273(13):7367-7374, Mar. 1998.

Grunenwald, H., et al., "Rapid, high-throughput library preparation for next-generation sequencing," Nature Methods, Application Notes, pp. iii-iv, Aug. 2010.

Grunenwald, H., et al., "Nextera PCR-Free DNA Library Preparation for Next-Generation Sequencing," Poster Presentation, AGBT, 2011.

GS FLX Titanium LVemPCR Kit (Lib-L) protocol, test kit, Roche Diagnostics GmbH, pp. 1-2, Version Aug. 2008, 2 pages.

Gu, H., et al., "Preparation of reduced representation bisulfite sequencing libraries for genome-scale DNA methylation profiling," Nat Protoc 6(4):468-481, 2011.

Haapa, S., et al., "An efficient and accurate integration of mini-Mu transposons in vitro: A general methodology for functional genetic analysis and molecular biology applications," Nuc Acids Res 27(13):2777-2784, 1999.

Handelsman, J., "Metagenomics: Application of Genomics to Uncultured Microorganisms," Microbiology and Molecular Biology Reviews 68(4):669-685, 2004.

Harris, R.A., et al., "Comparison of sequencing-based methods to profile DNA methylation and identification of monoallelic epigenetic modifications," Nat Biotechnol 28(10):1097-1105, 2010.

Healy, K., "Nanopore-based single-molecule DNA analysis," Nanomed 2(4):459-481, 2007.

Heredia, N.J., et al., "In vitro double transposition for DNA identification," Analytical Biochemistry 399:78-83, 2010.

Hiatt, J.B., et al., "Parallel, tag-directed assembly of locally derived short sequence reads," Nat Methods 7(2):119-122, 2010. PMCID: 2848820.

Http://www.epibio.com/nextera, Nextera™ DNA Sample Prep Kits, at least as early as Dec. 14, 2012.

Ichikawa, et al., "In vitro transposition of transposon Tn3," J Biol Chem 265(31):18829-18832, 1990.

International Search Report and Written Opinion for PCT/US12/23679, dated Aug. 24, 2012, 14 pages.

(56) References Cited

OTHER PUBLICATIONS

International Search Report and Written Opinion dated Aug. 24, 2012, issued in International Application No. PCT/US2012/23679, filed Feb. 2, 2012, 13 pages.
International Search Report and Written Opinion dated Jul. 11, 2016, issued in International Application No. PCT/US2015/056040, filed Oct. 16, 2015, 23 pages.
International Search Report and Written Opinion dated Jun. 23, 2015, issued in International Application No. PCT/US2014/070658, filed Dec. 6, 2014, 27 pages.
Ivics, Z., et al., "Targeted Sleeping Beauty Transposition in Human Cells," Molecular Therapy 15(6):1137-1144, Jun. 2007.
Jackson, A.A., and G.K. Fu, "Plasmid tagging for efficient large-scale sequence completion of entire clone inserts," BioTechniques 34:604 608, Mar. 2003.
Japanese Patent Office, Official Action for JP2013-552641, dated Jan. 12, 2016, 7 pages.
Johnson, D.S., et al., "Genome-wide mapping of in vivo protein-DNA interactions," Science 316(5830):1497-1502, 2007.
Johnson, R.C., et al., "DNA Sequences at the Ends of Transposon Tn5 Required for Transposition," Nature 304(5923):280-282, Jul. 1983.
Joos, B., et al., "Covalent attachment of hybridizable oligonucleotides to glass supports," Analytical Biochemistry 247:96-101, 1997.
Keith, J.M., et al., "Algorithms for Sequence Analysis via Mutagenesis," Bioinformatics 20(15):2401-2410, 2004 published online May 14, 2004.
Keith, J.M., et al., "Unlocking Hidden Genomic Sequence," Nucleic Acids Research 32(3):e35, 9 pages; published online Feb. 18, 2004.
Khandjian, E.W., "UV crosslinking of RNA to nylon membrane enhances hybridization signals," Mal Bio Rep 11:107-115, 1986.
Kidd, J.M., et al., "Mapping and sequencing of structural variation from eight human genomes," Nature 453(7191):56-64, 2008. (Author Manuscript provided, Pmcid: PMCID: 2424287, available in PMC Nov. 1, 2008, 9 pages.).
Kirby, C., et al., "Cryptic plasmids of *Mycobacterium avium*: Tn552 to the rescue," Molecular Microbiology 43(1):173-186, 2002.
Kirby, J.R., "In vivo mutagenesis using EZ-Tn5ATM," Methods in Enzymology 421:17-21, 2007.
Kitzman, J.O., et al., "Haplotype-resolved genome sequencing of a Gujarati Indian individual," Nat Biotechnol. 29(1):59-63, 2011; epub Dec. 19, 2010. (Author Manuscript provided, PMCID: PMC3116788, available in PMC Jul. 1, 2011, 5 pages.).
Kleckner, N., et al., "Tn10 and IS10 transposition and chromosome rearrangements: mechanism and regulation in vivo and in vitro," Curr Top Microbial Immunol 204:49-82, 1996.
Korlach, J., et al., "Selective aluminum passivation for targeted immobilization of single DNA polymerase molecules in zero-mode waveguide nanostructures," PNAS 105(4):1176-1181, 2008.
Kramer, P.R., "cDNA Library Construction from Single Cells," Current Protocols in Neuroscience 4.27.1-4.27.19, 2002.
Lage, J.M., et al., "Whole genome analysis of genetic alterations in small DNA samples using hyperbranched strand displacement amplification and array-CGH," Genome Research 13(2):294-307, 2003.
Lai, Z., et al., A shotgun optical map of the entire Plasmodium falciparum genome. Nat Genet. 23(3):309-313, 1999.
Lampe, D.J., et al., "A purified mariner transposase is sufficient to mediate transposition in vitro," EMBO J 15(19):5470-5479, 1996.
Lander, E.S., et al., "Initial sequencing and analysis of the human genome," Nature 409(6822):860-921, 2001.
Lehoux, D.E., et al., "Defined Oligonucleotide Tag Pools and PCR Screening in Signature-Tagged Mutagenesis of Essential Genes From Bacteria," Biotechniques 26(3):473-478; 480, Mar. 1999.
Levene, M.J., et al., "Zero-Mode Waveguides for Single-Molecule Analysis at high concentrations," Science 299:682-686, 2003.
Levy, S., et al., "The diploid genome sequence of an individual human," PLoS Biol 5(10):e254, 2007; published online Sep. 9, 2007. (Author Manuscript provided, PMCID: PMC1964779, 32 pages.).

Li, H., and R. Durbin, "Fast and accurate short read alignment with Burrows-Wheeler transform," Bioinformatics 25(14):1754-1760, 2009.
Li, R., et al., "De novo assembly of human genomes with massively parallel short read sequencing," Genome Res. 20(2):265-272, 2010. PMCID: PMC2813482.
Li, Y., et al., "Primase-based whole genome amplification," Nucleic Acids Res. 36(13):e79, 2008. PMCID: PMC2490742.
Li, Y., et al., "The DNA methylome of human peripheral blood mononuclear cells," PLoS Biol 8(11):e1000533, 2010.
Brouilette, S., et al., "A Simple and Novel Method for RNA-seq Library Preparation of Single Cell cDNA Analysis by Hyperactive Tn5 Transposase," Developmental Dynamics 241:1584-1590, 2012.
Adey, A., et al., "Rapid, low-input, low-bias construction of shotgun fragment libraries by high-density in vitro transposition," Genome Biology 11(12):R119, 2010.
Adey, A., and J. Shendure, "Ultra-low-input, tagmentation-based whole-genome bisulfite sequencing," Genome Research 22(6):1139-1143, Mar. 2012.
Amini, et al., "Haplotype-resolved whole-genome sequencing by contiguity-preserving transposition and combinatorial indexing," Nature Genetics 46(12):1343-1349, 2014.
Amini, et al., "Supplementary information for: Haplotype-resolved whole-genomes sequencing by contiguity-preserving transposition and combinatorial indexing," Nature Genetics 46(12):1-16, 2014.
Australia Patent Examination Report No. 1 for AU2012212148, dated Aug. 2, 2016, 4 pages.
Australian Examiner's Report dated May 24, 2017, issued in corresponding Australian Application No. 2012212148, filed Feb. 2, 2012, 3 pages.
Bains, et al., "A novel method for nucleic acid sequence determination," Journal of Theoretical Biology 135(3):303-307, 1988.
Ball, M.P., et al., "Targeted and genome-scale strategies reveal gene-body methylation signatures in human cells," Nat Biotechnol 27(4):361-368, 2009.
Bansal, V., et al., "HapCUT: An efficient and accurate algorithm for the haplotype assembly problem," Bioinformatics 24(16):1153-1159, 2008.
Batzoglou, S., et al., "ARACHNE: A whole-genome shotgun assembler," Genome Research 12:177-189, 2002.
Benetti, R., et al., "A mammalian microRNA cluster controls DNA methylation and telomere recombination via Rbl2-dependent regulation of DNA methyltransferases," Nat Struct Mol Biol 15(3):268-279, 2008.
Bentley, D.R., et al., "Accurate whole human genome sequencing using reversible terminator chemistry," Nature 456(7218):53-59, 2008. (Author Manuscript provided, PMCID: PMC2581791, available in PMC May 6, 2009, 20 pages.).
Bimber, et al., "Whole-genome characterization of human and simian immunodeficiency virus intrahost diversity by uptradeep pyrosequencing," Journal of Virology 84(22):12087-12092, 2010.
Bloch, et al., "Purification of *Escherichia coli* chromosomal segements without cloning," Biochemical and Biophysical Research Communications 223:104-111, 1996.
Boeke, et al., "Transcription and reverse transcription of retrotransposons," Annu Rev Microbial 43:403-434, 1989.
Branton, D., et al.,"The potential and challenges of nanopore sequencing," Nat Biotechnol 26(10):1146-1153, 2008. (Author Manuscript provided, PMCID: PMC2683588, available in PMC May 18, 2009, 8 pages.).
Braslavsky, I., et al., "Sequence information can be obtained from single DNA molecules," Proc Natl Acad Sci USA 100(7):3960-3964, 2003. (Author Manuscript provided, PMCID: PMC153030, available in PMC Mar. 21, 2003, 5 pages.).
Brown, et al., "Retroviral Integration: Structure of the Initial Covalent Product and Its Precursor, and a Role for the Viral IN Protein," PNAS 86:2525-2529, 1989.
Brownlie, et al., "The Caenorhabditis briggsae genome contains active CbmaT1 and Tcb1 transposons," Molecular Genetics and Genomics 273:92-101, 2005.
Canadian Examiner's Report dated Mar. 21, 2017, issued in corresponding Canadian Application No. 2,826,131, filed Feb. 2, 2012, 4 pages.

(56) References Cited

OTHER PUBLICATIONS

Caruccio, N., "Preparation of Next-Generation Sequencing Libraries Using Nextera (TM) Technology: Simultaneous DNA Fragmentation and Adaptor Tagging by in Vitro Transposition," Methods in Molecular Biology, Humana Press, Inc., US, vol. 733, Jan. 1, 2011, pp. 241-255.
Chernoff, A., et al., "Molecular analysis of the von Hippel-Lindau disease gene," Chapter 13, Methods in Molecular Medicine, vol. 42, "Renal Cancer: Methods and Protocols," edited by J.H. Mydio, Humana Press, Totowa, NJ, pp. 193-216, 2001.
Clark, S.J., et al., "High sensitivity mapping of methylated cytosines," Nucleic Acids Res 22(15):2990-2997, 1994.
Cockroft, et al., "A single-molecule nanpore device detects DNA polymerase activity with single-nucleotide resolution," J Am Chem Soc 130(3):818-820, 2008.
Cokus, S.J., et al., "Shotgun bisulphite sequencing of the *Arabidopsis* genome reveals DNA methylation patternina," Nature 452(7184):215-219, 2008.
Colegio, et al., "In vitro transposition system for efficient generation of random mutants of Campylobacter jejuni," Journal Bacterial 183(7):2384-2388, 2001.
Craig, N.L., "Transposon Tn7," Review in CurrTop Microbial Immunol 204:27-48, 1996.
Craig, N.L., "V(D)J recombination and transposition: Closer than expected," Science 271:1512, 1996, 1 page.
De Vries, J., et al., "PCR on cell lysates obtained from whole blood circumvents DNA isolation," Clinical Chemistry 47(9):1701-1702, 2001.
Deamer, et al., "Characterization of nucleic acids by nanopore analysis," Ace Chem Res 35(10):817-825, 2002.
Deamer, et al., "Nanopores and nucleic acids: Prospects for ultrarapid sequencing," Trends Biotechnol 18(4):147-151, 2000.
Dean, et al., "Comprehensive human genome amplification using multiple displacement amplification," PNAS 99(8):5261-5266, 2002.
Deng, J., et al., "Targeted bisulfite sequencing reveals changes in DNA methylation associated with nuclear reoroQrammina," Nat Biotechnol 27(4):353-360, 2009.
Down, T.A., et al., "A Bayesian deconvolution strategy for immunoprecipitation-based DNA methylome analysis," Nat Biotechnol 26(7):779-785, 2008.
Dressman, D., et al., "Transforming single DNA molecules into fluorescent magnetic particles for detection and enumeration of genetic variations," Proc Natl Acad Sci US A 100(15):8817-8822, 2003. (Author Manuscript provided, PMCID: PMC166396, available in PMC Jul. 11, 2003, 6 pages.).
Drmanac, R., et al., "Human genome sequencing using unchained base reads on self-assembling DNA nanoarrays," Science 327(5961):78-81, 2009.
Drmanac, et al., "Accurate sequencing by hybridization for DNA diagnostics and individual genomics," Nature Biotechnology 16(1):54-58, 1998.
Duan, Z., et al., "A three-dimensional model of the yeast genome," Nature 465(7296):363-367, 2010. (Author Manuscript provided, PMCID: PMC2874121, available in PMC Nov. 20, 2010, 12 pages.).
Duitama, J., et al., "Proceedings of the First ACM International Conference on Bioinformatics and Computational Biology," 2010, pp. 160-169.
Eid, J., et al., "Real-time DNA sequencing from single polymerase molecules," Science 323(5910):133-138, 2009.
European Patent Office, PCT Search Report and Written Opinion for PCT Application No. PCT/US2014/070658, dated Jun. 23, 2015.
European Patent Office, Communication pursuant to Article 94(c), dated Oct. 28, 2014, for Application No. 11802179.9.
European Patent Office, Examination Report for EP12741945.5, dated Oct. 26, 2015, 4 pages.
European Patent Office, Official Communication for EP12741945.5, dated Jul. 7, 2016, 2 pages.
Ewing, et al., "Base-calling of automated sequencer traces using phred. II. Error probabilities," Genome Research 8:186-194, 1998.
Extended European Search Report dated Sep. 22, 2014, issued in European Application No. EP12741945.5, filed Feb. 2, 2012, 7 pages.
Fan, H.D., et al., "Whole-genome molecular haplotyping of single cells," Nat Biotech 29(1):51-57, 2011.
Filee, J., et al., "Insertion Sequences Diversity in Archaea," Microbiology and Molecular Biology Reviews 71(1):121-157, Mar. 2007.
Fodor, et al., "Light-Directed, Spatially Addressable Parallel Chemical Synthesis," Science 251:767-773, 1991.
Fullwood, et al., "Chromatin Interaction Analysis Using Paired-End Tag Sequencing," Current Protocols in Molecular Biology 89, Chapter 21:Unit 21.15.1-25, 2010.
Shendure, J., et al., "Accurate multiplex polony sequencing of an evolved bacterial genome," Science 309(5741):1728-1732, 2005.
Shendure, J., "Sequence Tag Directed Subassembly of Short Sequencing Reads Into Long Sequencing Reads," U.S. Appl. No. 61/096,720, filed Sep. 12, 2008, 58 pages.
Shevchenko, Y., et al., "Systematic sequencing of cDNA clones using the transposon Tn5," Nucleic Acids Research 30(11):2469-2477, 2002.
Simon, S.A., et al., "Short-Read Sequencing Technologies for Transcriptional Analyses," Annual Review of Plant Biology 60:305-333, 2009.
Sipos, B., et al., "An Improved Protocol for Sequencing of Repetitive Genomic Regions and Structural Variations Using Mutagenesis and Next Generation Sequencing," PLoS One 7(8):e43359; published online Aug. 17, 2012, 9 pages.
Skoko, D., et al., "Micromechanical analysis of the binding of DNA-bending proteins HMGB1, NHP6A, and HU reveals their ability to form highly stable DNA-protein complexes," Biochemistry 43:13867-13874, 2004.
Smith, S.B., et al., "Direct Mechanical Measurements of the Elasticity of Single DNA Molecules by Using Magnetic Beads," Science 258(5085):1122-1126, 1992.
Soni, G.V., and A. Meller, "Progress toward Ultrafast DNA Sequencing Using Solid-State Nanopores," Clinical Chemistry 53(11):1996-2001, 2007.
Sorber, K., et al., "The Long March: A Sample Preparation Technique That Enhances Contig Length and Coverage by High-Throughput Short-Read Sequencing," PLoS ONE 2(10):e3495, 2008, 9 pages.
State Intellectual Property Office (China), First Office Action for CN201280012945.4, dated May 28, 2014, 15 pages.
State Intellectual Property Office, China PRC, Second Office Action for CN201280012945.4, dated Apr. 17, 2015, 18 pages.
State Intellectual Property Office, China PRC, Third Office Action for CN201280012945.4, dated Nov. 6, 2015, 21 pages.
Van Steensel, B., and J. Dekker, "Genomics tools for unraveling chromosome architecture," Nature Bitoechnology 28(10):1089-1095, Oct. 2010.
Steiniger, M., et al., Defining characteristics of Tn 5 Transposase non-specific DNA binding, Nucleic Acids Research 34(9):2820-2832, 2006.
Strahl, B.D., and C.D. Allis, "The Language of Covalent Histone Modifications," Nature 403(6765):41-45, Jan. 2000.
Supplementary European Search Report for Application EP12741945.5, dated Sep. 22, 2014, 7 pages.
Syed, F., et al. "Next-generation sequencing library preparation: Simultaneous fragmentation and tagging using in vitro transposition," Nature Methods, Application Notes, Nov. 2009, pp. i-ii.
Syed, F., et al., "Optimized library preparation method for next-generation sequencing," Nature Methods 6(10):1-11, Oct. 2009.
Taylor, D.M., et al., "Characterization of chemisorbed monolayers by surface potential measurements," Journal of Physics D: Applied Physics 24(8):1443-1450, 1991.
International Preliminary Report on Patentability for PCT/IB2014/000610, dated Jul. 14, 2015, 7 pages.
International Search Report and Written Opinion for PCT/US2011/059642, dated Apr. 10, 2012, 12 pages.
Office Action dated Mar. 27, 2012 for U.S. Appl. No. 12/559,124, filed Sep. 14, 2009, 13 pages.

(56) References Cited

OTHER PUBLICATIONS

Van Berkum, N.L., et al., "Hi-C: A Method to Study the Three-dimensional Architecture of Genomes," JoVE (Journal of Visualized Experiments) 39:e1869, 2010, 7 pages.
Vincent, M., et al., "Helicase-dependent isothermal DNA amplification," EMBO Reports 5(8):795-800, 2004.
Voordouw, G., et al., "Studies on ColE-1-plasmid DNA and Its Interactions With Histones; Sedimentation Velocity Studies of Monosidpserse Complexes Reconstituted With Calf-Thymus Histones," Nucleic Acids Research 4(5):1207-1223, 1977.
Walker, G.T., et al., "A Chemiluminescent DNA Probe Test Based on Strand Displacement Amplification," in "Molecular Methods for Virus Detection," Chap. 15, 1995, Academic Press Inc., pp. 329-349.
Walker, G.T., et al., "Strand displacement amplification—an isothermal, in vitro DNA amplification technique," Nucleic Acids Research 20(7):1691-1696, 1992.
Wang, H., et al., "Calling Cards Enable Multiplexed Identification of Genomic Targets of DNA-Binding Proteins," Genome Research 21(5):748-755, 2011.
Waterston, R.H., et al., "On the sequencing of the human genome," Proceedings of the National Academy of Sciences of the USA (PNAS) 99(6):3712-3716, 2002. (Author Manuscript provided, PMCID: PMC122589, published online Mar. 5, 2002, 5 pages.).
Waterston, R.H., et al., "More on the sequencing of the human genome," Proceedings of the National Academy of Sciences of the USA (PNAS) 100(6):3022-3024, 2003; author reply 5-6. PMCID:PMC152236. (Author Manuscript provided, PMCID: PMC152236, published online Mar. 11, 2003, 3 pages.).
Waterston, R.H., et al., "Initial sequencing and comparative analysis of the mouse genome," Nature 420(6915):520-562, 2002.
Wilson, A.C., et al., "New transposon delivery plasmids for insertional mutagenesis in Bacillus anthracis," Journal of Microbiological Methods 71:332-335, 2007.
Wold, B., and R.M. Myers, "Sequence Census Methods for Functional Genomics," Nature Methods 5(1):19-21 2008.
Wong, E., and C.-L. Wei, "ChIP'ing the Mammalian Genome: Technical Advances and Insights Into Functional Elements," Genome Medicine 1:89.1-89.10, 2009.
Xu, J., "Extracting Haplotypes from Diploid Organisms," Current Issues in Molecular Biology 8:113-122, Jul. 2006.
Zeevi, V., et al., "Increasing cloning possibilities using artificial zinc finger nucleases," Proceedings of the National Academy of Sciences USA (PNAS) 105(35):12785-12790, Sep. 2008.
Zeng, Y., et al., "High-Performance single cell genetic analysis using microfluidic emulsion generator arrays," Analytical Chemistry 82(8):3183-3190, 2010. (Author Manuscript provided, PMCID: PMC2859697, available in PMC Apr. 15, 2011, 8 pages.).
Zerbino, D.R., and E. Birney, "Velvet: Algorithms for De Novo Short Read Assembly Using de Bruijn Graphs," Genome Research 18:821-829, 2008.
Zhang, Z., and M.H. Saier, Jr., "A Novel Mechanism of Transposon-Mediated Gene Activation," PLoS Genetics 5(10):e1000689, 2009, 9 pages.
Zhou, M., et al., "Molecular genetic analysis of transposase—End DNA sequence recognition: Cooperativity of three adjacent base-pairs in specific interaction with a mutant Tn5 transposase," Journal of Molecular Biology 276:913-925, 1998.
Zhou, S., et al., "Validation of rice genome sequence by optical mapping," BMC Genomics 8(1):278, Aug. 2007, 18 pages.
Zhou, S., et al., "A Single Molecule Scaffold for the Maize Genome," PLoS Genetics 5(11):e1000711, 2009, 14 pages.
Zilberman, D., and S. Henikoff, "Genome-wide analysis of DNA methylation patterns," Development 134(22):3959-3965, 2007.
Li, J., et al., "DNA molecules and configurations in a solid-state nanopore microscope," Nature Materials 2(9):611-615, 2003.
Lieberman-Aiden, E., et al., "Comprehensive mapping of long-range interactions reveals folding principles of the human genome," Science 326(5950):289-293, 2009. (Author Manuscript provided, PMCID: PMC2858594, available in PMC Apr. 22, 2010, 11 pages.).
Lim, A., et al., "Shotgun optical maps of the whole *Escherichia coli* 0157:H7 genome," Genome Research 11(9):1584-1593, 2001. (Author Manuscript provided, PMCID: PMC311123, 10 pages.).
Lin, J., et al., "Whole-genome shotgun optical mapping of Deinococcus radiodurans," Science 285(5433):1558-1562, 1999.
Lister, R., et al., "Human DNA methylomes at base resolution show widespread epigenomic differences," Nature 462(7271):315-322, 2009.
Lizardi, P.M., et al., "Mutation detection and single-molecule counting using isothermal rolling-circle amplification," Nature Genetics 19:225-232, 1998.
Lundquist, P.M., et al., "Parallel confocal detection of single molecules in real time," Optics Letters33(9):1026-1028, 2008.
Mahillon, J., and M. Chandler, "Insertion Sequences," Microbiology and Molecular Biology Reviews 62(3):725-774, Sep. 1998.
Mardis, E.R., "Next-Generation DNA Sequencing Methods," Annual Review of Genomics and Human Genetics 9:387-402, 2008.
Mardis, E.R., "The impact of next-generation sequencing technology on genetics," Trends in Genetics 24:133-141, 2008.
Margulies, M., et al., "Genome sequencing in microfabricated high-density picolitre reactors," Nature 437(7057):376-380, 2005. (Author Manuscript provided, PMCID: PMC1464427, available in PMC Sep. 15, 2006, 14 pages.).
Marine, R., et al., "Evaluation of a transposase protocol for rapid generation of shotgun high-throughput sequencing libraries from nanogram quantities of DNA," Applied and Environmental Microbiology 77(22):8071-8079, Nov. 2011.
Mazutis, L., et al., "Droplet-based microfluidic systems for high-throughput single DNA molecule isothermal amplification and analysis," Analytical Chemistry 81(12):4813-4821, 2009.
McCloskey, M.M., et al., "Encoding PCR Products with Batch-Stamps and Barcodes," Biochem Genet 45:761-767, 2007.
Meissner, A., et al., "Reduced representation bisulfite sequencing for comparative high-resolution DNA methylation analysis," Nucleic Acids Research 33(18):5868-5877, 2005.
Miner, B.E., et al., "Molecular barcodes detect redundancy and contamination in hairpin-bisulfite PCR," Nucleic Acids Research 32(17):e135, Sep. 2004, 4 pages.
Mitra, R D., et al., "Fluorescent in situ sequencing on polymerase colonies," Analytical Biochemistry 320(1):55-65, 2003.
Mizuuchi, K., "In vitro transposition of bacteriophase mu: A biochemical approach to a novel replication reaction," Cell 35:785-794, 1983.
Mizuuchi, K., "Transpositional recombination: Mechanistic insights from studies of mu and other elements," Annual Reviews Biochemistry 61:1011-1051, 1992.
Mortazavi, A., et al., "Mapping and quantifying mammalian transcriptomes by RNA-Seq," Nat Methods 5(7):621-628, 2008.
Ng, S.B., et al., "Targeted capture and massively parallel sequencing of 12 human exomes," Nature 461(7261):272-276, 2009. (Author Manuscript provided, PMCID: PMC2844771, available in PMC Mar. 23, 2010, 5 pages.).
Nijman, I.J., et al., "Mutation discovery by targeted genomic enrichment of multiplexed barcoded samples," Nature Methods 7(11):913-915, 2010.
Oh, J., et al., "A universal TagModule collection for parallel genetic analysis of microorganisms," Nucleic Acids Research 38(14):146, 2010, 14 pages.
Oh, J., "A Robust Platform for High-Throughput Genomics in Microorganisms," Doctoral Dissertation, Stanford University, Mar. 2010, pp. i, ii and 10-30.
Ohtsubo, E., and Y. Sekine, "Bacterial insertion sequences," Current Topics in Microbiology and Immunology 204:1-26, 1996.
Old, R., et al., "Recognition Sequence of Restriction Endonuclease III From Hemophilus influenzae," Journal of Molecular Biology 92(2):331-339, Feb. 1975.
Ooka, T., et al., "Inference of the impact of insertion sequence (IS) elements on bacterial genome diversification through analysis of small-size structural polymorphisms in *Escherichia coli* 0157 genomes," Genome Research 19:1809-1816, 2009.
Oroskar, A.A., et al., "Detection of immobilized amplicons by ELISA-like techniques," Clinical Chemistry 42(9):1547-1555, 1996.

(56) References Cited

OTHER PUBLICATIONS

Parkinson, N.J., et al., "Preparation of High-Quality Next-Generation Sequencing Libraries From Picogram Quantities of Target DNA," Genome Research 22(1):125-133, Jan. 2012.
Paul, P., et al., "Single-molecule dilution and multiple displacement amplification for molecular haplotyping," BioTechniques 38(4):553-559, Apr. 2005.
Peck, D., et al., "A Method for High-Throughput Gene Expression Signature Analysis," Genome Biology 7(7):R61, 2006, 6 pages.
Plasterk, R.H.A., "The Tc1/mariner transposon family," Current Topics in Microbiology and Immunology 204:125-143, 1996.
Pobigaylo, N., et al., "Construction of a large signature-tagged Mini-Tn 5 transposon library and its application to mutagenesis of Sinorhizobium meliloti," Applied and Environmental Microbiology 72(6):4329-4337, Jun. 2006.
Ramanathan, A., et al., "An integrative approach for the optical sequencing of single DNA molecules," Analytical Biochemistry 330(2):227-241, 2004.
Raymond, C.K., et al., "Targeted, Haplotype-Resolved Resequencing of Long Segments of the Human Genome," Genomics 86:759-766, 2005.
Reinhardt, J.A., et al., "De nova assembly using low-coverage short read sequence data from the rice pathogen Pseudomonas syringae pv. oryzae," Genome Research 19(2):294-305, Feb. 2009.
Riehn, R., et al., "Restriction mapping in nanofluidic devices," Proceedings of the National Academy of Sciences of the United States of America (PNAS) 102(29):10012-10016, 2009.
Ritz, A., et al., "Structural variation analysis with strobe reads," Bioinformatics 26(10):1291-1298, 2010.
Roche Applied Science/Roche Diagnostics GmbH, "GS FLX Titanium LV/SV emPCR Kit (Lib-L) protocol," Aug. 2008, 2 pages.
Rode, C.K., et al., "New Tools for Integrated Genetic and Physical Analyses of the *Escherichia coli* Chromosome," Gene 166(1):1-9, Dec. 1995.
Ronaghi, M., "Pyrosequencing sheds light on DNA sequencing," Genome Research 11(1):3-11, 2001.
Ronaghi, M., et al., "A Sequencing Method Based on Real-Time Phyrophosphate," Science 281(5375):363-365, 1998.
Ronaghi, M., et al., "Real-time DNA sequencing using detection of pyrophosphate release," Analytical Biochemistry 242:242-289, 1996.
Savilahti, H., et al., "The Phage Mu transpososome core: DNA requirements for assembly and function," EMBO Journal 14:4893-4903, 1995.
Schatz, M.C., et al., "Assembly of Large Genomes Using Second-Generation Sequencing," Genome Research 20(9):1165-1173, May 2010.
Schwartz, D.C., et al., "Ordered restriction maps of *Saccharomyces cerevisiae* chromosomes constructed by optical mapping," Science 262(5130):110-114, 1993.
Schwartz, J.J., et al., "Capturing native long-range contiguity by in situ library construction and optical sequencing," Proceedings of the National Academy of Sciences of the USA (PNAS) 109(46):18749-18754, 2012.
Seong, G.H., et al., "Measurement of Enzyme Kinetics Using a Continuous-Flow Microfluidic System," Analytical Chemistry 75(13):3161-3167, Jul. 2003.
Shendure, J., and H. Ji, "Next-generation DNA sequencing," Nature Biotechnology 26(10):1135-1145, 2008.
Shendure, J., et al., "Advanced sequencing technologies: Methods and goals," Nature Reviews Genetics 5(5):335-344, 2004.
Salmen, F., et al., "Barcoded Solid-Phase RNA Capture for Spatial Transcriptomics Profiling in Mammalian Tissue Sections," Nature Protocols 13(11):2501-2534, Nov. 2018.

\* cited by examiner

Lorem Ipsum

FIG. 18A FIG. 18B

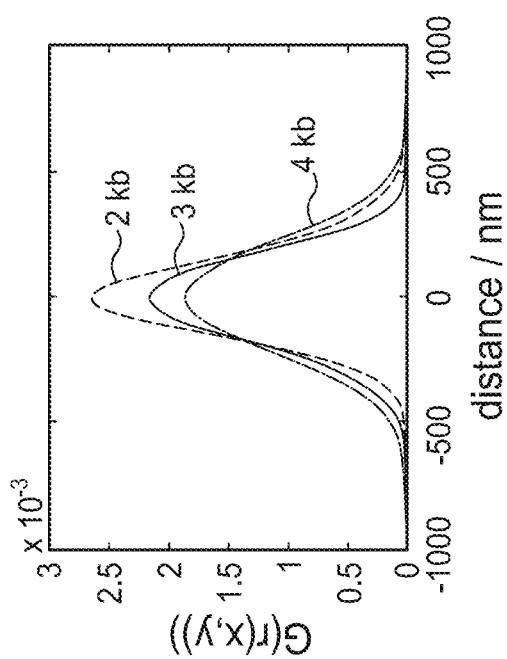
FIG. 39A
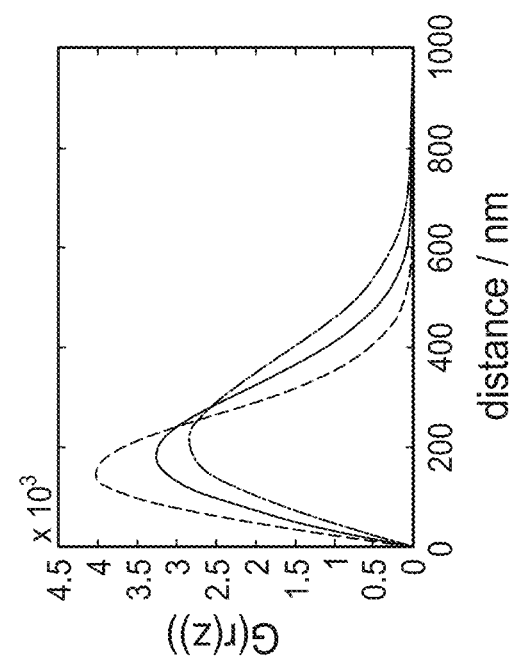
FIG. 39B
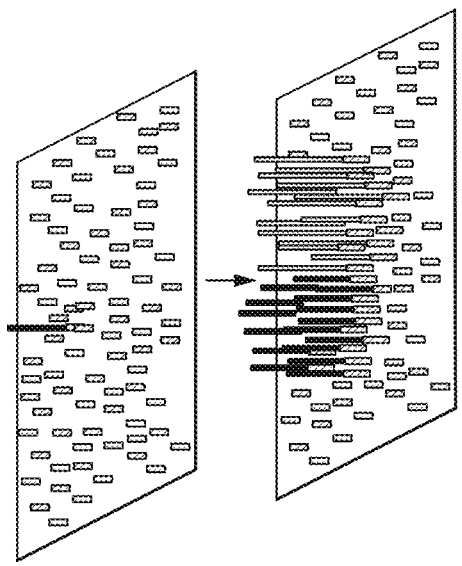
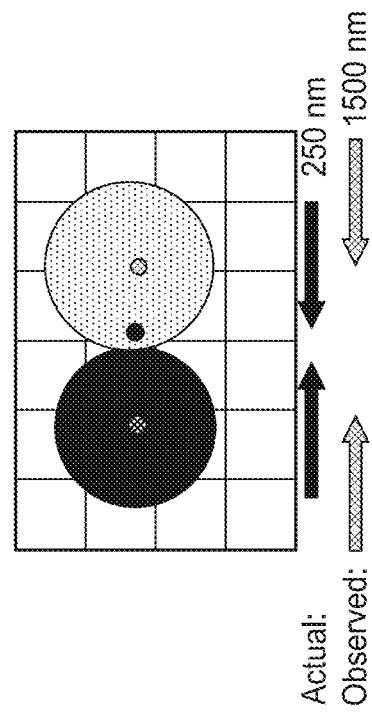
FIG. 39C

MASSIVELY PARALLEL CONTIGUITY MAPPING

CROSS-REFERENCES TO RELATED APPLICATIONS

This application is a continuation of U.S. application Ser. No. 13/513,309, filed Oct. 31, 2012 (U.S. Pat. No. 10,457, 936), which is a U.S. National Phase of International Patent Application No. PCT/US2012/023679, filed Feb. 2, 2012, which claims the benefit of U.S. Provisional Patent Application No. 61/438,935, filed Feb. 2, 2011, and U.S. Provisional Patent Application No. 61/473,083, filed Apr. 7, 2011, each of which is incorporated herein by reference in its entirety.

STATEMENT OF GOVERNMENT SUPPORT

This invention was made with government support under Grant Numbers U54 AI057141 and RO1 HG006283, awarded by National Institutes of Health. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 70419_Seq_Final_2019-10-25.txt. The text file is 3 KB; was created on Oct. 25, 2019; and is being submitted via EFS-Web with the filing of the specification.

BACKGROUND

Over the last several years, massively parallel sequencing platforms have reduced the cost-per-base of DNA sequencing by several orders of magnitude (Shendure & Ji 2008). Of the "next-generation" technologies that are commercially available, nearly all rely on iterative cycles of biochemistry and imaging of dense arrays of sequencing features to generate relatively short reads, i.e. "cyclic-array" methods (Shendure et al. 2005; Margulies et al. 2005; Drmanac et al. 2009; Braslaysky et al. 2003; Bentley et al. 2008). The broad dissemination of these platforms represents the culmination of decades of effort to develop practical alternatives to electrophoretic sequencing (Shendure et al. 2004).

In the context of this success, many developing technologies have the potential to improve the technical capability of what is already feasible today. Such improvements may be accomplished by further development of cyclic array methods, or through the maturation of other promising strategies such as nanopore sequencing (Branton et al. 2008), real-time observation of DNA synthesis (Eid et al. 2009) and sequencing by electron microscopy. Massively parallel sequencing platforms have also given rise to several types of sequencing applications, including resequencing, de novo assembly, exome sequencing (Ng et al. 2009), RNA-Seq (Mortazavi et al. 2008), ChIP-Seq (Johnson et al. 2007), and genome-wide chromatin interaction mapping (Lieberman-Aiden et al. 2009; Duan et al. 2010).

Although DNA sequencing technology platforms have improved at a rapid pace, the cost of DNA sequencing remains prohibitive for some goals. Therefore, it is desired to produce methods related to DNA sequencing technology that not only improve the application of existing and developing technology, but also reduce the cost.

SUMMARY

Short-read sequencing is limited with respect to resequencing of segmental duplications and structurally complex regions of the genome, the resolution of haplotype information, and the de novo assembly of mammalian-sized genomes. Moreover, further reductions in the cost-per-base of sequencing will do little to address these limitations. Even as new approaches to DNA sequencing mature and surpass current technology, technologies may continue to be limited in terms of the contiguity information that they generate. Therefore, low-cost methods for obtaining contiguity information at different scales are provided herein.

In some embodiments, methods for capturing contiguity information comprising are provided herein. Such methods may include treating a target DNA sequence with a transposase resulting in one or more fragmentation or insertion events; adding or inserting one or more recognition sequences to the target DNA sequence (i) during the transposase treatment of (ii) during a subsequent amplification; sequencing the treated DNA; and capturing contiguity information by identifying target DNA sequences or recognition sequences having a shared property.

In one embodiment, the one or more fragmentation or insertion events results in generation of a library of target nucleic acid molecules derived from the target DNA. In such methods, the one or more recognition sequences are one or more barcodes that are symmetrically tagged to sequences adjacent to each fragmentation or insertion event and the shared property of the one or more barcodes is an identical or complimentary barcode sequence.

In another embodiment, the target DNA sequence comprises a set of target DNA fragments. Such an embodiment may further include compartmentalizing the target DNA fragments with emulsions or dilutions, generating two or more compartments of target DNA fragments prior to or after treating with the transposase. In this embodiment, the one or more recognition sequences are one or more compartment-specific barcodes, each of which corresponds to the one or more compartments generated in the compartmentalizing step and the shared property of the one or more primer sequences is an identical compartment-specific barcode.

In another embodiment, the one or more recognition sequences is one or more adaptor sequences that modify the ends of the target DNA sequence or insert within the target DNA sequence. In such an embodiment, the one or more adaptor sequences may be complementary to one or more surface-bound primers. In some aspects, the transposase is bound to a nucleic acid that is complementary to a second surface-bound primer. Further, such a method may include hybridizing the one or more adaptor sequences to the one or more surface bound primers. In some embodiments, the shared property is a constrained physical location, which may be indicated by an x,y coordinate on a flowcell, and the transposase is bound to a surface-bound recognition sequence to form a surface-bound transposase complex. In some embodiments, treating the target DNA sequence comprises exposing a plurality of surface-bound transposase complexes to the target DNA sequence.

In some embodiments, methods of bisulfite sequencing are provided. Such methods may include performing in vitro transposition into target DNA molecules with transposase complexes, each transposase complex comprising a double stranded DNA transposase recognition sequence and a single stranded DNA adaptor overhang having methylated cytosine (C) residues; subjecting transposed target DNA molecules to bisulfite treatment; performing nucleic acid amplification; and sequencing the resulting nucleic acid library.

In other embodiments, methods for inferring chromosome conformation are provided. Such methods may include cross-linking DNA within cells; isolating cross-linked DNA from cells; fragmenting the cross-linked DNA; end-modifying fragmented, cross-linked DNA molecules with an adaptor that is complementary to or that corresponds to a first surface-bound primer; e) hybridizing ends of the fragmented, end-modified target DNA molecules to the first surface-bound primer; f) performing transposition with non-surface-bound transposase complexes, each non-surface-bound transposase complex comprising a DNA transposase and one or more sequences corresponding to a second surface-bound primer; g) performing cluster amplification to produce clusters of clonally derived nucleic acids; h) sequencing clusters of clonally derived nucleic acids; and i) determining physical interactions between chromosomal positions by paring neighboring clusters together.

BRIEF DESCRIPTION OF THE DRAWINGS

FIGS. 39A-39C show plots of $G_{surf}$ for the x, y and z components of the end-to-end vector $\vec{r}$ are shown for DNA tethered to a surface (39A and 39B). (39C) shows a graphic illustration of what may be happening during cluster formation. When two seed templates are localized in close proximity on the surface, as cluster amplification proceeds there is a local depletion of available surface primers. This forces the clusters to grow away from each other. During basecalling, the cluster centers are called at a x-y positions that do not coincide with the original seeding templates.

DETAILED DESCRIPTION

Figure 1:
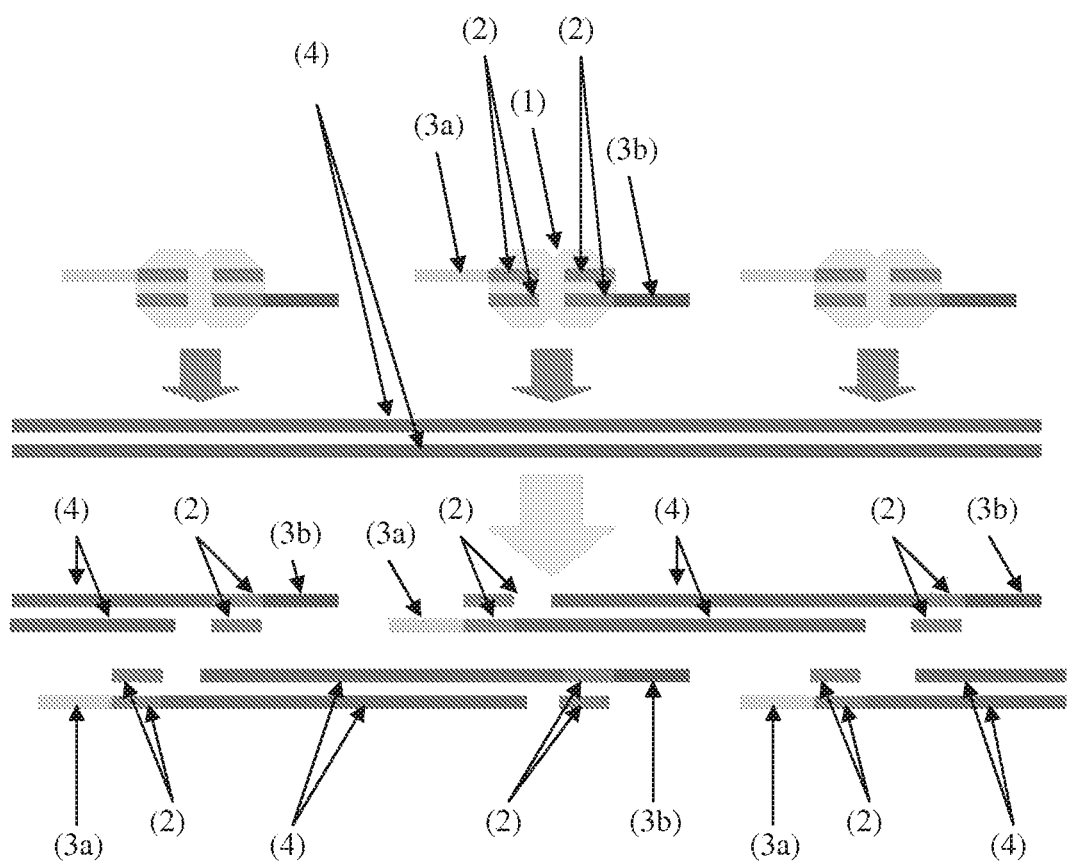
FIG. 1 illustrates high density, random, in vitro transposition of discontinuous oligonucleotides enables the high efficiency conversion of genomic DNA into adaptor-flanked, shotgun fragments. Light grey area (1)=transposase; dark grey bars (2)=mosaic ends (ME); yellow & red (3a, 3b)=asymmetrical 5' overhangs; blue (4)=genomic DNA.

Methods of capturing contiguity information are provided herein. The contiguity information and the embodiments for receiving such information may be used with any suitable traditional or second generation DNA sequencing technology to improve the efficacy and accuracy of the technology and related uses and applications; and to increase its cost effectiveness. Suitable DNA sequencing technologies that may be used in accordance with the methods described herein may include, but are not limited to, "cyclic-array" methods (e.g., 454 pyrosequencing, Illumina Genome Analyzer, AB SOLiD, and HeliScope), nanopore sequencing methods, real-time observation of DNA synthesis, sequencing by electron microscopy, dideoxy termination and electrophoresis, microelectrophoretic methods, sequencing by hybridization, and mass spectroscopy methods.

Many of these sequencing methods include several common procedural concepts to sequence a long strand of DNA (or "target DNA sequence"). First, the target DNA sequence is broken up into numerous small sequence fragments (or "DNA fragments"). This may be accomplished by treating the target DNA with a transposase. In some examples. the numerous DNA fragments may be considered to be a DNA fragment library (or "shotgun library"). Next, the DNA fragments may be amplified or cloned, resulting in the generation of clonal copies or clusters. The clonal copies or clusters are then sequenced by a sequencing platform, such as those described above. After sequencing, the sequenced DNA fragments may be reassembled to reconstruct the original sequence, or mapped to a reference genome to identify sequence variations.

Capturing Contiguity Information

As discussed above, when a target DNA sequence is treated with transposase, the target DNA may be broken up into two or more DNA fragments that, prior to the transposase treatment (i.e., prior to fragmentation), were connected via one or more spatial relationships. In one embodiment, the spatial relationship is an adjacent relationship, wherein the DNA fragments were directly adjacent to one another (i.e., the end of one DNA fragment was connected to the end of a second DNA fragment). In another embodiment, the spatial relationship may be a compartmental relationship, wherein the target DNA comprises two or more sequence segments that are categorized as compartments. In such an embodiment, DNA fragments prior to fragmentation by transposase may have been within the same segment of the target DNA, but not necessarily adjacent to one another. In another embodiment, the spatial relationship is a distance relationship wherein the DNA fragments were non-contiguous and non-adjacent prior to fragmentation, but are related by a particular distance or sequence length between each other. These spatial relationships may be determined by capturing contiguity information using methods described herein.

Contiguity information refers to a spatial relationship between two or more DNA fragments based on shared information. The shared aspect of the information can be with respect to adjacent, compartmental and distance spatial relationships. Information regarding these relationships in turn facilitates hierarchical assembly or mapping of sequence reads derived from the DNA fragments. This contiguity information improves the efficiency and accuracy of such assembly or mapping because traditional assembly or mapping methods used in association with conventional shotgun sequencing do not take into account the relative genomic origins or coordinates of the individual sequence reads as they relate to the spatial relationship between the two or more DNA fragments from which the individual sequence reads were derived. Therefore, according to the embodiments described herein, methods of capturing contiguity information may be accomplished by short range contiguity methods to determine adjacent spatial relationships, mid-range contiguity methods to determine compartmental spatial relationships, or long range contiguity methods to determine distance spatial relationships. These methods facilitate the accuracy and quality of DNA sequence assembly or mapping, and may be used with any sequencing method, such as those described above.

According to the embodiments described herein, the methods for capturing contiguity information may include treating a target DNA sequence with a transposase resulting in one or more fragmentation or inserting events. In some embodiments, this step results in the generation of a library of shotgun nucleic acid molecules derived from the target DNA sequence. In an alternative embodiment, the fragmentation or insertion even may be accomplished by a Y adaptor approach as described below. The one or more transposase molecules may be soluble free transposase or may be associated with a surface-bound recognition sequence.

The target DNA, after treating with the transposase may comprise two or more DNA fragments or a plurality of DNA fragments (also referred to as "the fragmented target DNA") or may comprise an insertion sequence ("the insertion target DNA").

In some embodiments, the methods for capturing contiguity information may include a step of amplifying the DNA or shotgun library to generate clonal copies or clusters of reads. The amplification step may include, but is not limited to any suitable amplification method such as polony, emulsion PCR, and bridge PCR.

In some embodiments, after treatment with transposase or after a subsequent amplification, one or more recognition sequences may be added to or inserted into the fragmented or insertion target DNA. The one or more recognition sequences may include, but are not limited to, a barcode, a primer or an adaptor DNA sequence at the site of the fragmentation or insertion that tags the DNA fragment as unique with respect to the adjacent, compartmental or distance spatial relationship.

After being tagged, the shotgun nucleic acid molecules may be sequenced using a sequencing platform described above contiguity information is captured by identifying recognition sequences that have a shared property. In some embodiments, the shared property is an identical or complementary barcode sequence. For example, read sequences of adjacent origin may be identified via shared barcode sequences; or reads may be defined by compartments based on shared compartment-specific barcodes derived from the same target DNA segment. In other embodiments, the shared property is a shared or constrained physical location, which may be indicated by one or more x,y coordinates on a flowcell. A "constrained" physical location may refer to a close, identical, or nearly identical physical location or to a set of two or more physical locations whose relative physical coordinates are correlated with the relative sequence coordinates on the target DNA sequence from which the DNA fragments were derived. For example, in methods relating to long-range contiguity, in situ transposition into stretched, HMW genomic DNA on the surface of a sequencing flowcell is performed using adaptor sequences to obtain distance spatial relationships by identification of the constrained physical locations (i.e. the relative coordinates at which physically linked sequencing templates are immobilized) of the adaptor sequences, hybridized DNA fragments, or a combination thereof. Additional embodiments and details regarding capturing short-range, mid-range and long-range contiguity are described further below.

Short Range Contiguity.

To capture information on short-range contiguity, a modified scheme for in vitro transposition in which degenerate barcodes within synthetic transposons are used in methods to symmetrically and uniquely tag shotgun library molecules originating from each flank of any given fragmentation event is provided, such that one can subsequently assign in silico "joins" between independent, adjacent-in-origin read-pairs. After sequencing the shotgun library and corresponding barcodes, adjacent fragmentation events can be identified via shared barcode sequences. Importantly, this strategy allows for the determination of local contiguity in a way that is almost completely independent of the primary sequence content.

Mid-Range Contiguity.

Even with long, high accuracy Sanger reads, the hierarchical approach of sequencing BAC clones was important to achieve a high quality reference assembly of the human genome, particularly in segmentally duplicated and structurally complex regions (Lander et al. 2001; Waterston et al. 2003; Waterston et al. 2002). Therefore, in some embodiments, methods that enable the grouping of short (or "shotgun") reads derived from the same fosmid/BAC-scale region of the genome (e.g., 20 to 200 Kb), to capture information for mid-range congruity are provided. These methods are discussed in detail below in Example 2.

As described below and in Kitzman et al. (Kitzman et al. 2011), this class of information is sufficient to extensively haplotype-resolve an individual human genome sequence. This mid-range contiguity information may also facilitate de novo genome assembly. For example, Gnerre et al. (Gnerre et al. 2010) recently described the de novo assembly of the human and mouse genomes to reasonably high quality using only short-read sequence data. This result, just as with the haplotype contiguity achieved by Kitzman et al. (Kitzman et al. 2011), required the use of fosmid library construction in order to partition the genome into ~40 Kb segments. In these methods, emulsions are used to compartmentalize high molecular weight (HMW) genomic DNA fragments, followed by emulsion PCR with primers bearing droplet-specific barcodes. Upon recovery, amplicons are tagged with barcodes that define groups of shotgun reads, with each group derived from the same 20-200 Kb region. In preliminary work relying on shotgun libraries derived from complex pools of fosmid clones, the sufficiency of this class of information to extensively haplotype-resolve an individual human genome with next-generation sequencing is demonstrated below.

Similar to the recently reported "subassembly" strategy (Hiatt et al. 2010), a long fragment library is converted to a population of nested sub-libraries, and a tag sequence directs the in silico grouping of short reads that are derived from the same long fragment, thereby enabling the localized assembly of long fragment sequences, i.e. "subassembled" reads. Subassembly extends the utility of short-read sequencing platforms to applications that normally require or benefit from long reads, e.g. metagenomics and de novo genome assembly. However, the methods according to the embodiments described herein enable subassembly over 20-200 Kb, rather than ~1 Kb, regions as previously described.

Long-Range Contiguity.

High throughput methods that include massively parallel, short read sequencing technologies are inherently limited with respect to several important goals, including the resequencing of segmental duplications and structurally complex regions of the human genome, the resolution of haplotype information in diploid and polyploidy genomes, and the de novo assembly of complex genomes. Further reductions in the cost-per-base of sequencing will do little to advance these goals. Rather, what is required are equivalently parallel methods of obtaining contiguity information at different scales. For example, the fact that the original de novo assemblies of the human and mouse genomes achieved a high quality (Lander et al. 2001; MSGC 2002), despite an order-of-magnitude less sequence coverage than lower quality assemblies based on short reads alone, is primarily a consequence of the inclusion of a broad spectrum of complementary sources of contiguity information, including: (a) long primary read lengths, (b) mate-paired reads from plasmids, fosmids, and BACs, (c) hierarchical clone-by-clone sequencing, and (d) genetic maps.

Although new approaches to DNA sequencing may continue to mature and surpass current technology, the most cost-efficient technologies (in terms of cost-per-base) may continue to be read-length limited. Therefore, contiguity information may be obtained, by supplementing low-cost, short-read sequences with contiguity information obtained by other technologies described below. Examples of methods for obtaining contiguity information in this way may include: 1) Long-range "mate-pair" protocols enable one to obtain read-pairs separated by a controlled distance. However, all current in vitro protocols employ a circularization step, such that the method is only efficient at separations of several kilobases. 2) Barcoding and sequencing of clone dilution pools (or their in vitro equivalent) can yield haplotype information on a genome-wide scale. However, the resolution of the method is limited to the types of fragments (e.g. fosmid) and number of pools that one can efficiently process. 3) Optical mapping using restriction enzymes has been successful in generating long-range contiguity maps for de novo genome assembly (Schwartz et al. 1993; Zhou et al. 2007; Zhou et al. 2009). However, this process is limited by false positive and negative cut sites due to star activity and inefficient cleavage, necessitating multiple optical maps from the same region to generate a consensus map. Furthermore, the non-uniform distribution of restriction enzyme recognition sites can limit the amount of useful information derived from repetitive or low complexity regions. 4) Optical sequencing on stretched single DNA molecules (non-fragmented) has yielded up to 3 bp of contiguous sequence information from multiple locations along the same molecule (Ramanathan et al. 2004). Because reads are generated directly from single molecules, issues of sample quantity and PCR bias are largely avoided.

As described in Example 3 below, in situ library construction and optical sequencing within the flow-cells of next-generation sequencing instruments represent an improved and efficient path towards a single technology that simultaneously captures contiguity information and primary sequence at diverse scales. The basic premise is to exploit the physical properties of DNA (by random coiling or stretching of high-molecular weight (HMW) DNA), in situ library construction (via in vitro transposition of adaptors to HMW DNA within a flow-cell), and the fully developed aspects of an operationally-realized next-generation sequencing instrument (polony amplification, sequencing-by-synthesis, imaging and data-processing), to generate multiple spatially related reads whose physical separation is either known or can be inferred from the relative coordinates at which the reads originate on the flow-cell. In one approach, the random coil configuration adopted by DNA in solution is exploited to spatially confine the ends and generate two reads within a confined surface area. In a related approach, optical sequencing on stretched DNA molecules within a native flowcell may also be performed.

Figure 12A:
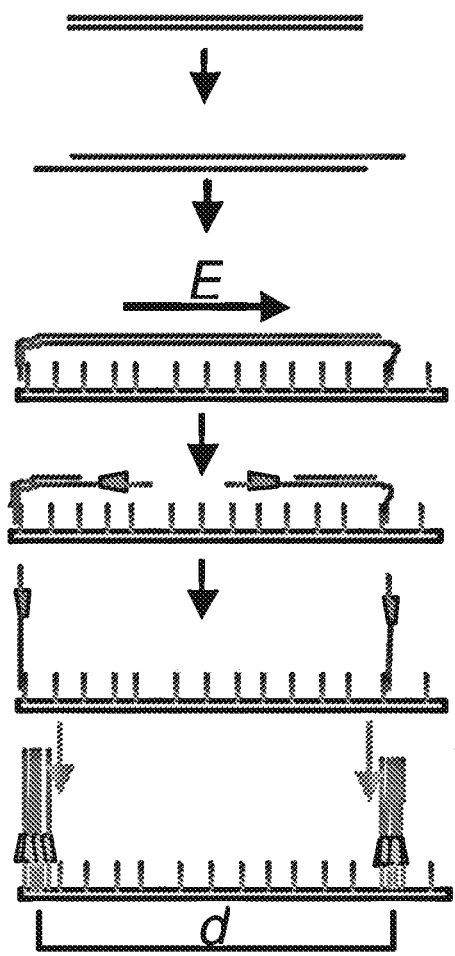
FIGS. 12A and 12B illustrate the use of in situ transposition for facilitating methods related to optical sequencing. (12A) Single templates are stretched out on a flowcell and fragmented to generate spatially separated clusters at a physical distance proportional to their genomic distance. (12B) Randomly coiled DNA is fragmented at its ends to generate clusters that are spatially confined to the area beneath the coil. Reads from either end can be deconvolved by using two different sequencing primers.
Figure 12B:
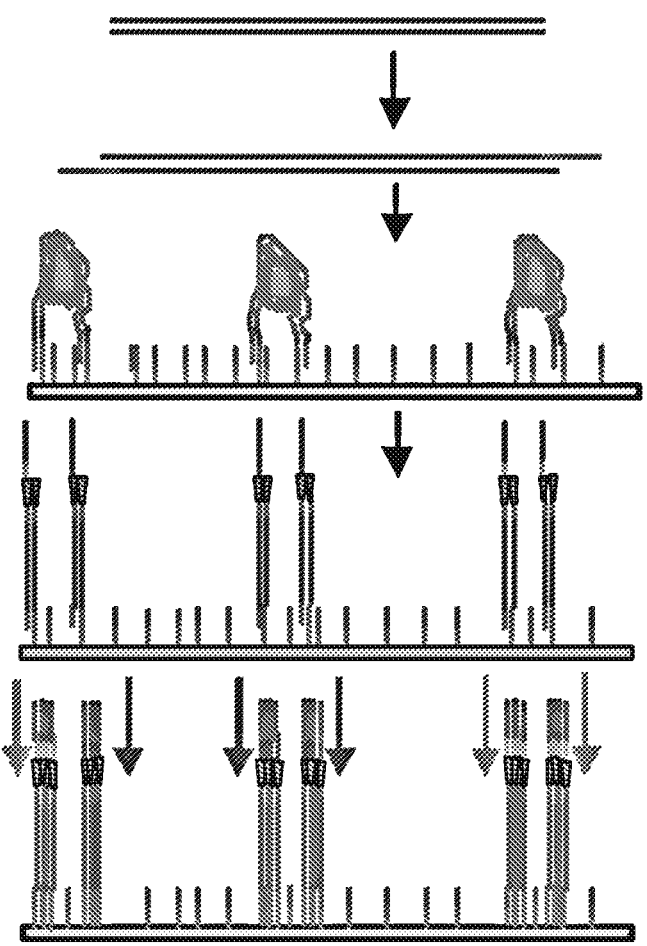
Figure 13A:
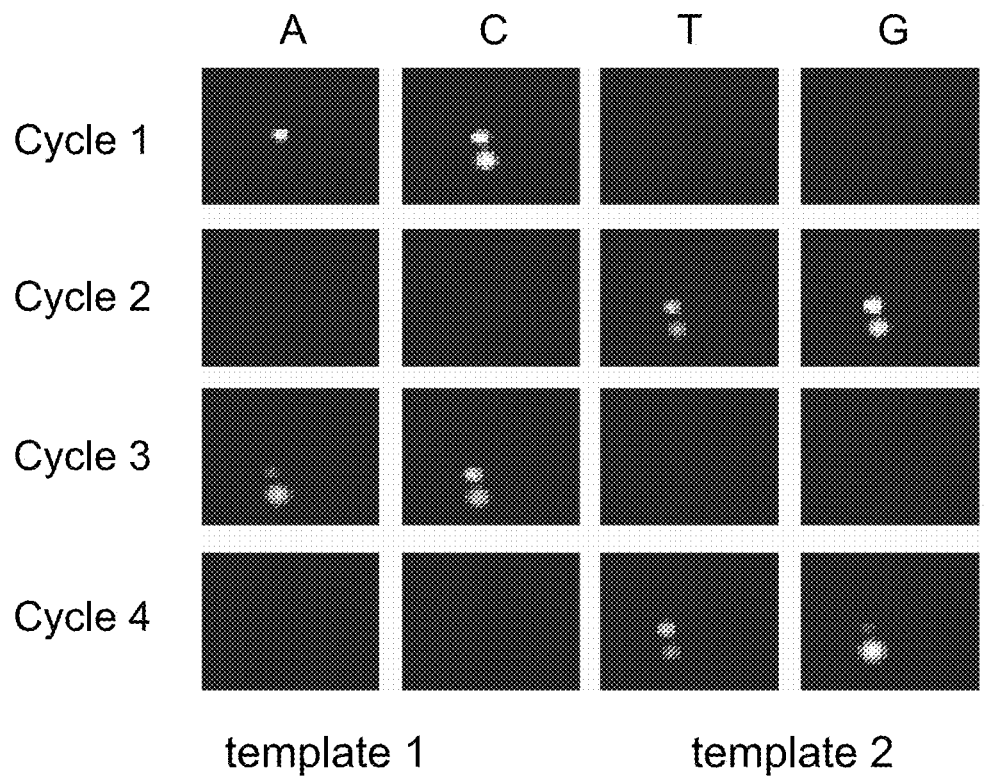
FIGS. 13A and 13B illustrate representative images of a spatially separated "cluster pair" for raw images of a "cluster pair" over four cycles of sequencing (13A); and raw integrated basecalling intensities of the two templates over the four cycles (13B).
Figure 13B:
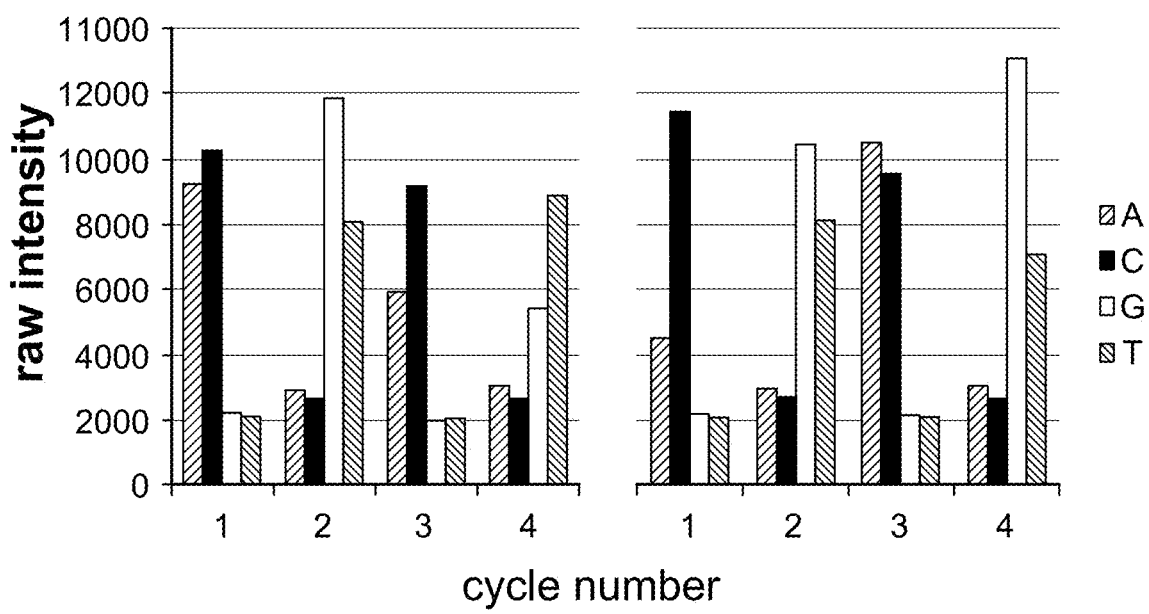

These approaches are discussed in detail below and, according to some embodiments, illustrate in vitro methods for long-distance mate-pairing that are not dependent on any circularization step. Success in obtaining paired-end reads from unstretched 2.7 Kb molecules is shown in FIG. 12$b$. Briefly, flowcell compatible adaptors (FCA1) were end-ligated to linearized, double-stranded puc19. This template was introduced to a flowcell (Illumina) and single-stranded ends were allowed to hybridize to the primer-coated surface. The templates were then treated in situ with transposase pre-loaded with FCA2 adaptors. Next, standard cluster PCR was performed, followed by sequencing-by-synthesis. Based on the primers used and the known sequence of pUC19, the first 4 bp were likely to be either AGCT or CGAG, depending on which end of the molecule the read was coming from. FIG. 13A (top) shows representative images of a spatially separated "cluster pair" for the first 4 cycles, and raw integrated basecalling intensities for both templates is shown in FIG. 13B (bottom). The observation of many such closely located pairs in an otherwise sparse field is consistent with a common origin from the ends of the same 2.7 Kb molecules. Further diluting the template still produced cluster pairs, strongly suggesting that these are not derived from two different templates that happened to hybridize nearby. Also, only ~20% of templates showed visible physical cluster separation (as in FIGS. 13A and 13B), while the remaining 80% of paired ends were co-localized and gave mixed reads. However, the proposed approach of using two different sequencing primers will allow deconvolved mixed reads from such immediately co-localized cluster pairs into two separate reads.

Figure 14B:
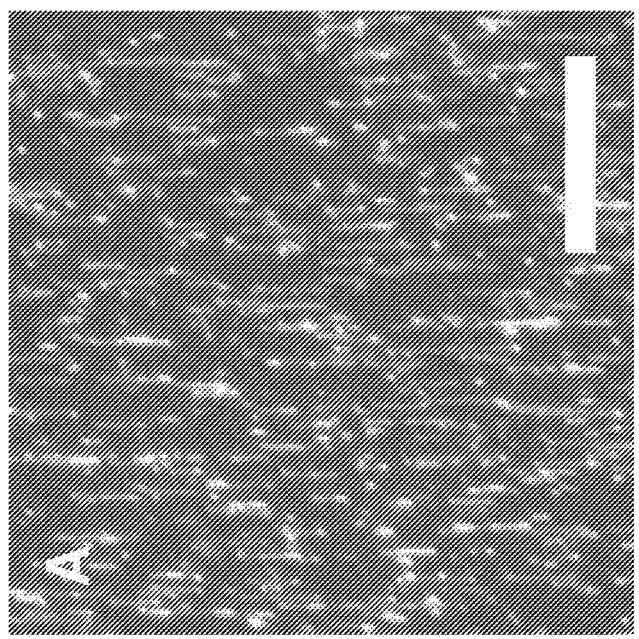
FIGS. 14A and 14B show representative images of (14A) 48.5 Kb lambda genomes that were stained with JOJO-1, tethered to a modified Illumina flowcell, and stretched with a 15V/cm electric field and (14B) stretched DNA like that in (14A) that was treated with transposomes for 5 minutes at 55° C. and imaged again. Imaging was performed on an Illumina GA2x. Scale bars=20 μm.
Figure 14A:
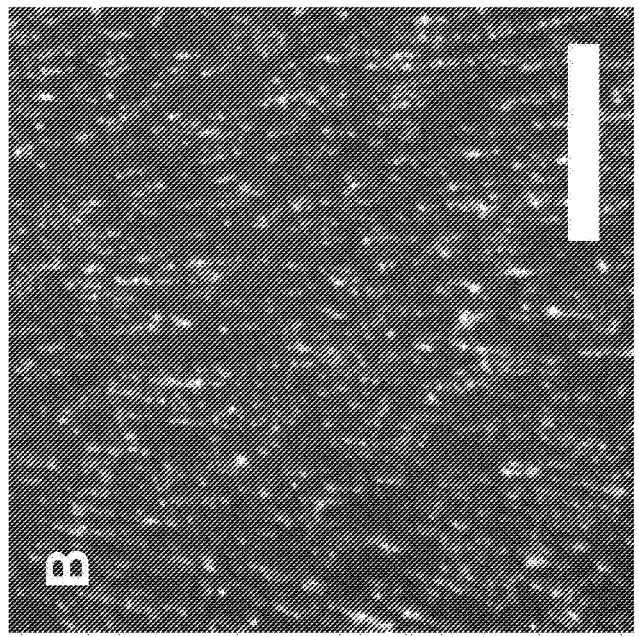

In other embodiments, the in situ fragmentation of linearly stretched 48.5 Kb DNA molecules is also demonstrated with transposomes. Briefly, flow-cells were cleaned using Piranha solution, treated with 2% 3-aminopropyltriethoxysilane (APTES), and loaded with JOJO-1 stained lambda DNA. The flowcell was then loaded with 6M KCl and an electric field of 15V/cm was applied at the input and output ports for 90 sec. Surfaces were imaged directly on an Illumina GA2 sequencer (FIG. 14A) to demonstrate that the ends of single 48.5 Kb molecules can be physically stretched over ~30 pixels. Surfaces were then treated in situ with transposome and re-imaged (FIG. 14B). Individual molecules were fragmented in multiple locations, demonstrating the enzyme's ability to maintain high activity even on surface-immobilized template. These methods may also be used to incorporate flowing in the "lock-down" bridge prior to fragmentation, so that clusters may be generated at the ends of long templates.

Based on the methods of short, mid-range and long-range contiguity embodiments described herein, several additional embodiments for capturing contiguity are provided below.

According to some embodiments, methods for capturing contiguity information are provided. In one embodiment, such methods may include constructing a library of shotgun nucleic acid molecules derived from target DNA wherein sequences adjacent to each fragmentation or insertion event are symmetrically tagged with barcodes; sequencing the shotgun library molecules and corresponding barcodes; and identifying sequences of adjacent origin via shared barcode sequences.

In another embodiment, methods for capturing contiguity information may include compartmentalizing target DNA fragments with emulsions or dilution; modifying target DNA fragments with transposase to insert primer sequences, either before or after compartmentalization; performing nucleic acid amplification using primers bearing compartment-specific barcodes; and sequencing the resulting library of shotgun nucleic acid molecules derived from target DNA and corresponding barcodes to define groups of shotgun sequence reads. In one aspect, the groups of reads sharing barcodes are derived from the same high molecular weight genomic DNA fragment.

In a further embodiment, methods for capturing contiguity information may include end-modifying target DNA molecules with an adaptor corresponding to one surface-bound primer; hybridizing both ends of the end-modified target DNA molecules to the surface-bound primer with or without stretching; performing transposition with non-surface-bound transposase complexes that include DNA transposase and sequences corresponding to a second surface-bound primer; performing cluster amplification to produce clusters of clonally derived nucleic acids; sequencing clusters of clonally derived nucleic acids; and determining whether overlapping or closely located clusters are derived from ends of the same target DNA molecules. In one aspect, such a method includes end-modifying high molecular weight DNA molecules with an adaptor corresponding to one flow cell primer; hybridizing both ends of the end-modified high molecular weight DNA molecules to a flow-cell with or without stretching; performing in situ transposition with transposase loaded with adaptors corresponding to a second flow cell primer; performing cluster PCR to produce visibly overlapping or closely located clusters; and determining whether overlapping or closely located clusters are derived from ends of the same high molecular weight DNA molecule.

Figure 25:
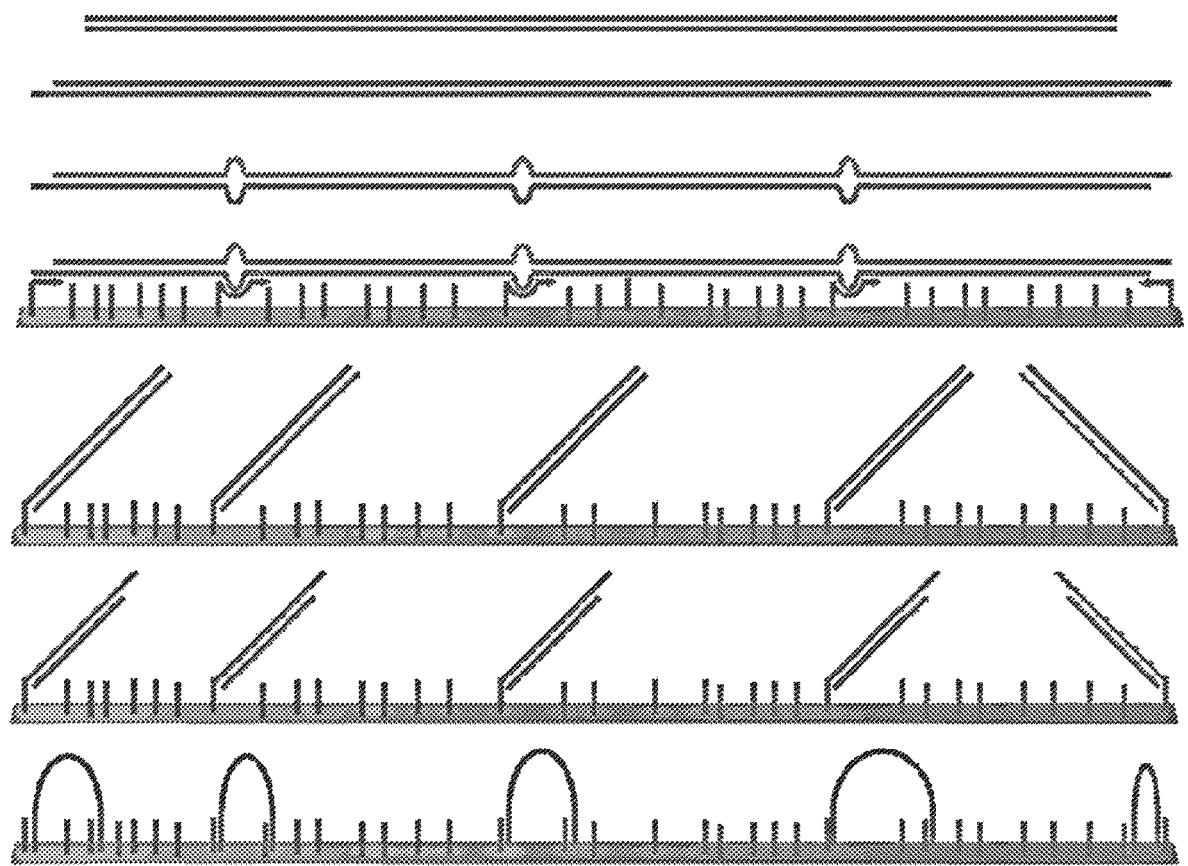
FIG. 25 illustrates a method for direct sequencing of transposon bubbles containing flowcell primers according to some embodiments.

In another embodiment, methods for capturing contiguity information may include modifying target DNA molecules with transposase to insert nucleic acid sequences corresponding to one or several surface-bound primers; hybridizing the internally modified target DNA molecules to the surface-bound primers with or without stretching; performing cluster amplification to produce clusters of clonally derived nucleic acids; sequencing clusters of clonally derived nucleic acids; and determining whether overlapping or closely located clusters are derived from the same target DNA molecules. In one aspect, such a method includes modifying high molecular weight genomic DNA with transposase to insert primer sequences corresponding to one or two flow cell primers; hybridizing the internally modified high molecular weight DNA molecules to a flowcell with or without stretching; performing cluster PCR to produce visibly overlapping or closely located clusters; and determining whether overlapping or closely located clusters are derived from the same high molecular weight DNA molecules as in FIG. 25.

In another embodiment, methods for capturing contiguity information include steps of (a) generating a surface to which nucleic acid sequences are bound that include a double-stranded DNA sequence corresponding to the recognition sequence of a DNA transposase; (b) assembling complexes comprising a DNA transposase bound to the surface-bound recognition sequence; (c) exposing complexes to target DNA, with or without stretching of the target DNA, and allowing for internal modification of the target DNA by the surface-bound transposase complex; (d) performing cluster amplification to produce clusters of clonally derived nucleic acids; (e) sequencing clusters of clonally derived nucleic acids; and (f) determining whether overlapping or closely located clusters are derived from the same target DNA molecule. In one aspect, an additional step may be included at any point before step (c) wherein target DNA is modified by exposure to non-surface-bound transposase complexes that include DNA transposase and sequences corresponding to a surface-bound primer. In another aspect, an additional step after step (c) and before step (d) may be included, wherein target DNA is further modified by exposure to non-surface-bound transposase complexes that include DNA transposase and sequences corresponding to a surface-bound primer.

Applications of Sequencing Technologies

The methods of capturing contiguity information described herein are useful in the improvement of uses and applications of the sequencing technologies described above. Suitable applications of DNA sequencing technologies that may be used in accordance with the methods described herein may include, but are not limited to bisulfite sequencing for determining DNA methylation, resequencing, de novo assembly, exome sequencing, RNA-Seq, ChIP-Seq, inferring chromosome conformation and genome-wide chromatin interaction mapping. In some embodiments, the methods for capturing contiguity information may be used with "cyclic-array" methods, for applications such as resequencing, de novo assembly, or both as described in detail in the Examples below.

Resequencing.

Resequencing human genomes has become relatively straightforward. For example, Bentley et al. (2008) sequenced the genome of a Yoruba male to ~40× coverage to identify ~4 million SNPs on the Illumina GA platform (Branton et al. 2008), i.e. massively parallel sequencing-by-synthesis on a dense array of unordered PCR colonies. Today, the Illumina HiSeq platform is able to generate the same quantity of data (135 gigabases (Gb)) in 8 days across 7 sequencing lanes that each yield ~100 million mappable, paired-end, 100 bp reads (PE100). For an exemplar cost of $3,700 per lane, the estimated cost for ~40× human genome resequencing is just over $25,000.

Furthermore, although short read lengths and modest raw accuracies are compatible with the highly accurate resequencing of ~94% of the human genome, that these technologies continue to fall short in at least two important ways. First, approximately 6% of the human genome consists of gene-rich segmental duplications or structurally complex regions that are prone to recurrent rearrangement. It is likely impossible to uniquely map short sequencing reads within this space, and extremely challenging to decipher complex structural variation. Second, current technology for genome resequencing is almost completely blind to haplotype, i.e., the phase with which polymorphisms along a single chromosome occur. Haplotype information is extremely useful for studies of gene-disease association, as well as for population genetic analyses. Neither of these deficiencies can be remedied by more sequencing with the same technology. Rather, these deficiencies reflect fundamental limitations of short-read sequencing.

De Novo Assembly.

In contrast with resequencing, there is still a long way to go with respect to generating high-quality de novo assembly of mammalian genomes using the same technologies. Generating 20 Gb, i.e. the ~8× coverage (Sanger) used to assemble the 2.5 Gb mouse genome in 2002 (Waterston et al. 2002), is now possible on a single Illumina HiSeq lane (PE100, $3,700). However, even with ~90× coverage, the best "next-generation" de novo assembly of the similarly complex human genome yields an N50 contig length of 7.4 Kb, a N50 scaffold length of 446 Kb, and sequence coverage of just 87% of the genome (Li et al. 2010). Further increases in coverage with short-read data would likely only minimally improve assembly quality (Li et al. 2010). By comparison, the initial assembly of the mouse genome, based on over an order of magnitude of less data, had an N50 contig length of 25.9 Kb, an N50 scaffold length of 18.6 megabases (Mb), and sequence coverage of 95% of the genome (Waterston et al. 2002).

Bisulfite Sequencing.

Methods for bisulfite sequencing for measurement of DNA methylation are provided herein. DNA methylation is a widespread epigenetic modification that plays a pivotal role in the regulation of the genomes of diverse organisms. The most prevalent and widely studied form of DNA methylation in mammalian genomes occurs at the 5 carbon position of cytosine residues, usually in the context of the CpG dinucleotide. Microarrays, and more recently massively parallel sequencing, have enabled the interrogation of cytosine methylation (5mC) on a genome-wide scale (Zilberman and Henikoff 2007). However, the in vivo study of DNA methylation and other epigenetic marks, e.g. in specific cell types or anatomical structures, is sharply limited by the relatively high amount of input material required for contemporary protocols.

Methods for genome-scale interrogation of methylation patterns include several that are preceded by the enrichment of defined subsets of the genome (Meissner et al. 2005; Down et al. 2008; Deng et al. 2009), e.g., reduced representation bisulfite sequencing (RRBS) (Meissner et al. 2005) and anti-methylcytosine DNA immunoprecipitation followed by sequencing (MeDIP-seq) (Down et al. 2008). An advantage of such methods is that they can be performed with limited quantities of starting DNA (Gu et al. 2011). However, they are constrained in that they are not truly comprehensive. For example, the digestion-based RRBS method interrogates only ~12% of CpGs, primarily in CpG islands (Harris et al. 2010), with poor coverage of methylation in gene bodies (Ball et al. 2009) and elsewhere. Furthermore, RRBS does not target cytosines in the CHG or CHH (H=A,C,T) contexts which have been shown to be methylated at elevated levels in the early stages of mammalian development (Lister et al. 2009).

The most comprehensive, highest resolution method for detecting 5mC is whole genome bisulfite sequencing (WGBS) (Cokus et al. 2008; Lister et al. 2009; Harris et al. 2010). Treatment of genomic DNA with sodium bisulfite chemically deaminates cytosines much more rapidly than 5mC, preferentially converting them to uracils (Clark et al. 1994). With massively parallel sequencing, these can be detected on a genome-wide scale at single base-pair resolution. This approach has revealed complex and unexpected methylation patterns and variation, particularly in the CHG and CHH contexts. Furthermore, as the costs of massively parallel sequencing continue to fall, whole genome bisulfite sequencing is increasingly affordable. However, WGBS is limited in that current protocols call for 5 micrograms of genomic DNA as input (Cokus et al. 2008; Lister et al. 2009; Li et al. 2010), which is essentially prohibitive for many samples obtained in vivo.

In some embodiments, a transposase-based in vitro shotgun library construction ("tagmentation") for whole genome bisulfite sequencing is adapted as described below. This method, referred to herein as tn5mC-seq, enables a >100-fold reduction in starting material relative to conventional protocols, such that highly complex bisulfite sequencing libraries are generated from as little as 10 nanograms of input DNA, and ample useful sequence from 1 nanogram of input DNA. tn5mC-seq is demonstrated by sequencing the methylome of a human lymphoblastoid cell line to approximately 8.6× high quality coverage of each strand.

Further, methods for methylating discontinuous synthetic transposons are provided that use a double stranded DNA portion of the Tn5 recognition sequence as well as a single stranded DNA overhang containing either adaptor sequence 1 or 2 wherein all cytidine or cytosine residues are methylated. In one embodiment, a nick translation step is performed. After the nick traslation, the resulting transposition generates adaptor flanked DNA fragments where each strand has both adaptors, one of which is methylated. PCR is then performed on the nick translated material with an accepted lower efficiency of the unmethylated strand of the adaptor that was generated from the nick translation.

In another embodiment, the nick translation step is not performed and the second adaptor is added later as described below. The fragment library is then subjected to bisulfite treatment to convert all unmethylated cytidines to uracil residues. The second adaptor is then added added in one of two ways: (1) by adding an A-tail and then using a primer containing poly-T and an adaptor overhang, or (2) by extending a template containing a 3' blocked N6 (at bisulfite treated nucleotide ratios) with a 5' adaptor overhang that will be extended through from the 3' end of the fragment. After addition of the second adaptor, PCR and sequencing is then performed. One advantage of this method is that the high efficiency of conversion of gDNA to adaptor modified fragments will allow for much less DNA to be used in the construction of libraries to be subjected to bisulfite treatment.

Briefly, the procedure is as follows. First, transposase with adaptors containing the dsDNA transposase recognition sequences are loaded with an ssDNA adaptor overhang in which all cytosine (C) residues are methylated. Next, transposition into genomic DNA is performed, fragmenting the DNA and appending a methylated C, 5' overhang adaptor. If nick translation is performed, the adaptor is extended to both ends of the molecule, however, the 3' adaptor will not be methylated. The library is then subjected to bisulfite treatment to convert all unmethylated C residues to U residues. If nick translation was not performed in the previous step, a second 3' adaptor may be added by one of two approaches: (i) DNA fragments are A-tailed, and the 3' adaptor is appended to the fragments using a 3' poly-T 5' adaptor primer; or (ii) DNA fragments are allowed to extend on an oligo comprised of a 3' blocked N6 (at complementary bisulfite treated nucleotide composition) and a 5' adaptor overhang. Finally, PCR is performed, followed by sequencing According to other embodiments, the method of bisulfite sequencing may include steps of (a) performing in vitro transposition into target DNA molecules with transposase complexes that include double stranded DNA transposase recognition sequences with a single stranded DNA adaptor overhang having methylated cytosine residues; (b) subjecting modified target DNA molecules to bisulfite treatment; (c) performing nucleic acid amplification to produce a nucleic acid library; and (d) sequencing the resulting nucleic acid library. In some aspects, a second adaptor to nucleic acid fragments derived from target DNA after step (a) and before step (b), wherein the second adaptor is designed to facilitate nucleic acid amplification in step (c) may be incorporated. In other aspects, a second adaptor to nucleic acid fragments derived from target DNA, after step (b) and before step (c), wherein the second adaptor is designed to facilitate nucleic acid amplification in step (c).

In other embodiments, the method of bisulfite may include steps of (a) modifying double stranded DNA (dsDNA) transposase recognition sequences with a single stranded DNA (ssDNA) adaptor overhang having methylated cytosine residues; (b) performing in vitro transposition with transposase loaded with adaptors containing the modified dsDNA transposase recognition sequences to generate a library of DNA fragments; (c) subjecting the library of DNA fragments to bisulfite treatment; (d) performing a PCR method to amplify a target; and (e) sequencing the target. In some embodiments, an additional step of nick translation may be performed after step b) and before step (c). In other embodiments, nick translation is not performed. In this case, a second adaptor is added after step (c) and before step (d). The second adaptor may be added by (i) adding an adenosine (A) tail to the DNA fragments and appending a 3' adaptor to the fragments using a 3' poly-T 5' adaptor primer; or (ii) allowing the DNA fragments to extend on an oligonucleotide comprising a 3' blocked N6 and a 5' adaptor overhang.

Inferring chromosome conformation. According to some embodiments, methods for inferring chromosome conformation are provided. These methods may include cross-linking DNA within cells; isolating chromatin fibers; removing and digesting chromatin fragments; purifying chromatin DNA fragments; ligating adaptors to chromatin DNA fragments, forming chromatin DNA fragment complexes; and generating 3-dimensional models of chromosomal positions by pairing neighboring clusters of chromatin DNA fragment complexes. In one embodiment, the method may include steps of (a) cross-linking DNA within cells; (b) isolating cross-linked DNA from cells; (c) fragmenting the cross-linked DNA; (d) end-modifying fragmented, cross-linked DNA molecules with an adaptor corresponding to one surface-bound primer; (e) hybridizing ends of the fragmented, end-modified target DNA molecules to the surface-bound primer; (f) performing transposition with non-surface-bound transposase complexes that include DNA transposase and sequences corresponding to a second surface-bound primer; (g) performing cluster amplification to produce clusters of clonally derived nucleic acids; (h) sequencing clusters of clonally derived nucleic acids; and (i) determining physical interactions between chromosomal positions by paring neighboring clusters together. In some aspects, an isolated cross-linked DNA may be part of a cross linked DNA-protein complex. In this case, the method for inferring chromosome further conformation may additionally include a step of enriching for one or more specific cross linked DNA-protein complexes by immunoprecipitation after step (c) and before step (d).

In other embodiments, a method for identifying interactions between transcription factor binding sites is provided. Such a method may include inducing a population of cells with a hormone; immunoprecipitating cells to isolate chromatin fibers; producing chromatin fragments by cross linking cells and breaking chromatin fibers; repairing ends of chromatin fragments and ligating ends to adaptors, producing chromatin complexes; generating clusters corresponding to the chromatin complexes; and determining interactions between chromosomal positions by paring neighboring clusters together.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Several properties of in vitro transposition may be exploited to develop ultra-low-cost, massively parallel sequencing methods for capturing contiguity information at diverse scales. First, modified Tn5 transposomes attack DNA in vitro with high efficiency and at high density, in a reaction that catalyzes the insertion of common sequences, with or without fragmentation depending on whether the synthetic transposon is continuous or discontinuous. Second, the pattern of transposome attack is relatively random with respect to sequence content. Third, degenerate subsequences, in addition to common adaptor sequences, may be readily included within the synthetic transposons. Fourth, in vitro transposition is inexpensive as a single volume, aqueous-phase, enzymatic reaction. Examples 1-3 are directed at the development of massively parallel methods that exploit in vitro transposition to inform short-range, mid-range, and long-range contiguity, respectively. Example 4 is directed at the development of methods that exploit in vitro methylated transposition to capture contiguity information. Example 5 is directed at the development of methods for measuring DNA-DNA and DNA-protein interactions within smaller populations of cells that exploit infinipair technology to directly sequence multiple fragments off of immunoprecipitated DNA that has been cross linked. Example 6 is directed at integrating these methods to demonstrate high quality de novo genome assembly and haplotype-resolved genome resequencing.

General Approach

Contiguity Information is a Primary Goal.

The methods in the Examples described below address a "blind spot" in the next-generation sequencing field. Specifically, the methods address the lack of ultra-low-cost methods to determine contiguity information at broader scales.

These methods and their associated costs are dependent on the sequencing technology with which they are integrated, as this is the method by which the primary sequence coupled to the contiguity information is decoded. The methods below are performed using a commercially available, cyclic-array platform (e.g., Illumina GA2x or HiSeq). However, all of the methods described herein may be integrated with other approaches to DNA sequencing, e.g. nanopore sequencing, other cyclic-array platforms. Broad compatibility will ensure that these methods can be combined with any technology that emerges as the best in terms of cost-per-base.

Materials and Methods

In Vitro Transposition for Capturing Contiguity Information.

Although Examples 1-6 are technically diverse, a common thread is their reliance on high density, random, in vitro transposition as a novel means of physically shattering genomic DNA in creative ways that facilitate the recovery of contiguity information at different scales. The initial interest in this technology was based on its potential utility for low-cost, low-input, in vitro preparation of shotgun libraries. As shown in FIG. 1, a modified Tn5 transposase catalyzes fragmentation and adaptor incorporation in a single, 5 minute step. In conventional in vitro transposition, inverted 19 bp mosaic-end (ME) sequences flanking transposon DNA are recognized by the transposase and form a stable homodimer synaptic complex in solution. This "transposome" inserts the transposon into target DNA. When applied for library preparation, the transposome is instead comprised of enzyme and free ME sequences with adaptor overhangs. Insertion of the discontinuous transposon results in fragmentation via symmetrical insertion of the ME sequence with asymmetrical 5' adaptor overhangs. PCR amplification with primers complementary to the adaptors yields a shotgun fragment library.

Figure 2:
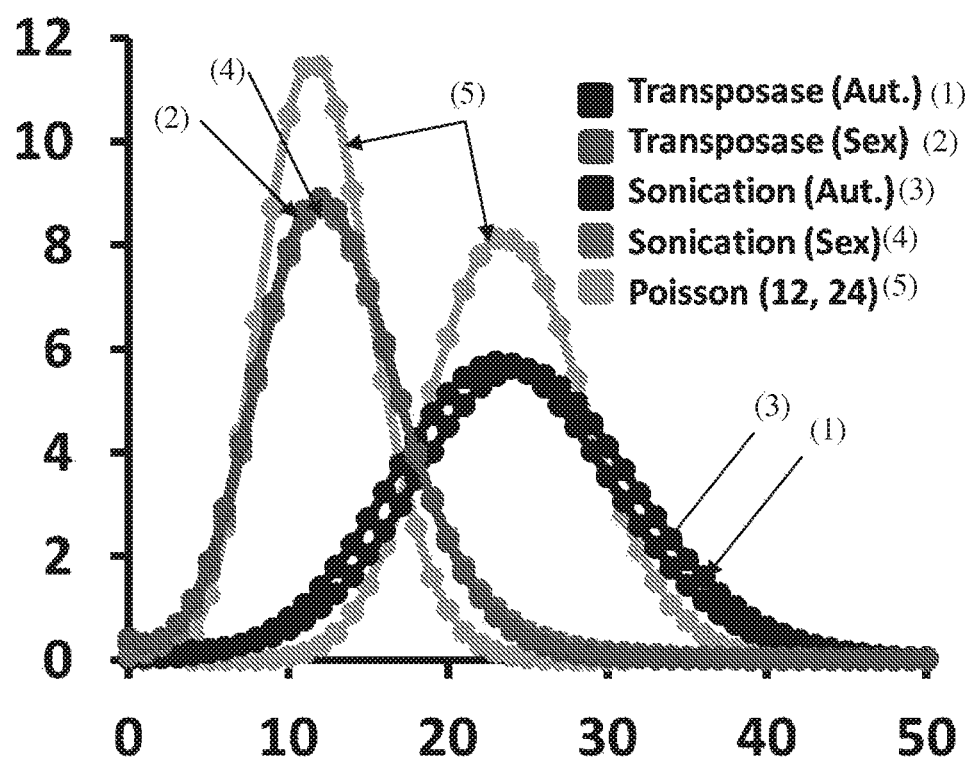
FIG. 2 is a histogram of fold-coverage with whole genome sequencing (x-axis=fold-coverage; y-axis=% of genome) of libraries from a male human generated by standard methods ('sonication') versus the transposome method ('transposase'), with autosomes ('Aut.') and sex chromosomes ('Sex') plotted separately.

To address concerns regarding insertion bias and library complexity, extensive comparisons were performed with traditional methods of in vitro shotgun library construction (Adey et al. 2010). The analysis revealed a slightly greater bias with respect to sequence content at fragmentation sites with the transposome-based method. However, this was of negligible impact in terms of the coverage distribution during whole human genome resequencing (FIG. 2), and the methods exhibited equivalent G+C bias. Critically, it was noted that the complexities of transposome libraries made from as little as 400 nanograms were equivalent to or greater than the complexities of standard libraries made from much larger amounts of input DNA.

Figure 3:
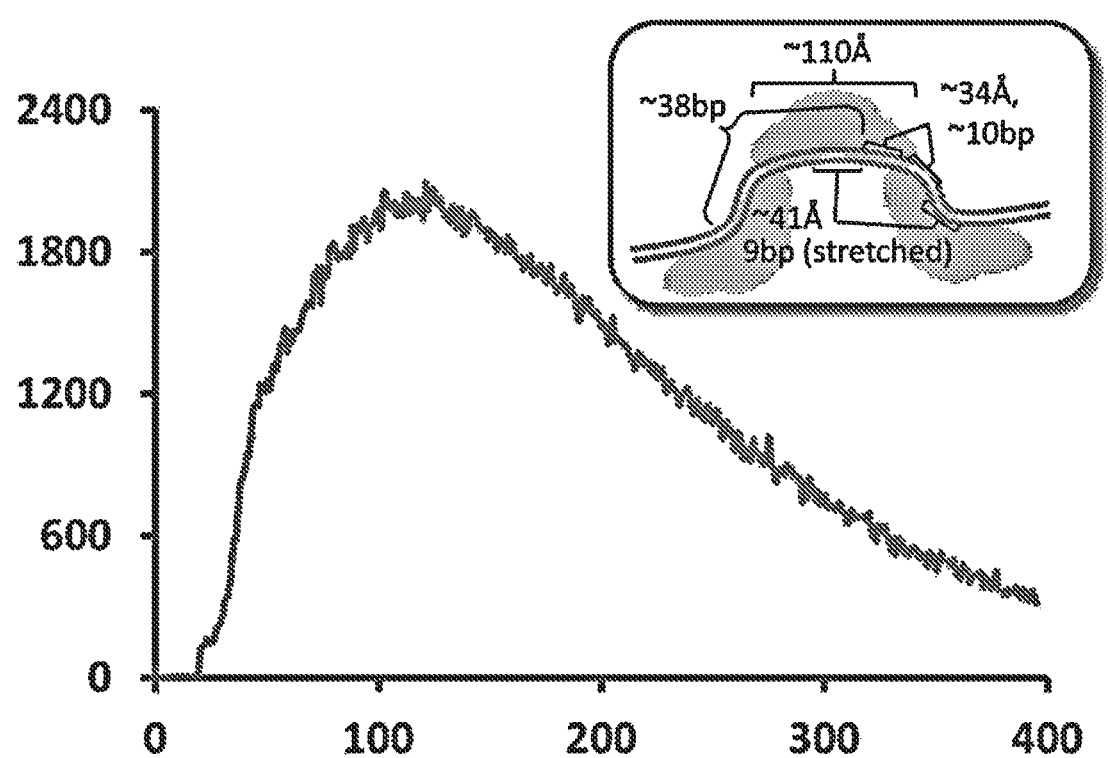
FIG. 3 is a histogram of fragment sizes (x-axis=base-pairs; y-axis=counts) resulting from high-density, in vitro fragmentation with a synthetic, discontinuous transposon. The inset shows a model for transposome occupancy consistent with a steric hindrance model for the sharp drop at ~35 bp.

The library complexities observed with this method suggests that the mass conversion efficiency of genomic DNA into adaptor-flanked library is high, as fragmentation events may be occurring in close succession along any given stretch of genomic DNA in order to generate sequencing-compatible fragments of several hundred base-pairs. Indeed, in analyzing the distribution of fragment lengths resulting from this method, we observe a sharp decrease at ~35 bp that is likely secondary to steric hindrance from adjacent, attacking transposomes (FIG. 3). Even with a PCR-free version of the protocol (to avoid skewing the fragment size distribution), the data suggests that the bulk of adjacent transposome reactions (>95%) are separated by 35 to 600 bp. In principle, this high efficiency of mass conversion should translate into low input requirements. Consistent with that, even with input as low as 100 picograms (30 haploid equivalents of the human genome), obtain complex libraries may be obtained. At 10 picograms (3 haploid equivalents complexity begins to bottleneck, but millions of uniquely mapping read-pairs may be observed nonetheless.

Example 1: Short-Range Contiguity

1.A. Symmetrically and Uniquely Tagging Fragmentation Events

Figure 4:
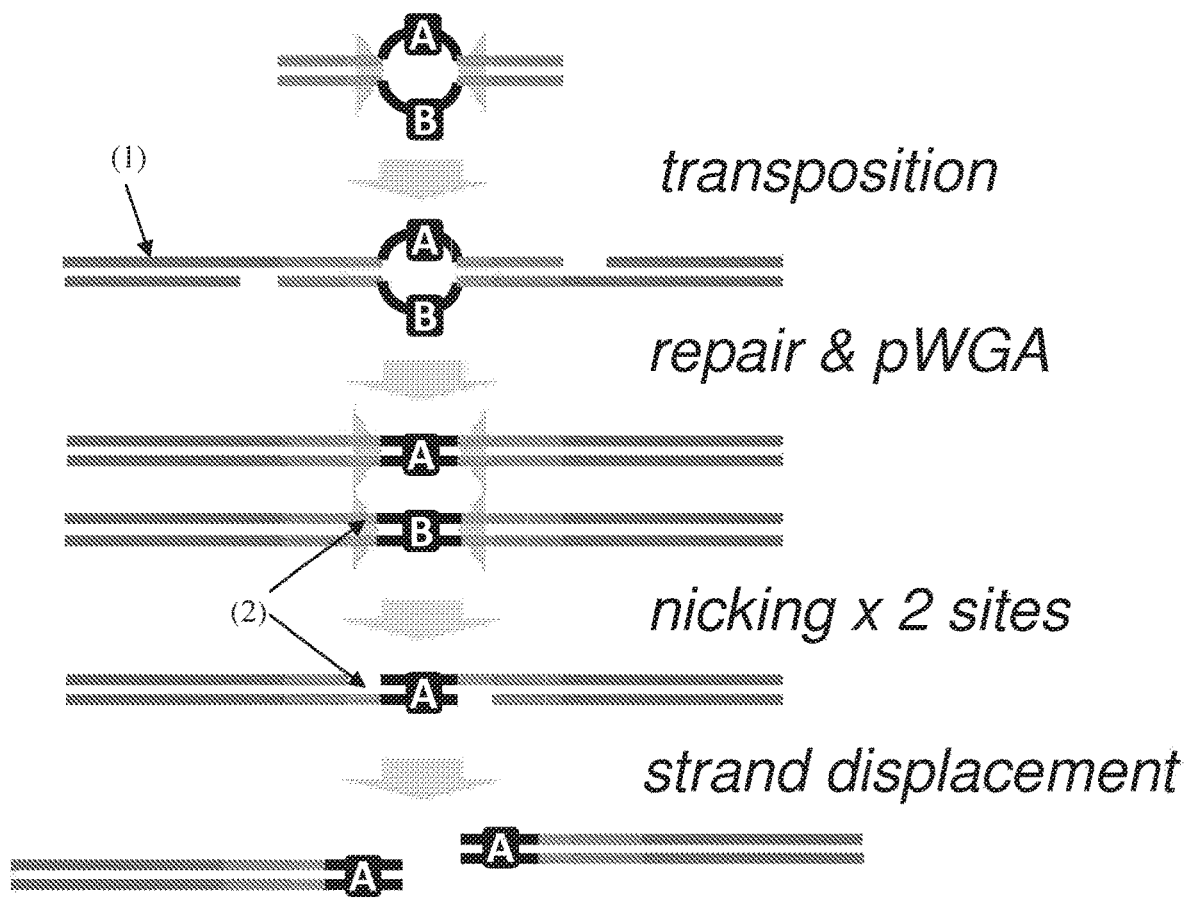
FIG. 4 shows in vitro, high-density insertion of transposomes with degenerate, single-stranded "bubbles" (A/B) to genomic DNA (dark gray, (1)) is followed by whole genome amplification (WGA) to resolve each strand of the degenerate stretch (to A/A or B/B). Nicking (at medium gray sites, (2)) and strand displacing polymerization completes fragmentation, but also leaves junctions symmetrically tagged with the same barcode (A/A (shown) or B/B).

The fragmentation of genomic DNA, whether by mechanical or enzymatic methods, results in a complete loss of information as to the pairing of molecules that derive from either side of any single "break". To preserve this information, a method was devised to associate a unique barcode with both ends of fragments derived from each break introduced by in vitro transposition (FIG. 4). In brief, transposase may be used to catalyze in vitro insertion of synthetic transposons containing a degenerate single-stranded "bubble" flanked by nicking restriction endonuclease site into very low amounts of genomic DNA, i.e., less than 5 haploid human genome equivalents. In contrast with the approach described in FIG. 1, the synthetic transposons are continuous, containing the 19 bp ME sequences along with two endonuclease nicking sites flanking a 25 bp degenerate sequence. Since the degenerate region is not complementary between the top and bottom strands, a single-stranded bubble is present, increasing flexibility to aid in the formation of a synaptic complex with two transposase monomers. After inserting these synthetic transposons to high density (every 35 to 600 bp), a 9 bp lesion, resulting from the transposition mechanism, is repaired via a gap-fill and ligation reaction.

The construct is then subjected to primase-based whole genome amplification (pWGA), which resolves the bubbles at the degenerate regions while yielding a relatively uniform amplification (Li et al. 2008). This material is then digested to completion by both nicking endonucleases, which introduce nicks on opposite strands flanking the degenerate region. Finally, extension with a strand-displacing polymerase fragments the target DNA, yielding molecules that terminate in an identical barcode sequence, i.e. symmetrical tagging. At this point, standard protocols (A-tailing, adaptor ligation, PCR) can be applied for compatibility with massively parallel sequencing-by-synthesis. Separate reads can be used to access the barcodes and primary sequence at each end of each library molecule.

The barcodes used herein should be unique to each fragmentation event because they are derived from a 25 bp degenerate stretch and can be used in silico to successively link strings of read-pairs derived from adjacent transposome insertions. These "joins" are based on barcodes alone, thus they are entirely independent of the primary sequence content.

Figure 16:
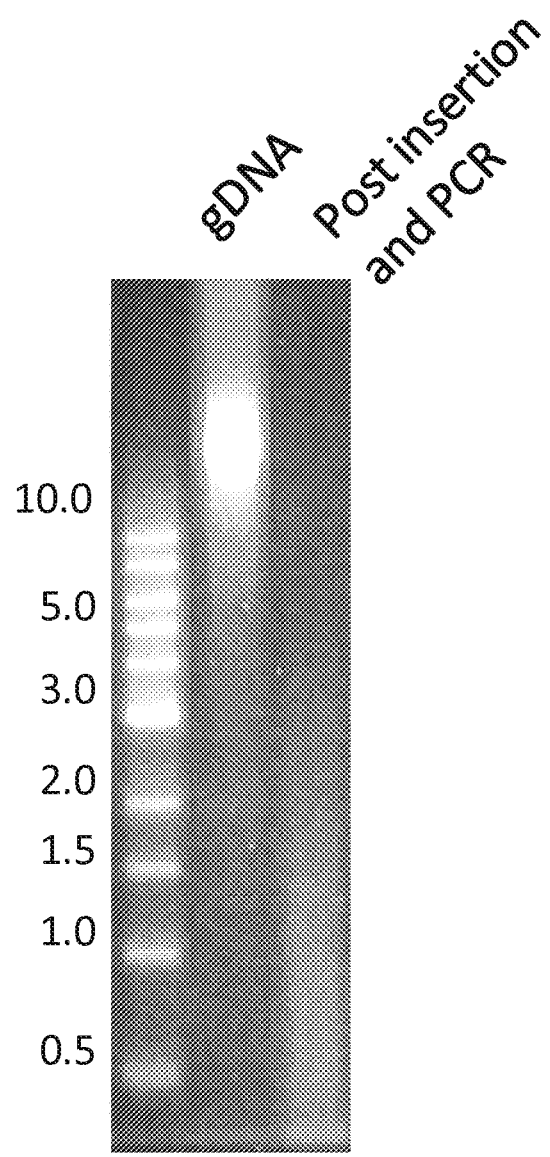
FIG. 16 illustrates high-density insertion of synthetic transposons containing single-stranded bubbles into genomic DNA. Lane 1=ladder (kb); Lane 2=unfragmented genomic DNA; Lane 3=post-insertion, post PCR material.

To test the feasibility of this approach, a synthetic transposon containing a single-stranded bubble with fixed, non-complementary sequences corresponding to two primers was designed (as shown in the first step of FIG. 4, but with fixed non-complementary sequences for A & B rather than degenerate sequences). These synthetic transposons were loaded to EZ-Tn5 transposase and reacted with genomic DNA under appropriate conditions. After gap-fill and repair of the expected 9 base-pair lesions resulting from transposition events, PCR with primers corresponding to the non-complementary synthetic bubble sequences yielded amplicons with a broad distribution of sizes ranging from ~0.5 to ~3 Kb (FIG. 16). This experiment confirms that synthetic, contiguous transposons containing single-stranded bubbles can be inserted with reasonable efficiency. To achieve a denser distribution of insertion sites, this method should be optimized. In particular, the efficiency with which the transposase is loaded with synthetic transposons may be improved. As the steric hindrance of adjacent, attacking transposase complexes puts an upper bound on insertion density (FIG. 3), a large molar excess of properly loaded transposome complexes will likely achieve a denser insertion distribution.

1.B. Evidence that Adjacent Events are Detectable

Figure 5:
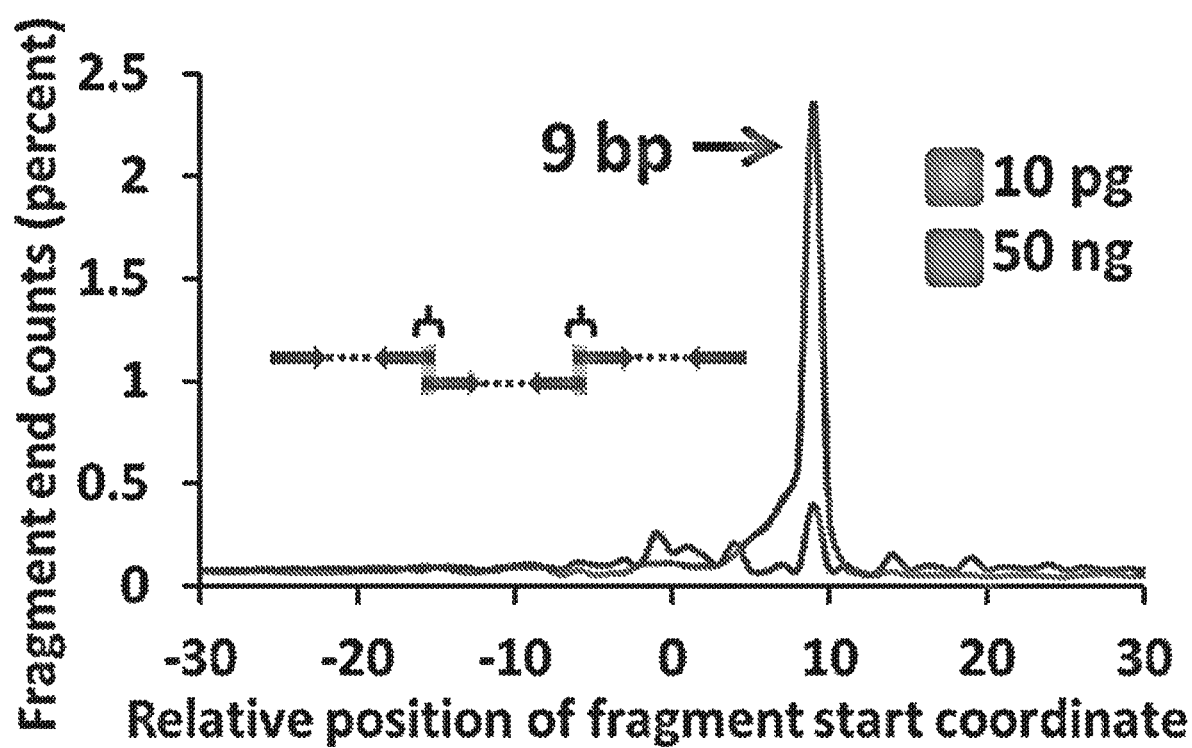
FIG. 5 shows independent reads derived from limited sequencing of transposase-based shotgun libraries show enrichment for mapping at 9 bp intervals. This phenomenon is much more pronounced with ultra-low input (10 pg, arrow) relative to low input (50 ng, no arrow), reflecting greater sampling of a lower number of discrete fragmentation events.
Figure 6:
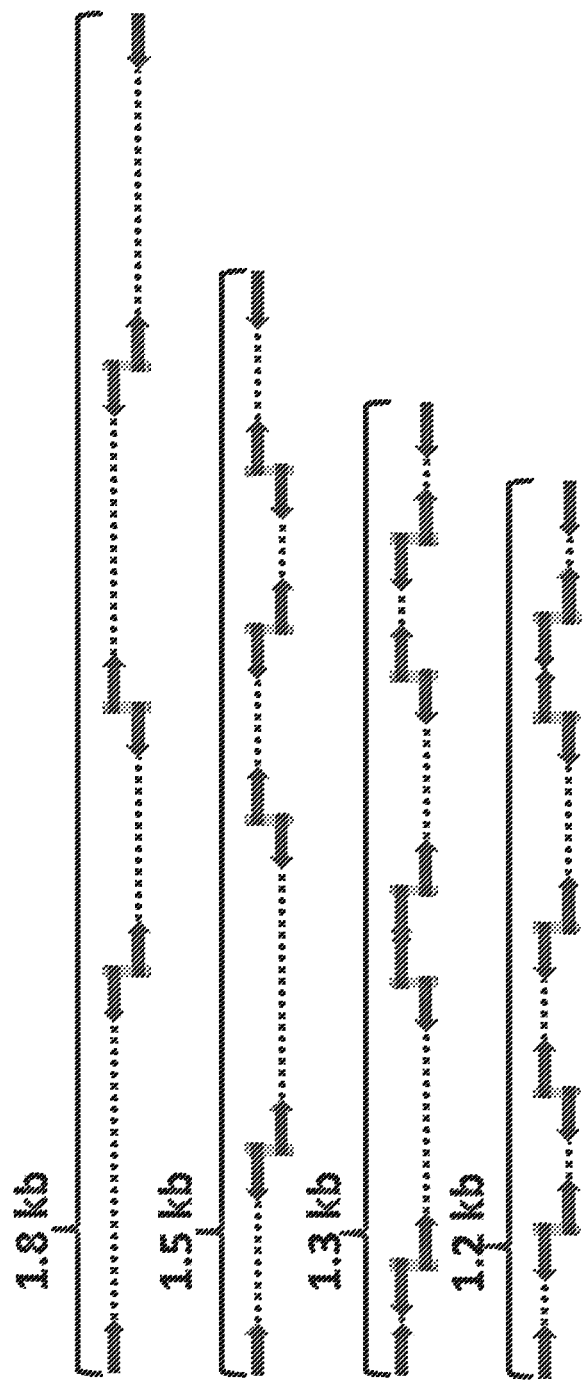
FIG. 6 is a schematic diagram, based on examples observed in real data, showing that read-pairs mapping to adjacent locations with 9 bp overlaps are likely to have derived from adjacent fragmentation events. In complexity-limited data based on a library derived from an 'ultra-low-input' sample, chains of 4 to 6 locally derived read-pairs may be identified that collectively span ~1 Kb to ~2 Kb.

To evaluate whether adjacent fragmentation events are potentially detectable by sequencing, ~2 million uniquely mapping read-pairs were mined from the sequencing of a transposome-fragmented shotgun library derived from 10 picograms of human genomic DNA (3 haploid equivalents). Because 9 bp duplication occurs at each end of each fragmentation event, molecules derived from either side of each event should map to the genome with a 9 bp overlap. As a consequence, a clear increase in "read 2" mapping locations was observed 9 bp from the "read 1" start-sites of other read-pairs (FIG. 5). This signature was markedly more pronounced in this ultra-low-input library as compared to libraries that were generated from larger amounts of starting material. Using this 9 bp overlap as evidence for fragments originating from the same breakpoints, chains of 4 to 6 read-pairs were identified that were derived from successive, adjacent fragments that collectively span ~1 Kb to ~2 Kb (FIG. 6).

1.C. Method Development and Performance Parameters

The strategy described above (see 1.A) is one of several related methods that have been devised to (1) attain symmetrically and uniquely tagging fragmentation events and (2) successively link strings of sequence read-pairs derived from adjacent transposome insertions by exploiting these tags during analysis. An alternative approach for symmetrical tagging has also been developed, wherein individual transposases are loaded with symmetrically tagged but formally discontiguous oligonucleotides (or "oligos"), such that both tagging and fragmentation can take place in a single step.

Figure 17:
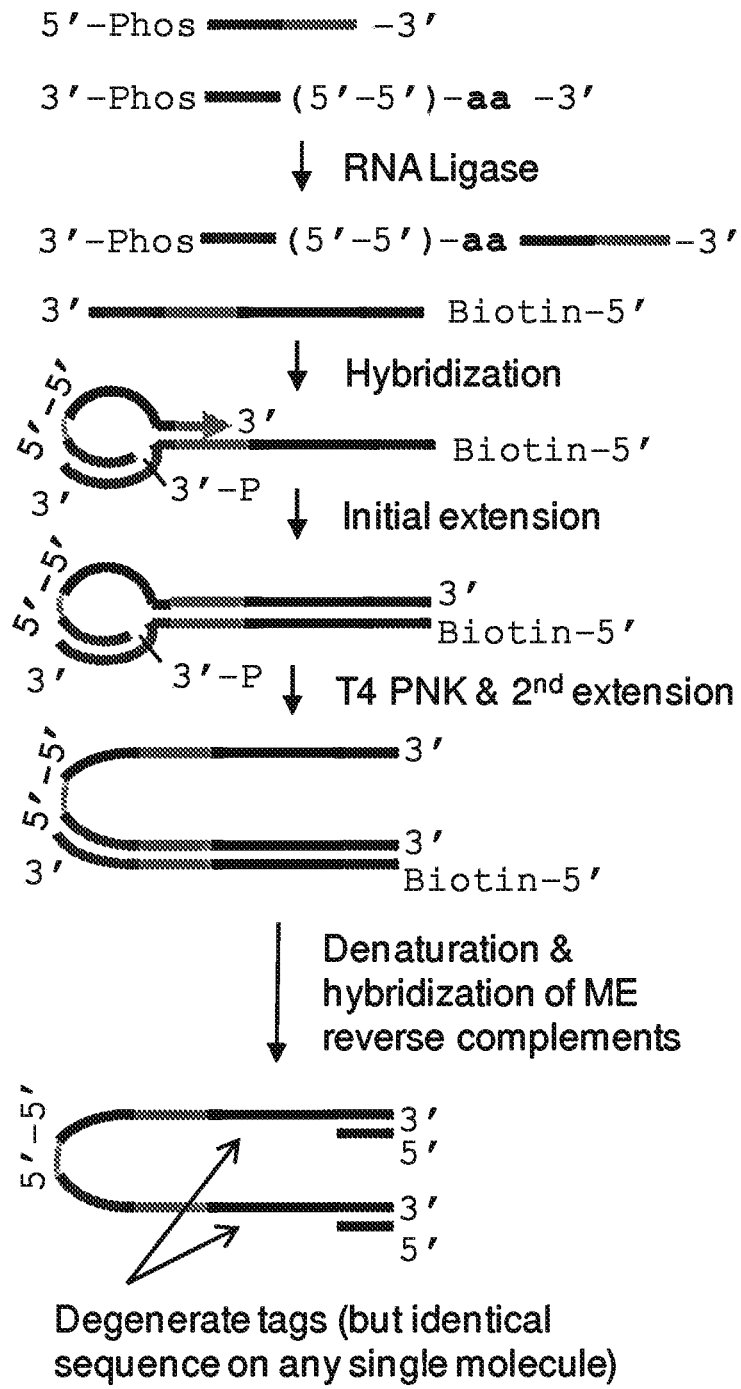
FIG. 17 illustrates the construction of symmetrically tagged, 5'-to-5' linked transposon reagent.

A method based on this alternative approach was devised to construct a symmetrically tagged, 5'-to-5' linked transposon reagent (FIG. 17). To generate this reagent, two primers were linked, one of which contains a 5'-5' inverted adenine RNA moiety and a 3' phosphate blocking group. Single-stranded ligation between the terminal RNA base with the 5' phosphorylated DNA base of the other oligonucleotide is carried out with T4 RNA ligase. The 5'-5' linked primers are then hybridized to an oligonucleotide containing appropriate complementary sequences for both primers, a degenerate stretch to serve as the tag (e.g. 20 randomized nucleotides— shown in black in FIG. 17), and the 19 bp mosaic-end (ME) sequence recognized by the transposon. The first primer in the 5'-5' pair is extended while the other end is blocked by the 3' phosphate. Next, T4 polynucleotide kinase (T4 PNK) is used to remove the 3' blocking phosphate and the second primer is extended with a strand-displacing polymerase. Each single molecule of the resulting species includes two oligonucleotides, linked 5'-to-5' by the inverted adenine moiety, that are identical across the degenerate stretch and that each terminate in the 19 bp mosaic-end (ME) sequence. Gel-based purification is used to remove extension byproducts, and then appropriate oligonucleotides are hybridized to double-strand the ME subsequences at each end. The resulting species are both symmetrically tagged at the single molecule level, and readily loadable to the Tn5 transposase.

Figure 18:
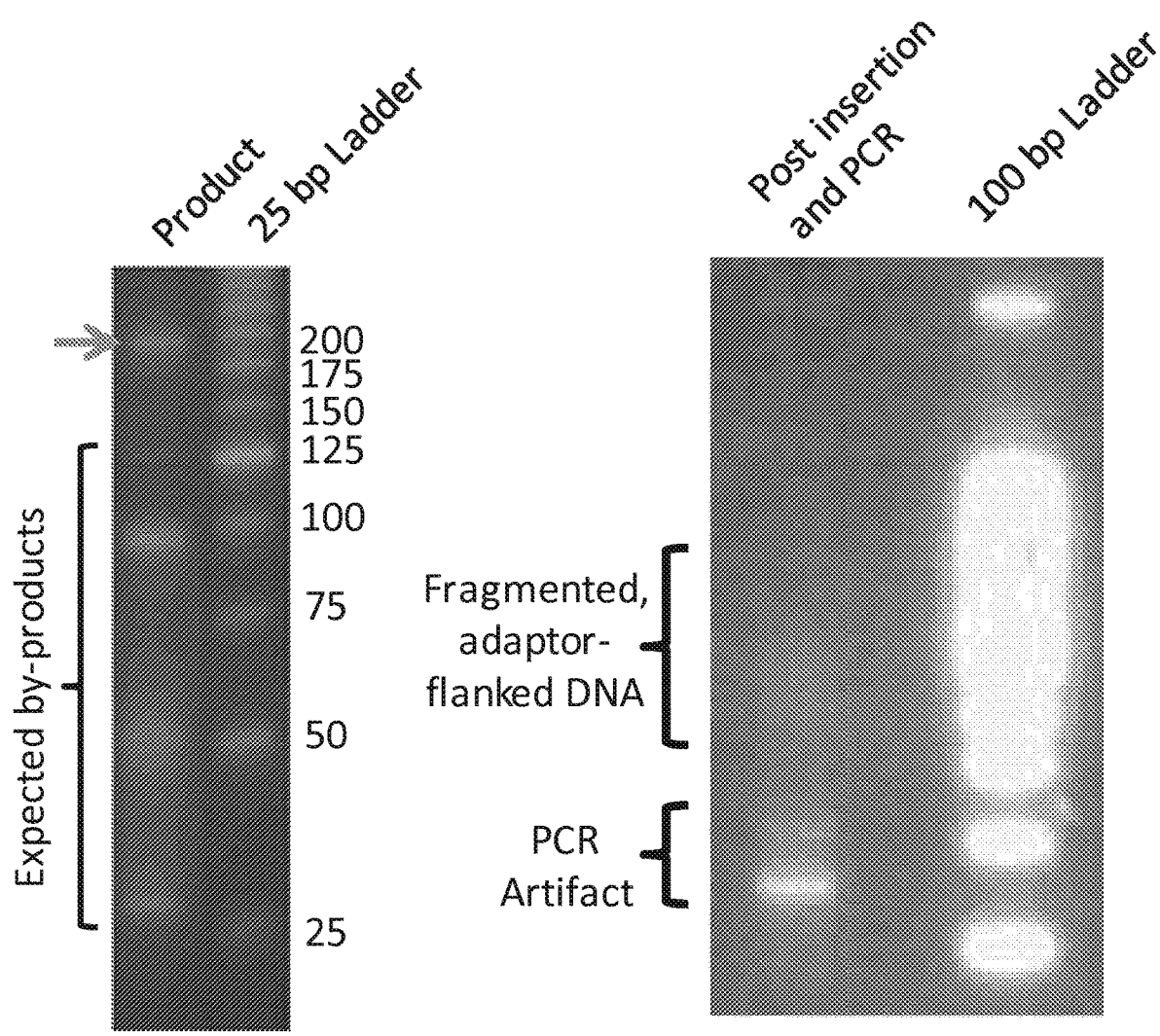
FIGS. 18A and 18B show species matching expected size (194 bp) of symmetrically tagged, 5'-5' adaptor (18A) and size distribution of post-transposition, post-PCR fragment amplicons is consistent with ~100-200 bp of genomic DNA and ~200 bp of total adaptor/barcode (18B).

The 5'-5' linked, symmetrically tagged transposon species was constructed as described. The full length product (194 bp) of said transposon, prior to gel purification to remove extension byproducts, is shown in FIG. 18A, Successful fragmentation of genomic DNA with said transposon is shown in FIG. 18B.

The success of this approach is dependent on at least two parameters: (1) Maintenance of library complexity: The chaining of read-pairs terminates when adjacent fragments on either end of a chain are undetectable in sequencing. For example, at the extreme, if 100% of fragments derived from synthetic transposition were successfully sequenced along with corresponding tags, then in principle it would be possible to chain from end-to-end of entire chromosomes. (2) Uniformity of representation: The extent of sequencing required to sample tags and primary sequences from both ends of a large fraction of fragmentation events is heavily dependent on library uniformity. Significant skewing of relative representation may require a correspondingly large amount of sequencing to overcome. It is therefore important that such skewing be minimized.

Figure 7:
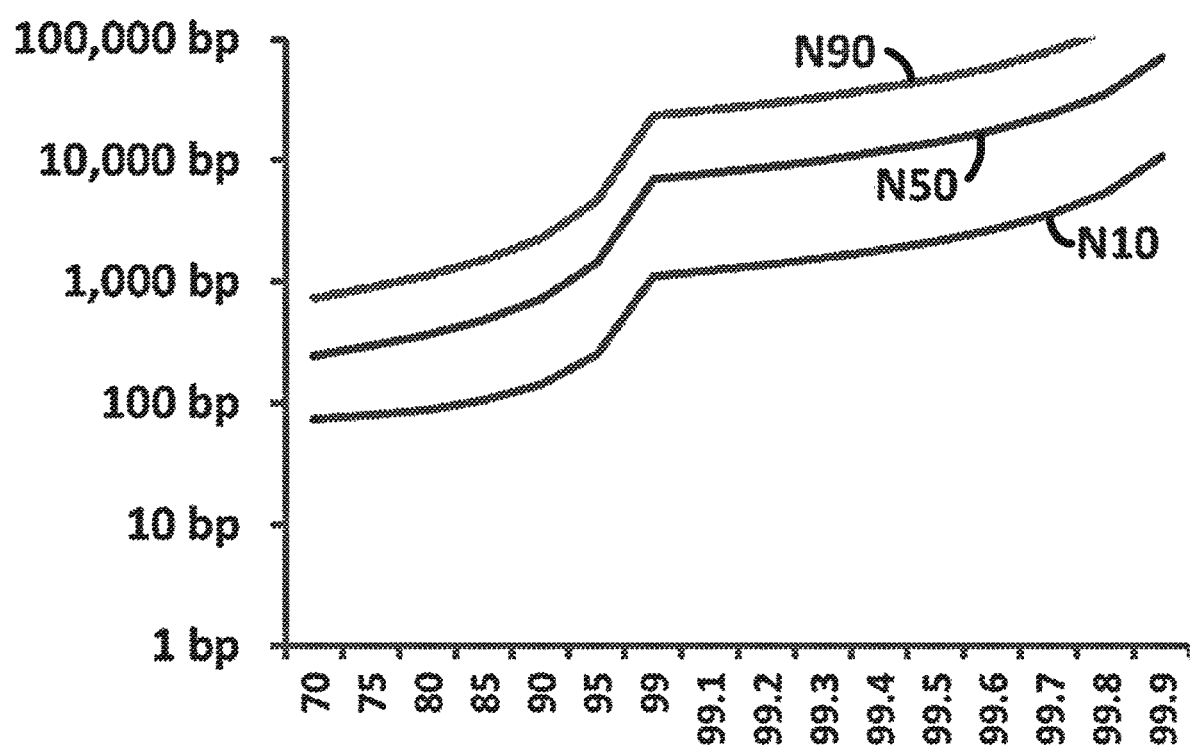
FIG. 7 is a graph showing the expected N10, N50, N90 lengths of the total span (y-axis) of chains of read-pairs that are identified as resulting from a contiguous series of fragmentation events along the same genomic DNA molecule, as a function of the efficiency of identifying individual 'joins' (x-axis, percentage; note transition in scale at 99%).

Through simulation, the N10, N50, and N90 span of chained read-pairs were determined based on the empirical size distribution of transposome fragmentation (FIG. 3 above) and as a function of the fraction of transposase-derived fragments that are successfully sequenced (which is in turn a function of sequencing depth and the above-described performance parameters). As shown in FIG. 7, contiguity rises sharply at efficiencies above 90%. At 95% efficiency, the N50 is 1.4 Kb and the N10 is 4.7 Kb. At 99% efficiency, the N50 is 8 Kb, and the N10 is 24 Kb. At 99.9% efficiency, the N50 is 71 Kb, and the N10 is 237 Kb.

An important aspect of this technology is that the in silico "joins" between independent read-pairs are almost completely independent of the primary sequence content (as would largely be the case with conventional de novo assembly, were it not confounded by the ubiquity of closely related sequences). Rather, joins are based on the shared barcode sequences which result from the synthetic transposons that are used to symmetrically tag fragmentation events. It is noted that 25 bp barcodes (which would only require a 25% increase in the amount of sequencing relative to a PE100 run) are unlikely to be identical by chance, even when sequencing millions of independent tags and allowing for a reasonable edit distance. Furthermore, the expected 9 bp overlaps between primary sequences can serve as a "verification key" for correct joins. Thus, the chance that coincidence or errors resulting in incorrect joins is very low.

This method may enable the equivalent of "strobe reads" (i.e., multiple sub-reads from a single, long contiguous fragment (Ritz et al. 2010)), while using a short-read technology. The gaps result when any given genomic fragment along the chain is too long to be spanned by single-end or paired-end sequencing. The frequency and length distribution of gaps is a function of the read-length of the short-read technology with which this method is integrated. For example, assuming that: 1) genomic fragments are interrogated by paired-end, 100 bp reads (PE100); 2) a terminal overlap of 20 bp is sufficient to merge read-pairs sequencing the same fragment from either end; 3) the fragmentation size-distribution shown in FIG. 3 holds, then simulations show an average of 0.7 gaps per Kb, with gap sizes averaging 53±48 bp (less than 5% of the overall scaffold length).

1.D. LoxP Insertion Via Transposase Followed by Cre Recombination

In another embodiment, the bacterial transposase Tn5 may be used to insert a transposon containing the 34 bp directional LoxP site flanked by inverted mosaic end (ME) sequences as well as an internal biotinylation and potentially alternate sequencing primers. Target insertion density is roughly one insertion event every 10 kilobases.

The resulting population of molecules has insertion events in the same order or in an inverted manner. Recombination with Cre recombinase will excise a 10 kb circular stretch of DNA where two LoxP sites were inserted in tandem in the same orientation. Where tandem LoxP sites are inverted, the 10 kb region will be inverted, yet the DNA will remain linear. Finally, inter-strand LoxP sites will recombine and swap strands which will also result in linear DNA.

Linear molecules may then be digested using a plasmid safe exonuclease, leaving behind the circularized DNA resulting from recombination between two tandem LoxP sites in the same orientation.

Circularized DNA may then be used for library preparation by any method and the DNA flanking the LoxP transposons can be enriched for by streptavidin bead pulldown. PCR followed by sequencing from either within the LoxP sites, or from the terminal ends of the molecules will yield ~10 kb mate paired reads.

1.E. Y-Transposons

In another embodiment, a Y-adaptor approach (FIG. 23) may be used in place of traditional transposase catalyzed adaptor insertion as a method for a library preparation where the resulting species are either A-B (50%), A-A (25%), or B-B (25%) where A and B are the two different adaptors and only 50% of the molecules are viable for sequencing.

In this case, Tn5 may be loaded with oligonucleotides complementary for the 19 bp mosaic end recognition sequence along with an extension of complementarity to provide a higher melting temperature followed by non-complementary single stranded DNA (ssDNA) adaptor overhangs of A and B'. Transposition will result in one of the adaptors (ME at the 3' end) being directly linked with the other remaining bound via hybridization.

Non-displacing polymerization and nick-repair may result in molecules where each insertion event can result in a viable sequencing amplicon.

Figure 23:
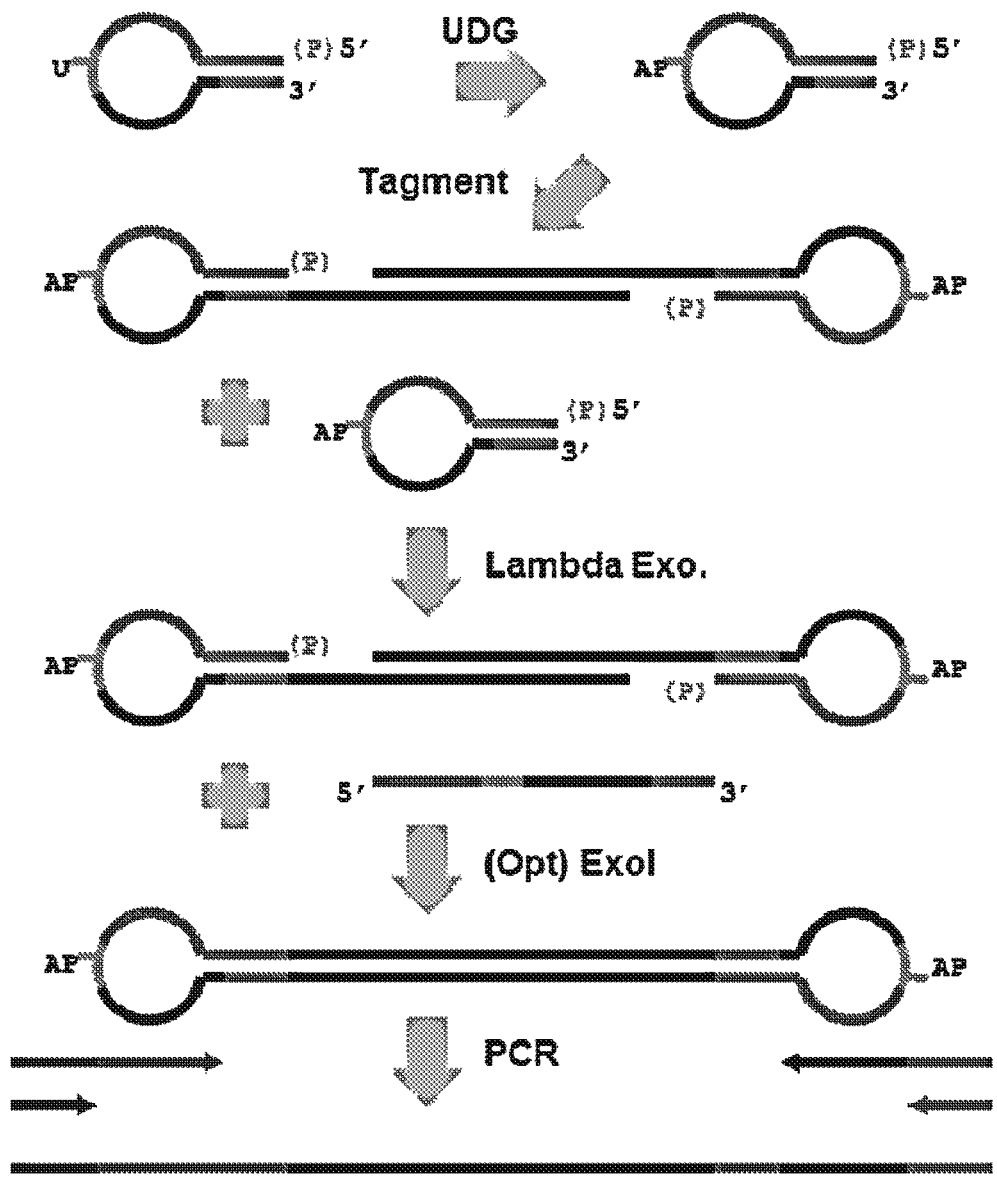
FIG. 23 illustrates a Y-adaptor approach for library preparation according to some embodiments.

An alternative embodiment involves a hairpin transposon containing a U (or other linker or targetable site for degradation or polymerase discontinuity) that links the ends of Y-adaptors to prevent loss of the other strand due to melting as in FIG. 23.

1.F. Double-Bubble Barcode Transposons

In another embodiment, a synthetic transposon containing two degenerate barcodes (on each strand) and two sets of primer sites as well as several restriction sites, can be inserted by high frequency into genomic DNA as shown in the example below:

ES-SbfI/AsiSI-N1/N2-Barcode-X/Y-NotI-X/Y-Barcode-N1/N2-SbfI/AsiSI-ES

The resulting transposition and gap-repair followed by whole genome amplification (WGA) resolves the degenerate regions. Digestion using the outermost restriction sites (SbfI, AsiSI in the example above) followed by PCR using N1/N2 and overhanging flowcell primers will allow for a sequencing run to associate the two degenerate barcodes within each inserted transposon.

The other digestion in the middle of the transposon (NotI in the example above) and amplification and sequencing from the X/Y as well as N1/N2 gives the outer barcode sequences and intervening genomic DNA.

1.G. Subassembly with Transposase Inserted Barcodes

In another embodiment, a discontinuous transposon may be inserted where each loaded DNA sequence is comprised of an outer flowcell primer, a degenerate barcode, an inner sequencing primer, and the double stranded transposase recognition sequence. The target insertion density may be every 1 to 2 kb.

After transposition, a degenerate sequence primer with a sequencing or flowcell primer overhang can be used to anneal to different positions along the molecule and extended back to the terminating transposase added sequence under dilute template or, more likely, emulsion conditions.

Sequencing will allow barcode association with every read that comes from the degenerate primer extension that occurred throughout the long molecule.

1.H. Mate-Pair (ssDNA Circularization) Transposase Based Library Prep

In another embodiment, a standard, barcoded transposase-based library prep with a fragment size of approximately 1 to 2 kb, wherein size selection may be required, may be used to form a mate pair library.

The large fragment barcoded transposase based library prep will be subject to PCR using 5' phosphorylated flowcell (outermost) primers, in which one also has an internal biotin as well as a uracil near the 5' end.

The resulting PCR product will be circularized, followed by mechanical shearing. The fragmented DNA is then denatured and circularized in a single-stranded manner. The fragments containing the ends of the initial circularization are selected for using a streptavidin coated bead. The circles are then made linear by digestion at the uracil which will flip out the molecule. Sequencing allows for mate pair reads from the ends of the original library, also preserving the barcode.

1.I. Transposon Modified Fosmid or Plasmid Library Pool Sequencing

Figure 27:
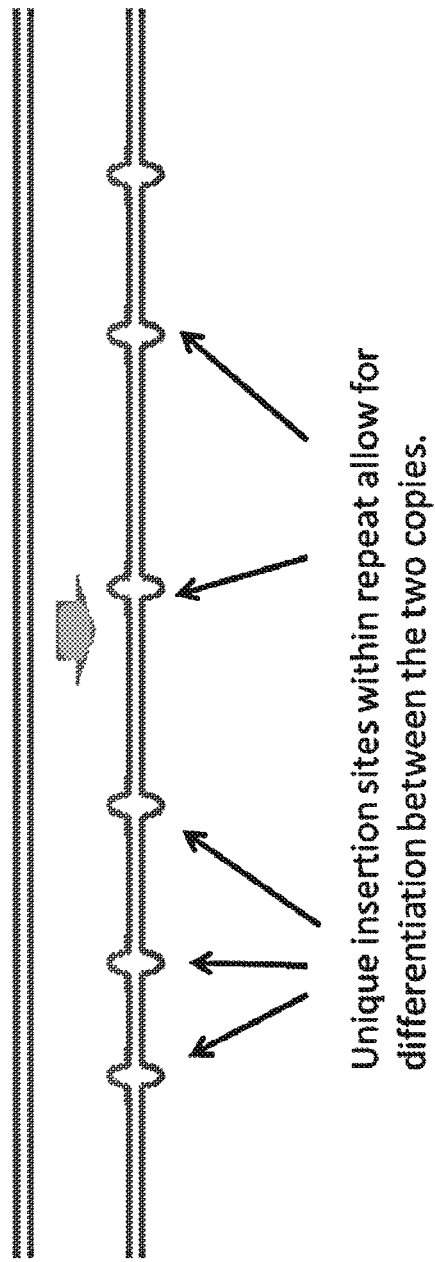
FIG. 27 illustrates a transposon-modified fosmid library pool approach to sequencing by using unique barcodes or insertion sites within repetitive regions according to some embodiments.

In another embodiment, continuous, synthetic transposons may be inserted into genomic DNA (gDNA), followed by gap repair. DNA is then sheared to 40 kb (or roughly 5 kb) and used to make a complex fosmid library (or plasmid) library respectively. This will allow for repetitive regions of the genome to be broken up by transposons that either have unique barcodes, or are identified by their unique insertion site into the repetitive region (FIG. 27).

Briefly, synthetic, continuous transposons are inserted into genomic or high molecular weight DNA using in vitro transposition methods to a density between 100 and 1000 base pairs (bp). Transposons are either all the same, or contain unique barcodes. Lesions 9 bp in length that result from the transposition mechanism are then repaired. Next, DNA is sheared to approximately ~40 kb (or ~5 kb) and a size selection is performed, followed by end-repair. Next, a complex fosmid (or plasmid) library is generated using the modified, sheared, and repaired DNA. Finally, fosmid (or plasmid) library pools are sequenced to provide phasing information as well as information regarding transposon insertions that will allow for differentiation between similar regions of the genome, using either unique barcodes and/or unique transposon insertion sites.

Example 2: Mid-Range Contiguity

2.A. Emulsion PCR with Droplet-Specific Barcodes

Figure 8:
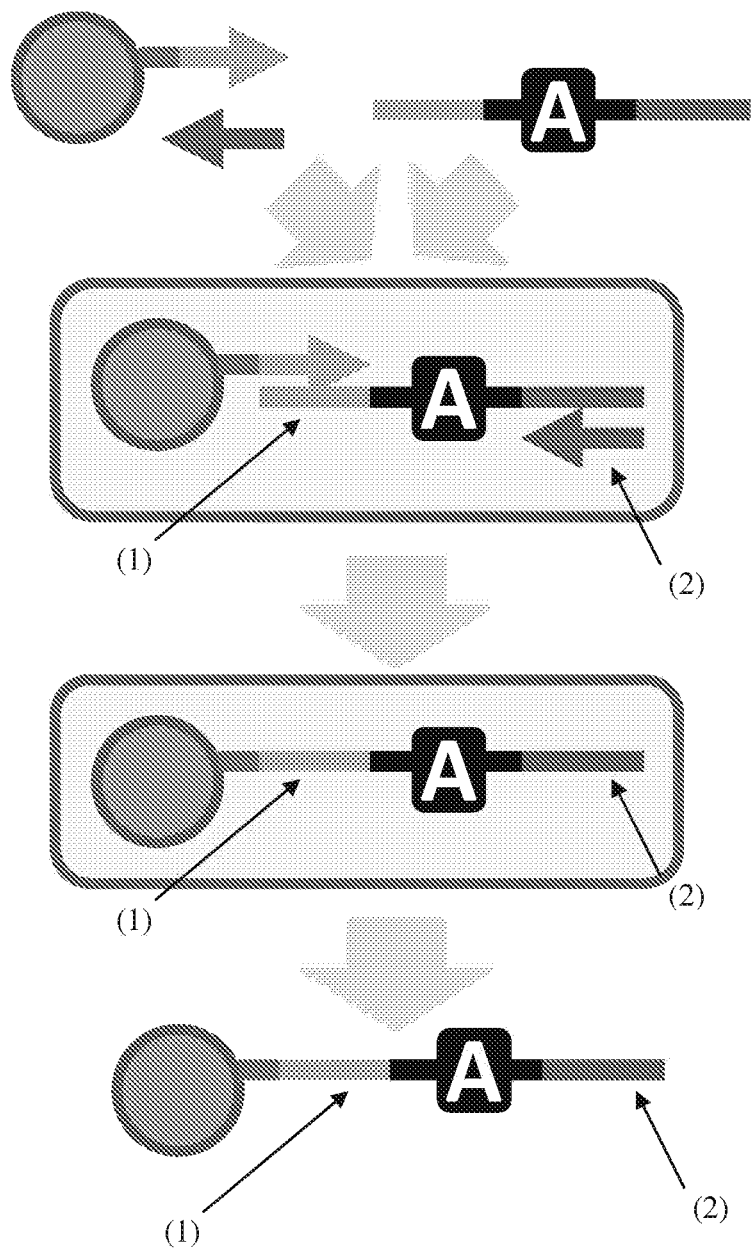
FIG. 8 is a schematic diagram showing that emulsion PCR of a template consisting of common regions ((1), (2)) that flank a degenerate region (A) generates clonally barcoded beads. The common 3' end of the bead-tethered strand (2) can itself serve as a primer in subsequent emulsion PCR reactions.

Emulsion PCR is well established, but the methods below require droplets containing reagents including primers with droplet-specific barcodes. These reagents can be generated through emulsion PCR of common sequences flanking a degenerate subsequence, with recovery of products to micron scale beads (FIG. 8) (Dressman et al. 2003). Specifically, large numbers of clonally amplified beads (each bearing a presumably unique barcode) may be generated by emulsion PCR with limiting dilution, followed by enrichment of "amplified" beads by hybridization (Shendure et al. 2005). These beads can be emulsified again for use in the below methods. Inclusion of a single clonally amplified bead per droplet, along with appropriate design of common sequences and emulsion PCR primers will result in the capture of barcoded amplicons to the beads themselves for convenient recovery.

2.B. Barcoding of "Pre-Transposed" HMW Genomic DNA

Figure 9:
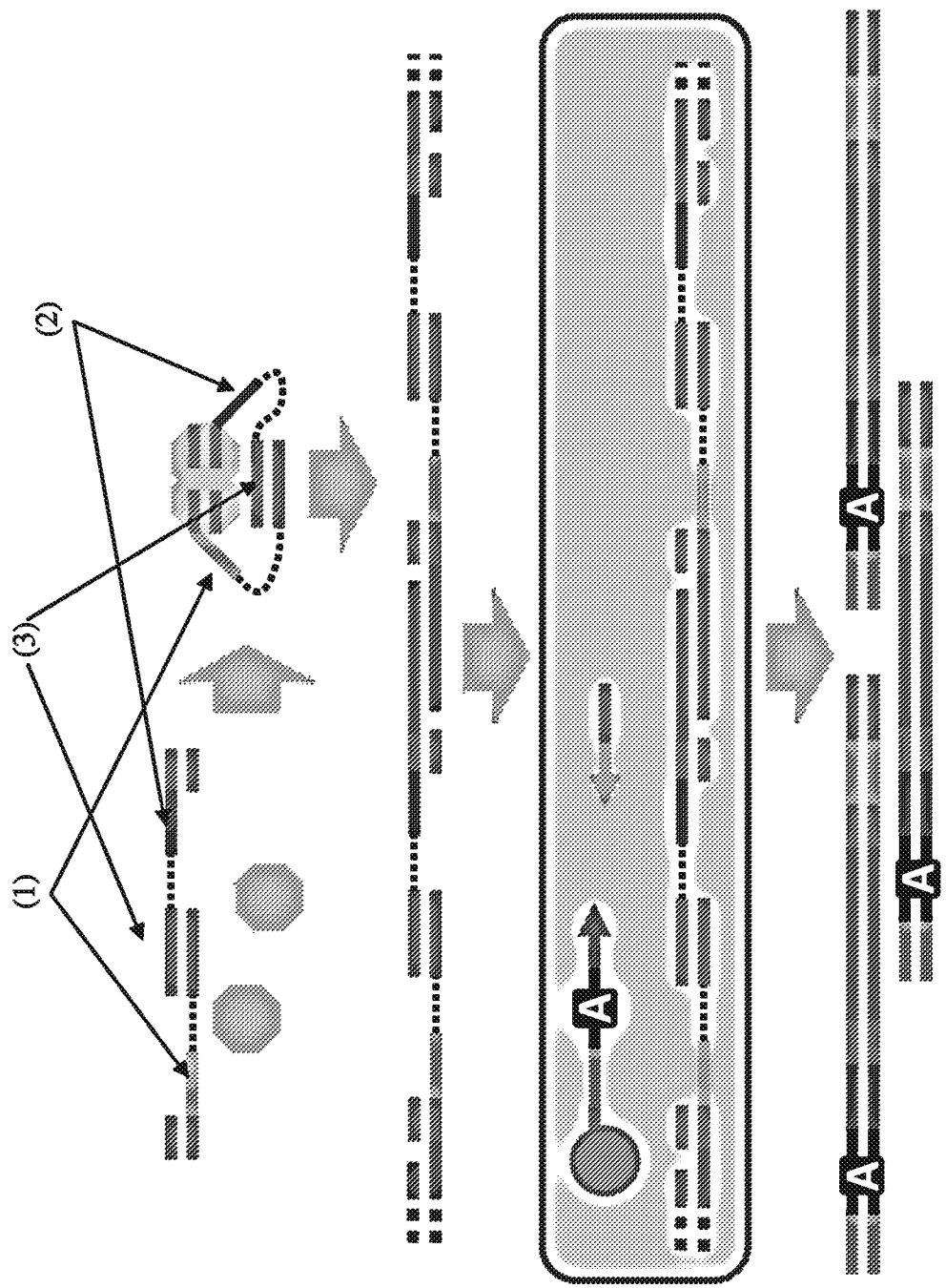
FIG. 9 is a schematic diagram showing HMW genomic DNA molecules (blue) that are subjected to in vitro fragmentation with transposomes bearing adaptors ((1), (2)) that are linked by hybridization of complementary subsequences (brown). DNA densely interspersed with these linked adaptors is then emulsified via microfluidics and subjected to emulsion PCR with primers bearing droplet-specific barcodes (A). Sequence reads from the same HMW genomic DNA fragment may be associated with the same barcode in the final library.

In one embodiment (FIG. 9), transposomes are loaded with adaptors containing the transposase recognition sequence with 5' ssDNA extensions of two different subsequences with complementary termini. This results in HMW genomic DNA densely interspersed with linked adaptor sequences. These "pre-transposed" molecules are then compartmentalized to emulsions with limiting dilution, using microfluidics to minimize shear and control size while maintaining a high throughput of droplet production (Zeng et al. 2010). Emulsion PCR, with primers bearing droplet-specific barcodes (2.A above), will amplify many fragments derived from the same HMW molecule within each droplet. Sequence reads derived from the same droplet will be associated with the same barcode in the final library, thereby facilitating the in silico grouping and localized assembly of each progenitor 20-200 Kb molecule.

2.C. Barcoding of "Pre-Amplified" HMW Genomic DNA

Figure 10:
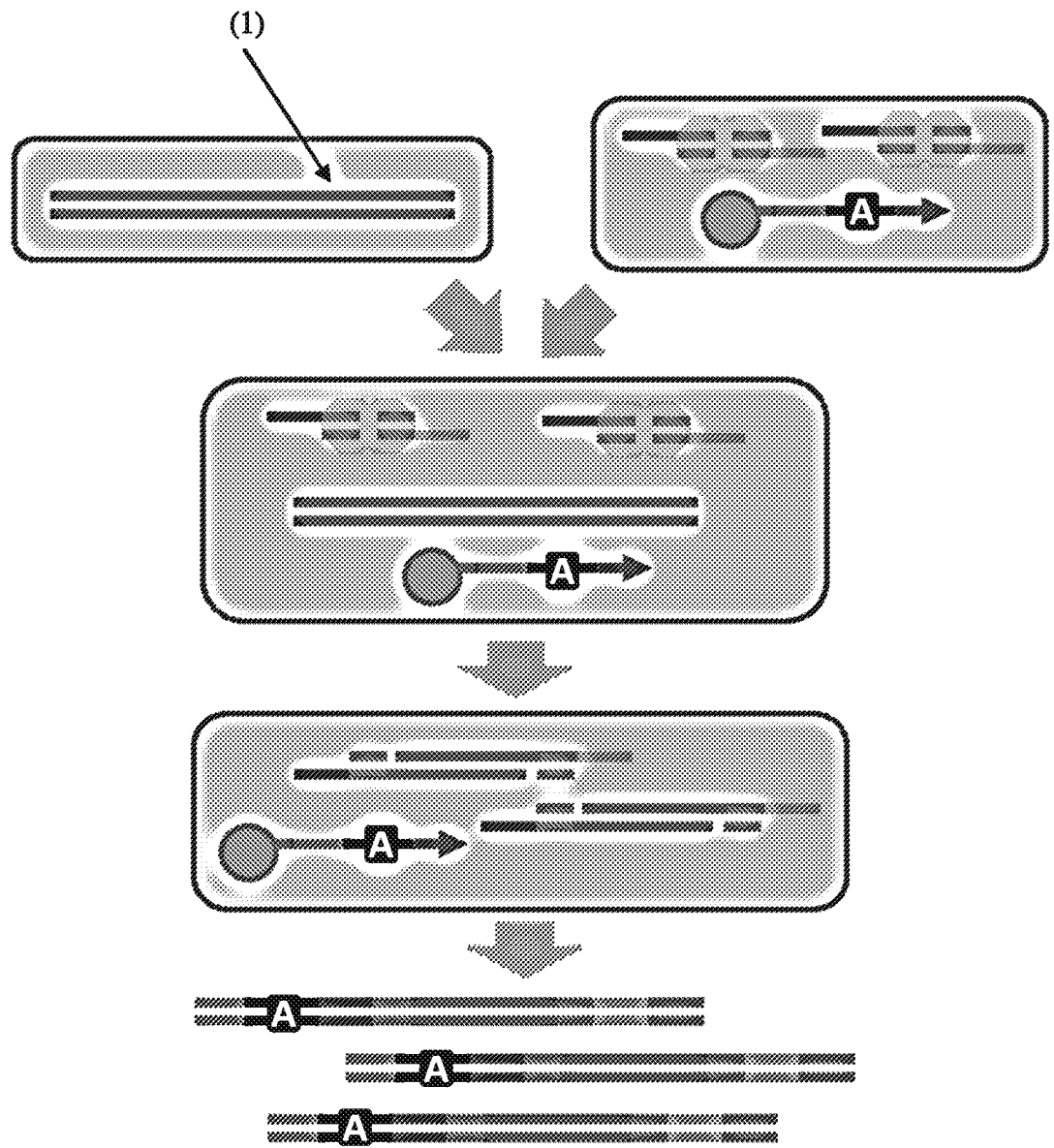
FIG. 10 is a schematic diagram showing emulsions that can be used to support the clonal, isothermal, multiple displacement amplification of HMW DNA (1). These are fused with droplets containing reagents for both transposome fragmentation and emulsion PCR with primers containing droplet-specific barcodes (color scheme identical to FIGS. 8 & 9).

In another embodiment (FIG. 10), HMW DNA is directly compartmentalized to emulsions, again using microfluidics to minimize shear, with reagents that support clonal, isothermal multiple displacement amplification (MDA) within droplets (Mazutis et al. 2009). These droplets will then be fused (with a relatively straightforward and cost-effective microfluidics device) with droplets containing standard transposomes as well as reagents for emulsion PCR, using primers bearing droplet-specific barcodes (2.A above). As with the previous embodiment described above, recovery and sequencing of the resulting library can interrogate both shotgun primary sequence and the barcode sequence on each molecule, with the expectation that reads sharing the same barcode derive from the same progenitor 20-200 Kb molecule.

This method may be used in transposome fragmentation followed by PCR within a single emulsion. When a "single-step" method is used to generate sequencing libraries from bacterial colonies, transposition may be performed followed by PCR with no cleanup step. In some aspects, the transposome reaction is diluted by addition of PCR reagents (Adey et al. 2010). Notably, in this method it is the PCR polymerase that facilitates the repair of the 9 bp lesion resulting from transposition by nick translation. At a minimum, these data illustrate that the MDA droplets can be fused with droplets supporting the transposome reaction, and these could subsequently be fused with larger droplets containing PCR reagents and barcoded primers.

Figure 19:
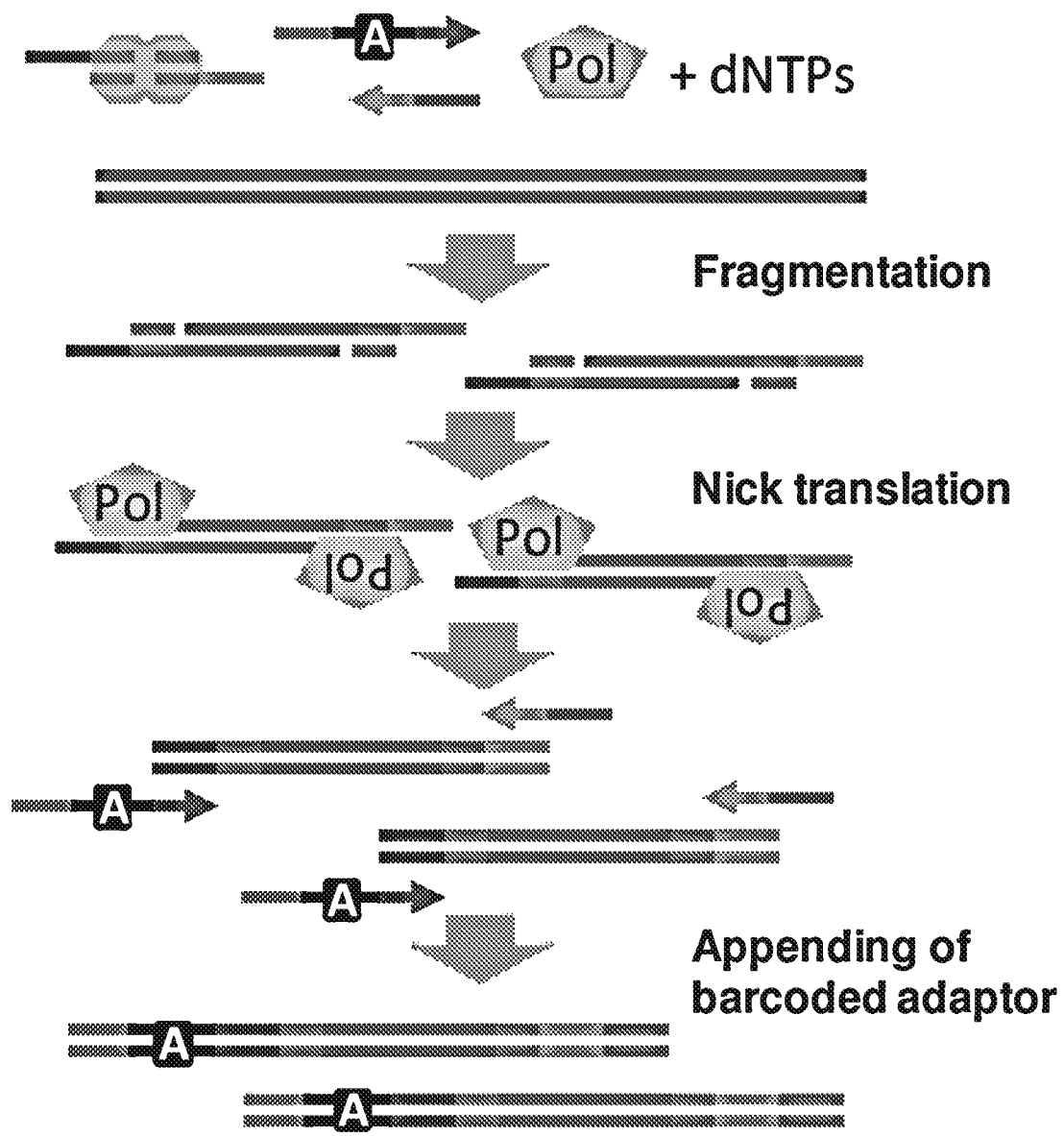
FIG. 19 illustrates transposition and polymerase extension in a single reaction volume with no intervening manipulations. Transposase drives fragmentation. Polymerase drives gap closure via nick translation and limited cycles of primer extension to append a barcode (A) bearing adaptor.
Figure 20:
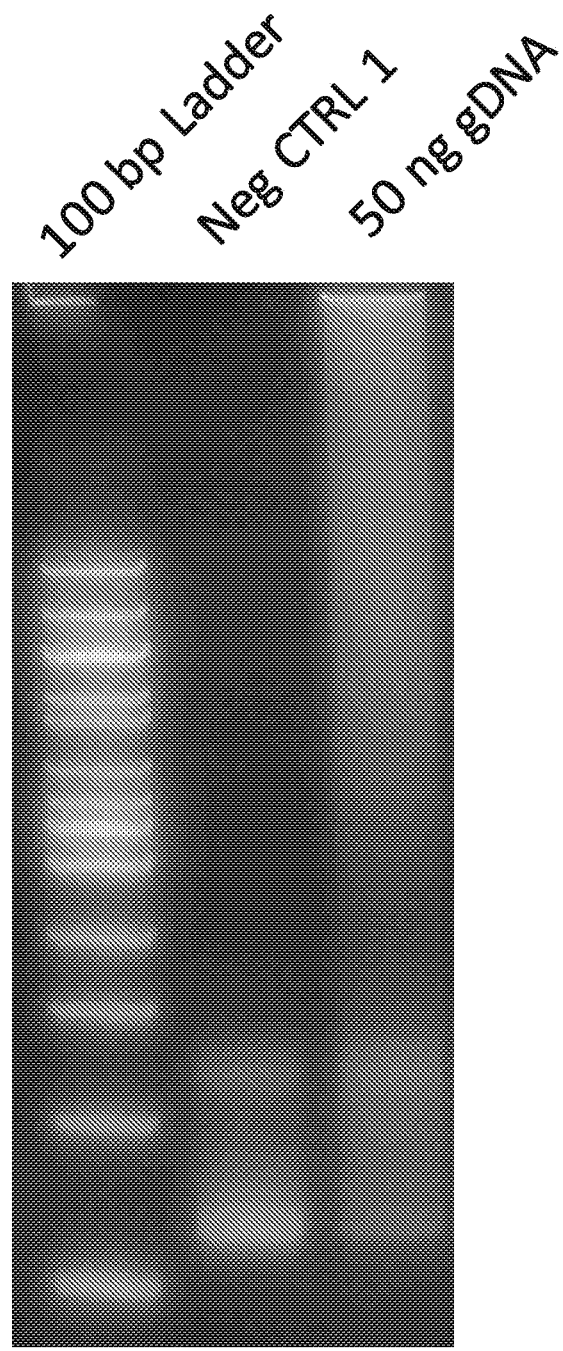
FIG. 20 illustrates transposition and polymerase extension in a single reaction volume with no intervening manipulations yields products that can be recovered by PCR after column-cleanup. The primers used in the PCR correspond to sequences added during the extension step. Lane 1=100 bp ladder; Lane 2=no genomic DNA (gDNA) control; Lane 3=50 gDNA input.

The same effective end-results may be achieved exclusively with in vitro methods. Each of the methods described herein (2.B, 2.C) are dependent on capturing transposome fragmentation products within each emulsion droplet to a uniquely barcoded bead. In order for one of these approaches to be successful (for example, the approach described in 2.C.; "barcoding" of "pre-amplified" HMW genomic DNA"), both transposase-based fragmentation and polymerase-based extension must take place within the same emulsion compartment, i.e. within the same buffer. Initial experiments have been focused on this specific step, and are being conducted in non-emulsion reaction volumes to facilitate optimization (schematic in FIG. 19). Recently, this compatibility in selected buffers was demonstrated. In brief, a reaction volume was prepared containing 50 ng of genomic DNA in Nextera HMW buffer, dNTPs, adaptors 1 & 2, loaded transposase, and PCR polymerase. Adaptors 1 & 2 were designed to include both sequences complementary to the synthetic transposons, as well as unique sequences at their 5' ends (P1 & P2). The transposase+ extension reaction was carried out at 55 C for 5:00 to facilitate transposition, followed immediately by a single round of thermocycling to facilitate the nick translation and to append adaptors 1 & 2 (72 C for 10:00, 95 C for 0:30, 62 C for 0:30, 72 C for 10:00). Reactions were subjected to column-based cleanup and then used as template in a PCR using only outer primers P1/P2. The resulting distribution of amplicon sizes (FIG. 20) is consistent with transposase-based fragmentation and polymerase extension taking place in the same buffer, albeit with limited insertion density. This reaction may be demonstrated it in the context of a water-in-oil emulsion, capture of extension products or beads loaded with barcoded oligonucleotides.

Mid-range contiguity information is likely sufficient to extensively support haplotype resolution in the resequencing of an individual human genome. To test this, a straightforward "short-cut" scheme was implemented by barcoding and sequencing complex pools of large-insert (fosmid) clones. Specifically, randomly sheared human genomic DNA (~35 Kb) was cloned from a single individual to yield a complex fosmid library (>2×10^6 clones). This library was then transformed to cultured *E. coli*. The resulting transformed *E. Coli* cultures were split into 115 fractions, and selected for transformants. The initial transformation was titrated to yield 5,000 clones per pool. Given the uniform insert size of ~35 Kb, this corresponds to ~3% physical coverage of a diploid human genome per pool. Transposome fragmentation was then performed to generate a barcoded library from each of the 115 pools. This library was sequenced across 18 lanes on the Illumina GA2x for a total of 120 Gb of sequence (PE76 or PE101+barcode). A shotgun library from this same individual was also sequenced across 7 lanes on the Illumina HiSeq for a total of 86 Gb of sequence (PE50), or 28-fold coverage of the haploid genome. The latter data alone yielded 3.6 million SNP and indel calls, but as with all individual human genome sequences to date, these calls are blind to haplotype.

After deconvolving barcodes and mapping reads, the approximate boundaries of individual clones within each pool were easily identified by read-depth. A total of 538,009 clones (4678±1229 per pool) for ~3× physical coverage of the diploid genome were identified. 98.6% of the genome was covered by 1+ clones, and 93.6% by 3+ clones. Long outgrowths of clone pools were avoided to minimize the impact of growth effects on representation. This was successful, as on average 82% of clones per pool had read depth within one order of magnitude. Because each pool only sparsely samples the genome as a whole, the rate of overlap, or 'clone-collision' within any given pool is low. Therefore, short reads derived from each pool overwhelmingly represent alleles from only one of the two homologous chromosomes at any given location. Haploid genotype calls from clones were assembled across all pools using a parsimony-maximization approach (Bansal & Bafna 2008). The resulting haplotype assembly covered 93% of ascertained heterozygous SNPs, with an N50 of 386 Kb. Of all RefSeq genes, 63% were entirely encompassed by a single phased haplotype block, while 75% were at least half encompassed by a single block.

Figure 11:
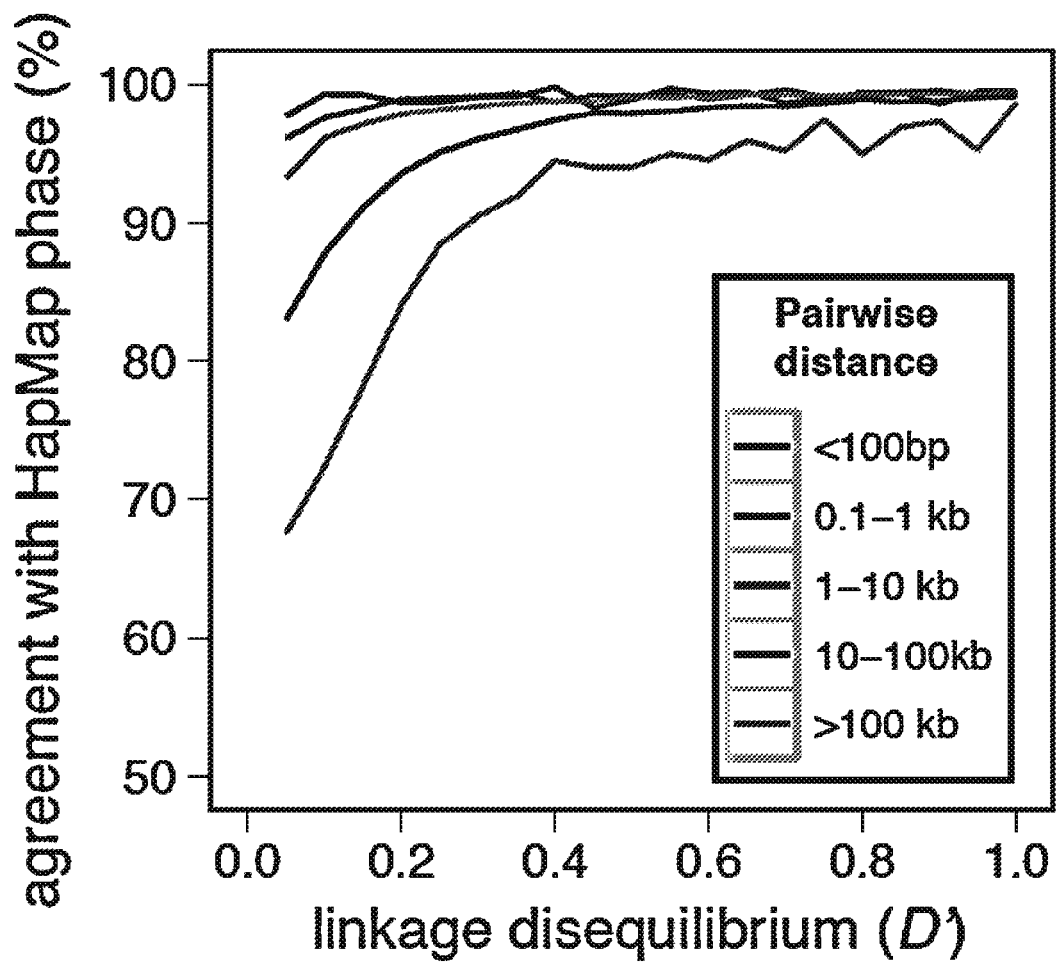
FIG. 11 is a graph showing a comparison of experimentally phased assembly with population-based HapMap predictions by HapMap for the same individual for various LD values. In contrast with HapMap inferences, the experimentally phased haplotypes are derived by a method that is LD independent, such that discrepancies predominantly reflect errors in inference-based haplotypes.

This phased assembly was compared to HapMap predictions for this same individual (FIG. 11). Within regions of exceptionally high LD (D'>0.90), a nearly perfect concordance with HapMap predictions was observed (>99.5% agreement). Because the sample chosen was not part of a trio, HapMap predictions rely upon LD between alleles to predict phase from genotype calls. Correspondingly, concordance was reduced to ~71% in more highly recombinogenic regions (D'<0.10), which includes the majority (66%) of pairwise SNP combinations. The haplotype-resolved resequencing of this genome is direct and experimental, and therefore completely orthogonal to population-based measures such as LD and allele frequency. Consequently, this trend likely reflects errors on the part of HapMap phasing (Lecy et al. 2007).

In contrast with population-based inferential methods, direct haplotyping allows for phasing of rare alleles and structural variants, including at complex, duplicated loci (Kidd et al. 2008). For instance, in these data, clones containing a common inversion polymorphism on chromosome 7q11 were observed as well as clones containing a rare deletion polymorphism on chromosome 1p36. Similar approaches may be used to leverage the unambiguous assignment of short sequence reads to 20-200 Kb regions by the methods described herein. Whether relying on clones, or entirely in vitro, mid-range contiguity information facilitates the long-range haplotype resolution of individual human genomes. Further, mid-range contiguity information may also facilitate the de novo assembly of large, complex genomes.

2.D. Emulsion Transposition with Bead-Immobilized Transposomes

In another embodiment, beads coated in a primer flanked, degenerate, monoclonal barcode oligonucleotide (or "oligo") terminating in the double stranded DNA (dsDNA) transposase recognition sequence and beginning with a flowcell primer may be emulsified with high molecular weight genomic DNA and free transposase. The bead-immobilized oligos and attack genomic DNA may be loaded within the emulsion the transposase. Resulting fragments are PCR ready and able to be sequenced along with their barcode. Barcode association can then be used to group reads that came from the same progenitor molecule.

This approach encompasses several variants. For example, many clonal copies of a barcoded oligo ending in the mosaic end sequence (ME) are immobilized at their 5' ends on each bead. These beads may be generated by emulsion PCR with 5'-biotinylated primers and a degenerate region, or alternatively a smaller set of barcoded oligos may be synthesized and immobilized to the beads. A short oligo comprising the reverse complement of ME (ME') is present in the emulsion mix to support transposase loading. Alternatively, the ME' may be annealed and loaded onto transposases prior to emulsification. Bead-bound oligos may be designed with an enzymatically cleavable moiety to allow the loaded transposomes to diffuse within the droplet.

2.E. Emulsion Transposition and Bead Capture

In another embodiment, beads are coated by oligos with an internal, inverted base, thereby having two 3' ends. On the bead-distal 3' side of the inverted base is a primer site flanked, degenerate, monoclonal barcode, and a fixed adaptor sequence ("N1 prime"). These are emulsified with substrate (e.g., HMW gDNA) and transposase pre-loaded with oligos 5'-N1-ME. Transposition then proceeds within each droplet, generating fragments covalently linked to the 5'-N1-ME sequence. The mixture is then heated, inactivating the transposase enzyme and denaturing the fragmented substrate. After slowly cooling, 5'-N1 flanked fragments generated by transposition anneal to the free ends of bead-bound oligos. Bead bound oligos are then extended using a thermostabile polymerase either present in each droplet, or after breaking the emulsion. Barcode association is then used to group reads originating from the same progenitor molecule.

In an alternatives approach, beads are coated in a primer flanked, degenerate, monoclonal barcode oligo. Then, a pool of random hexamers (DNA or LNA) having a 3'-blocking moiety is attached to the 3' end of each bead-immobilized oligos by ssDNA or RNA ligase. Beads, substrate (e.g., HMW gDNA) and pre-loaded transposomes are then emulsified. Transposition results in fragments with covalently attached 5' linkers. These fragments are denatured and allowed to anneal to the random 3' portion of the bead-bound oligos. The hybridized fragments are then extended into the barcode either by polymerase present in each droplet or by breaking the emulsion and adding polymerase. Barcode association is then used to group reads originating from the same progenitor molecule.

2.F. End Capture of Long Molecules Using Transposase and Emulsification

In another embodiment, long genomic DNA molecules with an adaptor B' ligated to the ends may be subject to transposon insertion of a bubble transposon in which inverted adaptor A sequences make up the bubble which is flanked by transposon recognition sequences. The molecules may then be emulsified where a portion of microreactions contain a large molecule, a bead coated in a monoclonal degenerate barcode terminating in adaptor B, and adaptor A. Performing PCR is then performed, which results in amplification of the outer most ends with the ligated B adaptors on the bead, appending the unique barcode.

After performing a subsequent PCR using the washed beads, the library may be sequenced and barcodes may be used to associate the two end sequences from each of the ends of the original long molecule, effectively creating a jumping library of whatever size the original long molecules were.

2.G. T7 Promoter Insertion Via Transposase

In another embodiment, transposomes are loaded with a bubble structure, flanked by a T7 terminator to one side and a T7 promoter to the other. This structure is integrated into a substrate (e.g., HMW gDNA) by bulk transposition at a density of at least one integration per kilobase. The resulting material is then emulsified with T7 RNA polymerase and with beads containing monoclonal degenerate barcodes flanked by priming sites and ending in sequence (X) complementary to the portion of the integrated bubble structure preceding the T7 terminator. In vitro transcription is carried out within each droplet, and the resulting RNA molecules, ending in X', hybridize to their bead-bound complementary sequences. Reverse transcription is then carried out to extend the bead-bound oligos, either within each droplet or after breaking the emulsion. Barcode association is then used to group reads originating from the same progenitor molecule.

2.H. Extension of Emulsion PCR on Adaptor Bubble Inserted High Molecular Weight Fragments to Allow for Subassembly In another embodiment, a transposon that forms a "bubble" may be inserted, wherein the bubble within the transposon includes two of the same adaptors in reverse orientation. Using the same adaptors in reverse orientation maintains the "bubble" structure. Bubbles may be inserted at a frequency of approximately 1,000 bp.

Figure 26:
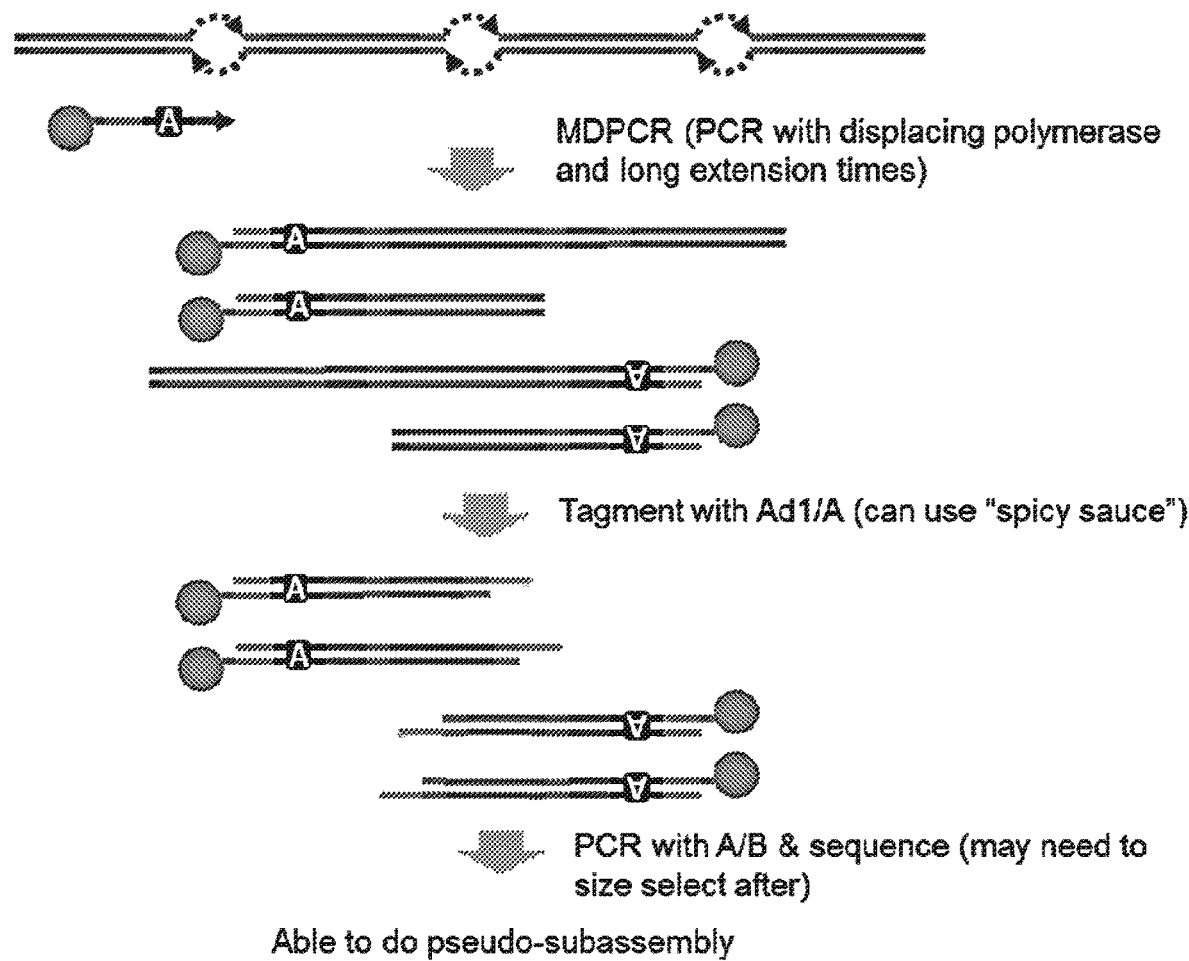
FIG. 26 illustrates a method of transposon insertion using two of the same adaptors in reverse orientation to maintain the resulting "bubble" structure followed by emulsification and amplification according to some embodiments.

As shown in FIG. 26, large fragments will then be emulsified where a portion of the microreactions will contain a single, long DNA fragment, a single bead coated in a primer bound via biotin at its 5' end and consisting of an outer primer, a degenerate barcode (monoclonal for each bead), and the complement to the adaptor inserted via transposition. Multiple displacing PCR (MDPCR) then generates many copies extending out from each adaptor insertion site.

Emulsions are then broken and beads are pulled out. Transposition with a second adaptor on a discontinuous transposon will occur at random distances away from the bead for each copy of the amplified fragment. Removal of non-bead bound products and amplification will produce a library in which all amplicons from a large fragment can be associated with one another. The library also retains the ability to use the sequence acquired by sequencing genomic DNA from the original barcode adaptor as an anchor to associate reads where the paired read for all locally associated reads can be used for subassembly, as they arise from different secondary (post emulsion PCR) transposition events.

2.I. Clonally Barcode-Tailed, Randomly Primed Amplification in Nanoliter Reactors In another embodiment, beads are coated in primer sequences, or templates thereof, having a degenerate barcode monoclonal for each bead as well as a non-clonal, fully degenerate short kmer (k=5 to 9). These primers are released by excision of the immobilized DNA oligo from the bead, or alternatively by in vitro transcription of the immobilized DNA oligo into RNA primers. Oligos immobilized on the beads are designed such that the resulting DNA or RNA primers are structured as follows:

5'-[common1]-[clonal barcode]-[common2]-[random_k-mer]-3'OH

Bead-immobilized oligos may be prepared either by directly immobilizing these full sequences (e.g., in sets of 96 different barcodes) to beads, or by emulsion PCR.

Beads thus constructed are emulsified with: (i) substrate DNA (e.g., high molecular weight genomic DNA) at a target concentration of one substrate fragment per droplet, (ii) reagents for primer release/synthesis including, but not limited to, T7 RNAP and NTPs, any suitable restriction enzyme, or uracil N-glycoslyase and DNA glycosylaselyase, and (iii) reagents to support DNA polymerization from the cleaved/synthesized primers (e.g., phi29 or Bst DNA polymerase, dNTPs).

Following their release or synthesis, primers anneal by random priming to sites throughout the substrate molecule. The included DNA polymerase extends the annealed primers along the template, resulting in multiple, randomly spaced dsDNA fragments containing at the 5' end a tag clonal to a given droplet, and the 3' end sequence derived from various points along the substrate. In one aspect, the DNA polymerase has strong strand displacement activity (e.g., phi29 DNAP).

Following this DNA polymerization, the emulsion is broken. If RNA primers were used, the barcode encoded in each primer is reverse transcribed into DNA by methods known in the art. Finally, the resulting fragments are subjected to a standard library construction technique (transposase-based or otherwise) and amplified using a left primer consisting of common1 and a right primer corresponding to the adaptor added by transposition or ligation. Barcode association can then be used to group reads that came from the same progenitor molecule.

Example 3: Long-Range Contiguity

Methods for long-range contiguity, (e.g., 100 Kb-10 Mb) by in situ transposition into very HMW genomic DNA on the surface of a sequencing flowcell are developed using spatial information (i.e. the relative coordinates at which physically linked sequencing templates are immobilized), as opposed to capturing contiguity information to barcodes as described above.

Such methods are accomplished by (1) exploiting in situ transposition to obtain paired-end reads from arbitrarily large single DNA molecules, and (2) developing related methods whereby multiple reads along the full length of arbitrarily large single DNA molecules are obtained.

In one approach (FIG. 12B), HMW DNA molecules may be end-modified with an adaptor (FCA1), but are then hybridized to the flowcell without stretching. Long DNA molecules typically adopt a random coil configuration in solution. One end hybridizes, while the other end is spatially confined to an area proportional to the square root of the contour length of the template. This increases the probability that it will also hybridize at a close or nearly identical physical location (or a "constrained" physical location). The immobilized templates are then subjected to in situ transposition with transposomes loaded with hybrid adaptors corresponding to the second flow cell primer (FCA2), but also containing sequence corresponding to one of two possible sequencing primers (p1 or p2). After cluster PCR, approximately ~50% of the original templates will likely produce two visibly overlapping or closely located clusters that each contain shotgun sequence derived from one or the other end of the very HMW molecule adjacent to either p1 or p2. Reads originating from p1/p2 with the same or closely located physical coordinates are highly likely to have been derived from the ends of the same very HMW molecule.

For this approach (FIG. 12B), the molecules should have 3' single-stranded tails that are complementary to one of the flow-cell sequences (i.e. the cluster PCR primers). To achieve this, flow-cell adaptor A (or B) may be appended to the ends of HMW DNA molecules in solution, and then inserting adaptor B (or A) via in situ transposition. In practice, two different species of the adaptor are needed for one of these steps, i.e. A1 and A2 (or B1 and B2). This is because clusters derived from fragments at either end of any given HMW DNA molecule will be located in close proximity, with the potential to interfere with the sequencing of the other unless different sequencing primers are used. This can be achieved by using two different adaptors (i.e. A1 and A2 (or B1 and B2)) that both contain the flow-cell adaptor sequence (A (or B)) but also contain unique sequence at their 3' end to facilitate the design of distinct, non-cross-hybridizing sequencing primers. In one embodiment, A1 and A2 were added to the ends of HMW DNA in solution, and B via transposition. This scheme enables the sequencing of the HMW molecule ends (adjacent to A1 and A2), rather than the transposition junction (adjacent to B). The transposition junction necessarily includes the 19 bp mosaic end (ME) sequence, which complicates the design of two sequencing primers with distinct specificities. However, the alternative (sequencing through the 19 bp ME), would be unnecessarily wasteful.

It is noted that optical mapping is routinely used to analyze molecules as long as 1 Mb. The system described herein may be applied to molecules of similar lengths.

In another approach, optical sequencing on stretched single DNA molecules has been shown to be capable of yielding up to 3 bp of contiguous sequence information from multiple locations along the same molecule (Ramanathan et al. 2004). Since reads are generated directly from single molecules, issues of sample quantity and PCR bias are largely avoided. However, in order for this approach to be practical in facilitating de novo genome assembly, read-lengths must be significantly improved.

Here, in situ transposition may be used to facilitate methods related to optical sequencing but with existing next-generation sequencing hardware, software, and reagents. In one approach (FIG. 12A), a library of very HMW DNA molecules ($10^5$-$10^7$ bp) are end-modified with an adaptor (FCA1), hybridized to the surface of a primer-coated flowcell, and physically stretched using an electric field. While the field is still applied, a second adaptor is flushed into the flowcell and allowed to hybridize (similar to (Geiss et al. 2008)). This locks down the free end of every template and holds it in a stretched position. Transposomes pre-loaded with a second flowcell compatible adaptor (FCA2) can then be introduced to randomly fragment the stretched molecules while simultaneously inserting these adaptors. The majority of fragments will receive two FCA2 adaptors, except for the ends, which have both FCA1 and FCA2. Cluster PCR via these adaptors will only produce clusters at the ends of the stretched molecule. In this way, we obtain spatially co-linear clusters that are known to be derived from the same parent molecule and are related by the physical distance between the clusters.

3.A. Optical Sequencing & In Situ Library Construction

Optical mapping using restriction enzymes has been successful in generating long-range contiguity maps for genome assembly (Zhou et al. 2009; Zhou et al. 2007; Lin et al. 1999; Lim et al. 2001; Lai et al. 1999; Schwartz et al. 1993). However, this process is limited by false positive and negative cut sites due to star activity and inefficient cleavage, necessitating multiple optical maps from the same region to generate a consensus map. The non-uniform distribution of restriction enzyme recognition sites can also limit the amount of useful information derived from repetitive or low complexity regions.

As discussed above, the relatively short read lengths associated with the most cost-effective DNA sequencing technologies have limited the quality and completeness of de novo genome assembly as well as of human genome sequencing. There are currently few or no robust methods that capture mid-range and long-range contiguity information at a throughput commensurate with the current scale of massively parallel sequencing. To address this limitation, an in situ library was constructed and optical sequencing was performed on the flow-cells of currently available next-generation sequencing platforms. This produced an efficient method of capturing both contiguity information and primary sequence with a single technology by generating >30,000 E. coli paired-end reads separated by 1, 2, or 3 kb using in situ library construction on standard Illumina flow-cells.

Surface-mediated bridge PCR performs poorly for inserts >=1 kb which limits the Illumina platform's ability to generate native long paired end reads from high molecular weight (HMW) DNA. To circumvent this, HMW DNA molecules constrained to a specific size-range are end-modified with two flowcell-compatible adaptor sequences (FCA1 and FCA2), each of which contains one of two possible priming sequencing primers (p1 or p2). The templates are then hybridized to the flowcell surface under stationary flow, during which they typically adopt a random coil configuration. When one template end hybridizes, it spatially confines the other template end thereby increasing the probability that it will also hybridize in close physical proximity. The immobilized templates are subsequently subjected to in situ transposition with transposomes loaded with hybrid adaptors corresponding to the second flow cell adaptor (FCB1). Without a transposition event, each template molecule contains only one of the two required flowcell adaptors required to generate a cluster. For templates that are transposed, this process generates two low molecular weight (LMW) templates that are both capable of cluster formation and hybridized to the surface in close proximity. After bridge PCR amplification, 50% of the templates should produce two overlapping or closely located clusters that each contain shotgun sequence derived from one or the other end of the HMW molecule. p1 is then serially used to sequence one end and p2 to sequence the other end of the template, and reads originating from closely located physical coordinates are likely to have been derived from the ends of the same HMW parent molecule. In this way, the information provided by the spatial coordinates at which clusters are generated to infer long-range contiguity. In a similar way, HMW DNA molecules that are tethered at one end and stretched using flow or an electric field could be transposed in situ with appropriate adapters to generate multiple co-linear clusters derived from the same parent molecule.

Materials and Methods

Library Synthesis.

Genomic DNA from Eschericia coli type B cells were obtained from USB (Part #14380) and physically sheared for 30 sec on a Bioruptor (Diagenode). The DNA was then size selected on a 1% agarose gel run at 100V for 2 hours, purified (Qiagen QIAquick Gel Extraction Kit), and end-repaired (End-It, Epicentre). Hairpin adapters were self annealed and then blunt-ligated using Fast-Link Ligase (Epicentre) overnight. Unligated genomic DNA and adapters were removed with treatment by Exonuclease III (NEB) and VII (Epicentre). The molecules were then treated with Uracil-specific excision reagent (USER™) (NEB) to generate single-stranded flow cell complementary 3' tails.

Transposome Loading.

Synthetic DNA oligonucleotides containing transposase mosiac, primer sites, and flowcell adapter sequence were obtained from IDT. Adapters were annealed and loaded on the transposase (Tn5, Epicentre) by mixing and incubating at room temperature for 20 minutes.

In Situ Flowcell Library Construction and Sequencing.

A custom cluster generation protocol was written to accommodate template and transposome loading on a standard Illumina Cluster Station. The flowcell was first primed with hybridization buffer and then heated to 96° C. at rate of 1° C./s. At 96° C. a standard Illumina sequencing library was loaded into a separate lane as a control while the other seven lanes received hybridization buffer. After a 2 min. incubation, the temperature was lowered to 65° C. at 0.05° C./s to hybridize the control library. At this point, the tubing on the manifold for the control lane was removed on both the input and output sides of the flowcell. The E. coli libraries were added to each lane at 15 µL/min for 2.5 minutes, followed by slowly cooling the flowcell to 40° C. at 0.02° C./sec. After a 5 min. incubation, the flowcell was heated to 55° C. at 1° C./s. Loaded transposomes were then added to the lanes containing E. coli at 15 µL/min. The flowcell was incubated at 55° C. for 5 minutes to allow transposition to take place and then cooled to 40° C. A new manifold was then installed on the cluster station and Illumina wash/amplification buffer was injected across the entire flowcell. First strand synthesis was performed at 65° C. for 5 minutes and 74° C. for 5 minutes using library-specific DNA polymerases. Standard human control libraries were than hybridized to each E. coli lane as per the manufacturer's protocol. Clusters were generated with 35 cycles of bridge amplification. Two separate single end 36 bp (SE36) reads were obtained on an Illumina Genome Analyzer lix with RTA 1.8 and SBS v5 as per the manufacturer's protocol.

Data Collection and Analysis.

The X-Y coordinates of every cluster from read 1 and read 2 were extracted from the fastq files using a custom Perl script. This data was used to calculate the image offsets using the normxcorr2 function in MATLAB and the X-Y coordinates for read 2 were corrected accordingly. Reads were then mapped separately to the E. coli genome using the Burrows-Wheeler Aligner (BWA) and the identities of neighboring clusters between read 1 and read 2 were determined using a custom Perl script.

Results

In Vitro and In Situ Library Construction and Sequencing.

Figure 31A:
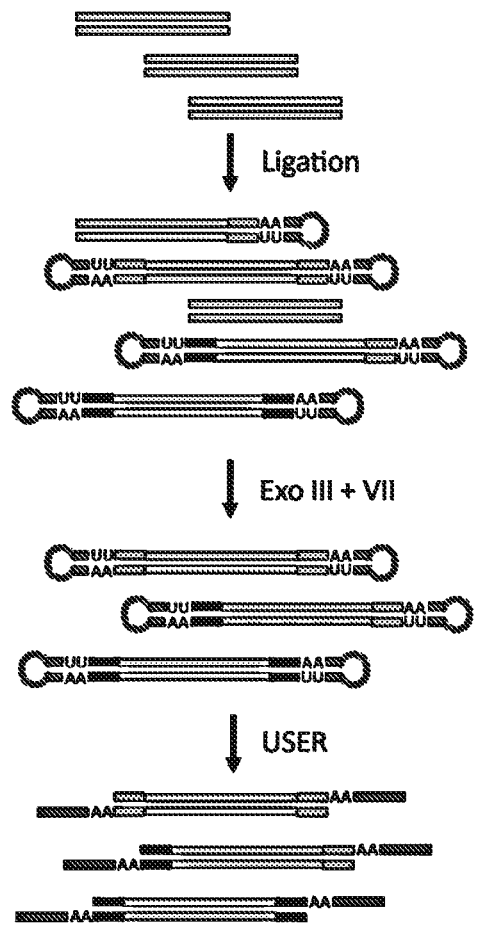
FIGS. 31A and 31B illustrate a sample preparation for in situ library construction. (31A) Size-selected HMW genomic DNA is end repaired and then ligated to hairpin adapters containing uracil nucleotides near the loop region. Blue and red indicate different priming sequences and each template molecule has a 50% chance of ligating to two different primer sequences. Treatment of the ligation products with exonuclease III and VII removes unligated DNA molecules that have exposed 3' or 5' ends. Uracil-specific excision reagent (USER™) treatment excises the uracil bases to open the hairpins and generate a flowcell-ready library with single-stranded 3'-tails. (31B) The library is loaded on a standard Illumina flowcell and both ends are allowed to hybridize. A hyperactive transposase is used to randomly fragment and insert common flowcell adapters in the HMW hybridized library to generate LMW cluster-ready templates. After cluster generation, reads from either end can be deconvolved by using the two different sequencing primers (shown in red and blue).
Figure 31B:
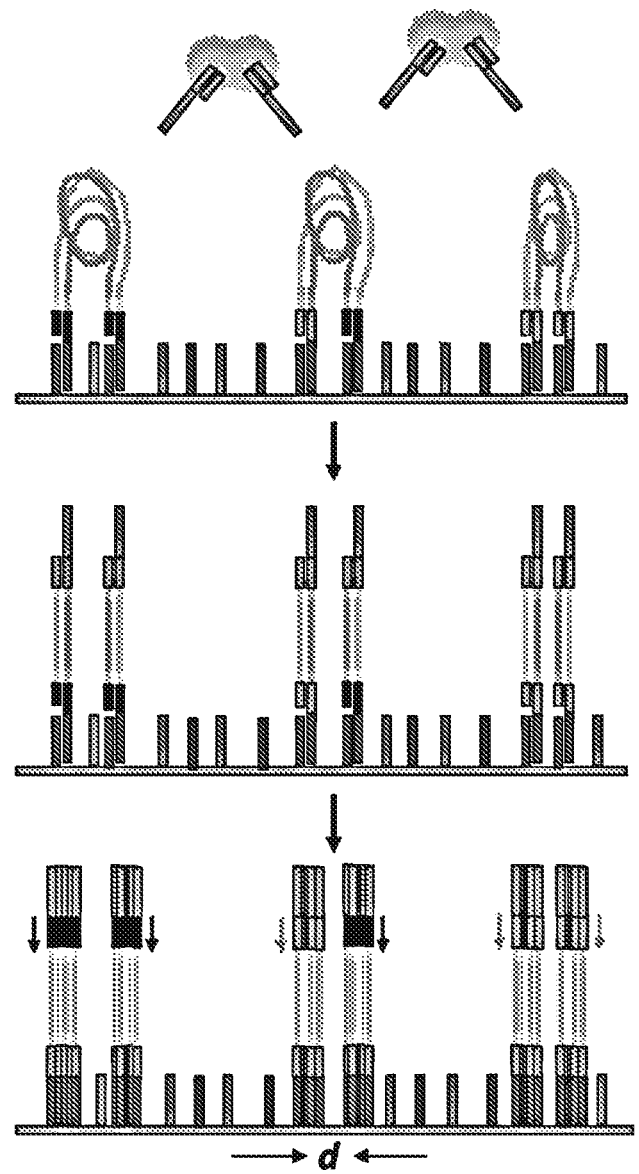

An efficient approach for generating HMW DNA libraries containing single-stranded flowcell compatible 3'-tails is provided herein. Briefly, genomic DNA from Eschericia coli was physically sheared, size selected for 1, 2 or 3 kb size molecules, purified, and end-repaired. Hairpin adapters containing three uracil bases near the loop of the hairpin (FIG. 31A) were self annealed and then blunt ligated to the size-selected libraries. Unligated genomic DNA and adapters were removed with treatment by Exonuclease III and VII to yield an enriched population of molecules with hairpin adapters on both ends. The molecules were then treated with USER™ to open the hairpin loop and release single-stranded flow cell complementary 3' tails. Both ends of the molecules were then hybridized to standard Illumina flow-cell surfaces using a slightly modified thermal cycling protocol. Tn5 transposase loaded with flowcell-compatible adapters was added to the flowcell to randomly fragment and add adapters to the HMW molecules thereby generating LMW sequencing-ready templates (FIG. 31B). Each E. coli library was pooled with a human control library, loaded onto a separate lane, and two separate single-end 36 bp reads (SE36) were obtained on an Illumina GAIIx.

Reconstructing Contiguity Information.

Table 1 below illustrates the distribution of mapping reads for the 1, 2 and 3 kb libraries constructed as described above.

TABLE 1

|  | 1 kb no filter | 1 kb >= Q30 | 2 kb no filter | 2 kb >= Q30 | 3 kb no filter | 3 kb >= Q30 |
|---|---|---|---|---|---|---|
| E. coli | 4,532,112 | 3,428,616 (76%) | 3,668,061 | 2,667,329 (73%) | 2,340,128 | 1,523,035 (65%) |
| human | 155,966 | 97,328 (62%) | 794,123 | 504,299 (64%) | 5,370,959 | 4,883,197 (91%) |
| adaptor/mosiac | 44,189 | 23,563 (53%) | 34,801 | 16,581 (47%) | 9,337 | 5,037 (54%) |
| unmapping | 6,269,729 | 780,191 (12%) | 5,930,170 | 565,338 (10%) | 2,755,611 | 215,931 (8%) |
| total | 11,001,996 | 4,329,698 (39%) | 10,427,155 | 3,753,547 (36%) | 10,476,035 | 6,627,200 (63%) |

Figure 32A:
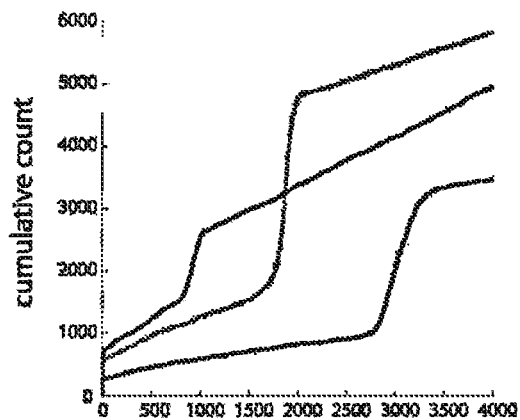
FIGS. 32A-32D show nearest neighbor pairs that were within 1.5 um of each other and 4,000 bp mapping distance were identified by comparing (32A) read 1 against read 1, (32B) read 2 against read 2, (32C) read 1 against read 2, and (32D) read 2 against read 1. The three colors represent three different sized libraries: blue=1 kb, green=2 kb, red=3 kb. The cumulative number of cluster pairs is plotted against the numerically sorted mapping distance for each pair.
Figure 32B:
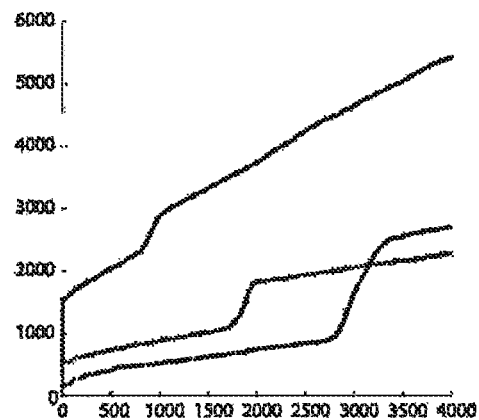

An average of 3.5M reads mapping to *E. coli* were obtained in each of the three lanes (Table 1). The X-Y coordinates of the clusters in every tile were used to calculate the spatial offset between read 1 and read 2 X-Y coordinates. For each cluster mapped to *E. coli* in read 1 and read 2, its nearest physical *E. coli* mapping neighbor within 1.5 μm was identified within the same read and the mapping distances of all pairs were numerically ordered (FIGS. 32A and 32B). Table 2 below shows the nearest neighbor cluster pair data.

TABLE 2

Nearest neighbor cluster pair data for the 1, 2 and 3 kb libraries when *E. coli* reads are compared against *E. coli* reads. The expected size ranges were set at 800-1200, 1500-2300 and 2500-3500 bp, respectively.

|  | Ref. read | Pairing read | NN pairs <1.5 μm <4000 bp | +within expected mapping distance | +reads have opposite orientation |
|---|---|---|---|---|---|
| 1 kb | 1 | 1 | 4,952 | 1,206 | 1,060 |
| 2 kb |   |   | 5,820 | 3,402 | 3,236 |
| 3 kb |   |   | 3,464 | 2,424 | 2,334 |
| 1 kb | 2 | 2 | 5,426 | 766 | 602 |
| 2 kb |   |   | 2,276 | 870 | 794 |
| 3 kb |   |   | 2,704 | 1,710 | 1,612 |
| 1 kb | 1 | 2 | 33,393 | 25,708 | 25,502 |
| 2 kb |   |   | 36,656 | 32,653 | 32,457 |
| 3 kb |   |   | 39,743 | 37,916 | 37,769 |
| 1 kb | 2 | 1 | 33,256 | 25,305 | 25,117 |
| 2 kb |   |   | 35,686 | 31,643 | 31,466 |
| 3 kb |   |   | 39,204 | 37,351 | 37,196 |
| 1 kb | 1 | 1 + 2 | 38,256 | 26,894 | 26,544 |
| 2 kb |   |   | 42,242 | 35,885 | 35,525 |
| 3 kb |   |   | 43,097 | 40,272 | 40,036 |
| 1 kb | 2 | 2 + 1 | 38,597 | 26,894 | 25,708 |
| 2 kb |   |   | 37,841 | 32,438 | 32,192 |
| 3 kb |   |   | 41,761 | 38,950 | 38,701 |
| 1 kb | 1 + 2 | 2 + 1 | 29,676 | 23,028 | 22,863 |
| 2 kb | mutually exclusive |   | 33,064 | 29,505 | 29,350 |
| 3 kb |   |   | 35,701 | 34,082 | 33,946 |

Figure 34A:
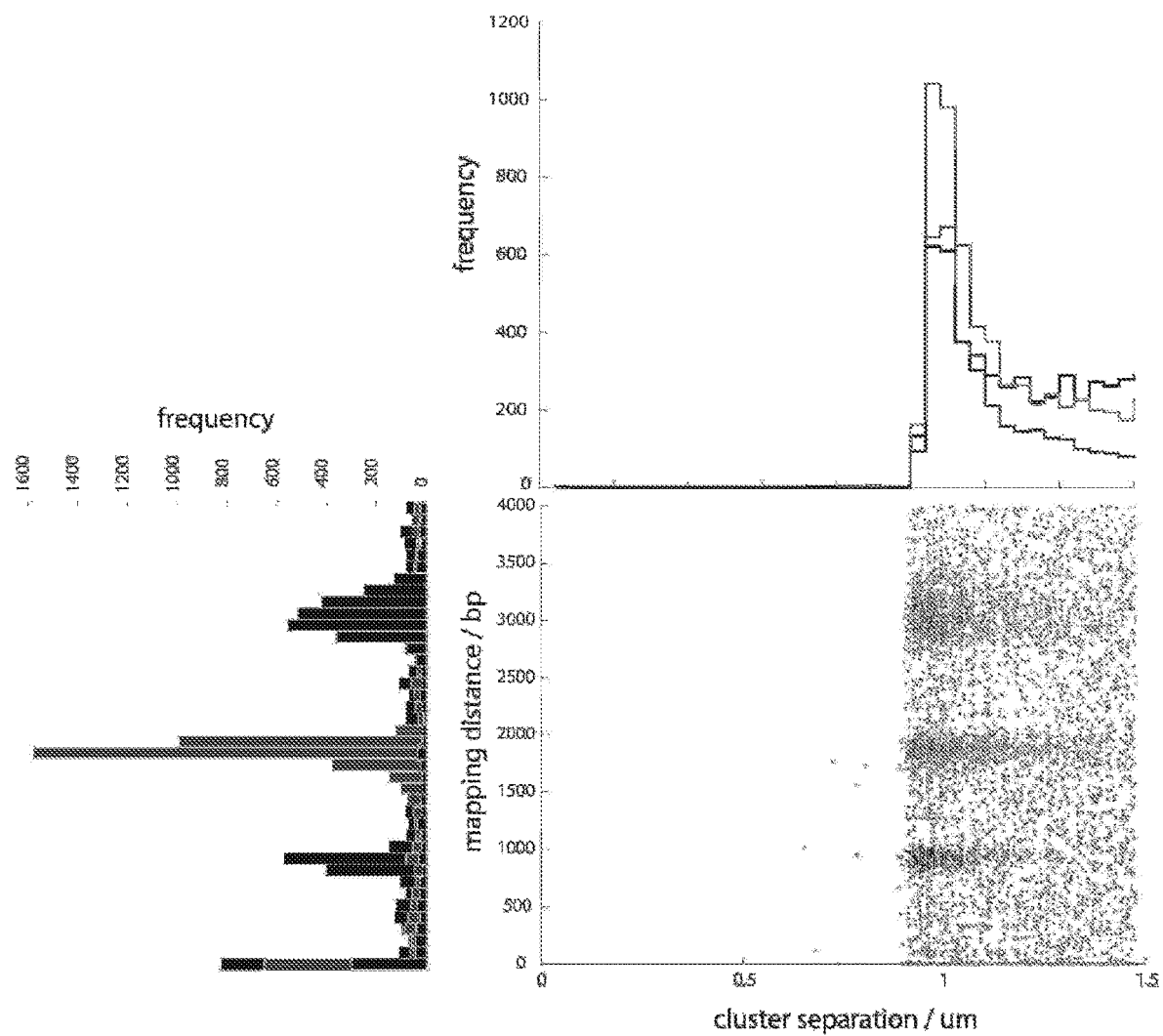
FIGS. 34A and 34B are a series of data illustrating cluster separation in read 1 and 2 according to one embodiment. (34A) Every cluster that had a nearest neighbor within 1.5 μm and 4,000 bp mapping distance was identified within read 1 for the three libraries (blue=1 kb, green=2 kb, red=3 kb). The mapping distance is plotted against the cluster separation distance and histograms along each axis are shown. Note that the native Illumina image processing software will not demarcate two clusters that are closer than ~0.9 μm. (34B) The nearest neighbors for every cluster in read 1 was identified in read 2 and plotted as above.

Between 766-3,402 cluster pairs with the expected mapping distance were observed for each library (FIGS. 32A and 32B). A low number of cluster pairs were seen within a single read because clusters often physically overlap on the surface and Illumina's image analysis software is unable to distinguish them. Plotting mapping distance as a function of physical separation (FIG. 34A) revealed the default lower limit of resolution between two clusters in a single read to be ~0.94 μm.

Figure 32C:
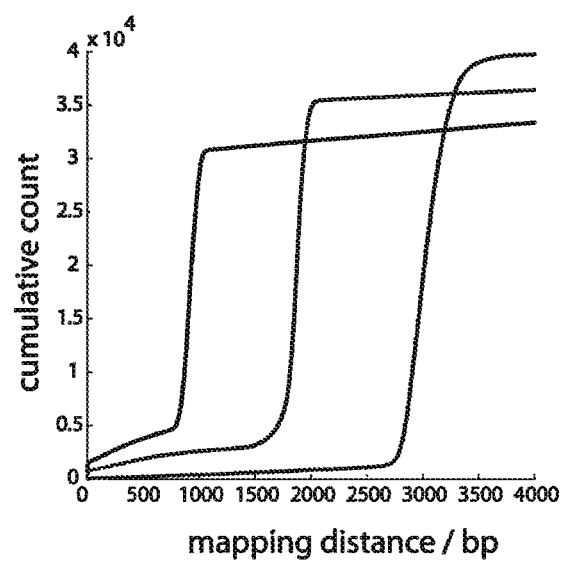
Figure 32D:
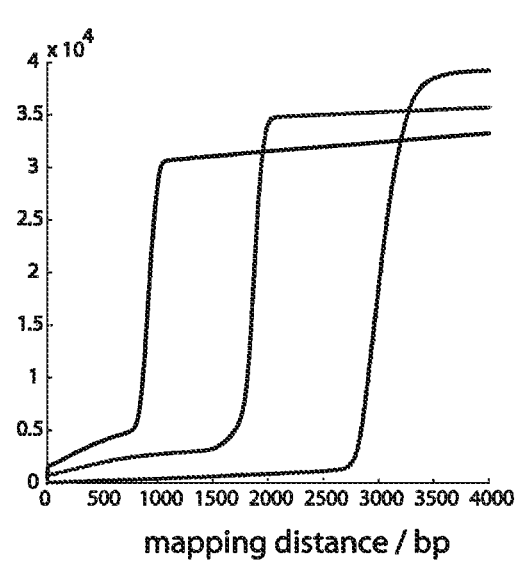
Figure 33:
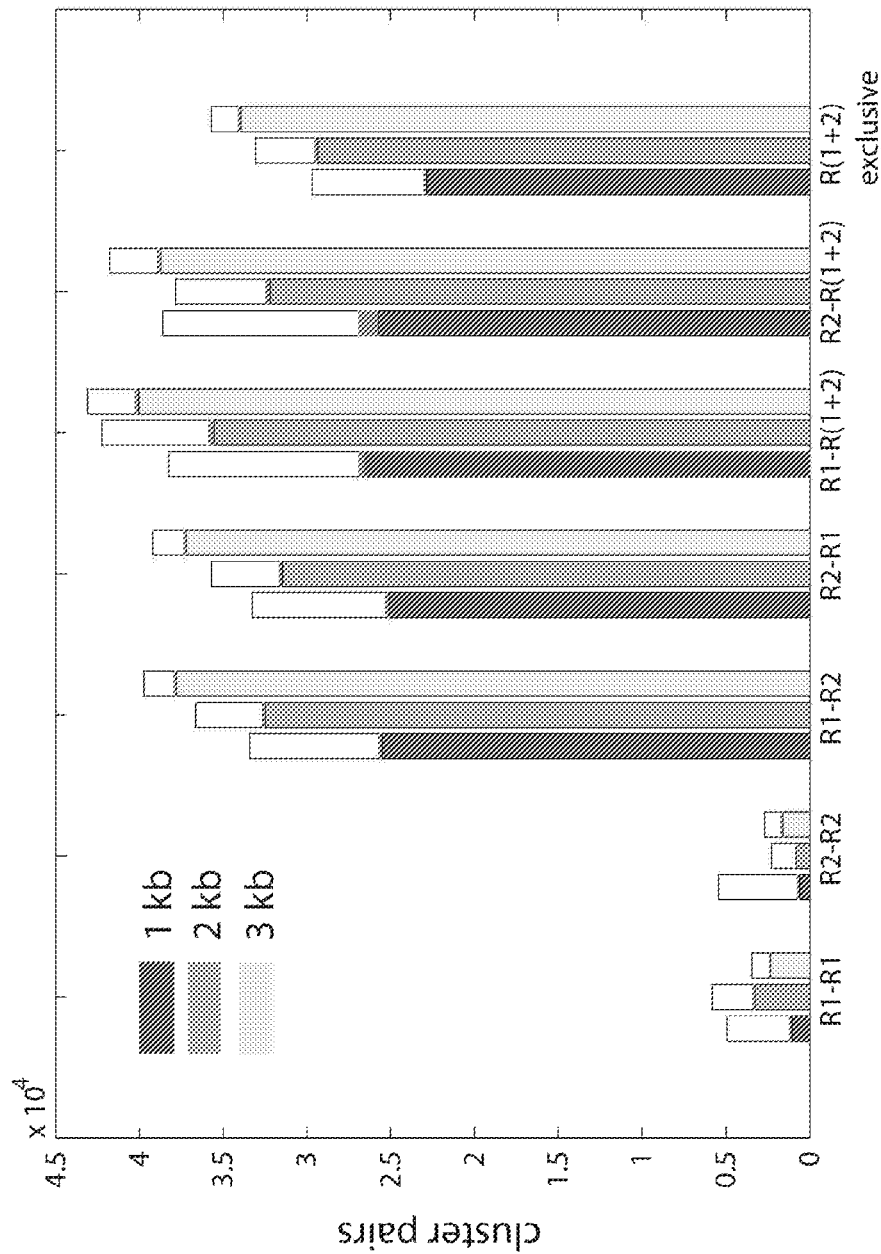
FIG. 33 shows nearest neighbor cluster pair data for the 1, 2, and 3 kb libraries for different nearest neighbor searches. The white bars are the total number of cluster pairs with <1.5 μm physical separation and <4000 bp mapping separation. The grey bars are the number of pairs within the targeted size range for that library size (800-1200, 1500-2300, and 2500-3500 bp, respectively). The colored bars are pairs that are within the targeted size range and have reads on opposite strands in opposite directions.
Figure 34B:
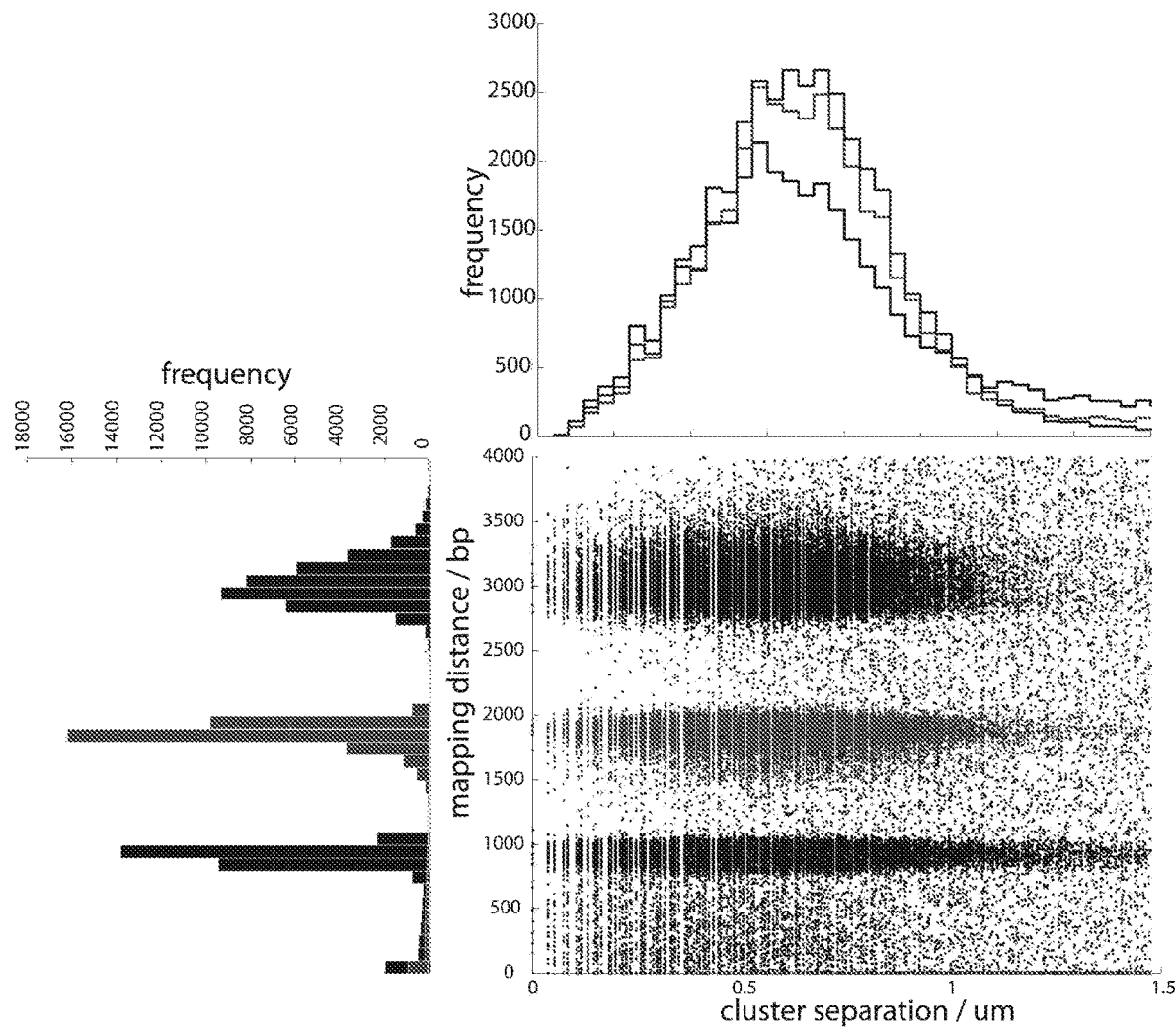

The nearest-neighbor search was repeated by looking for cluster pairs<1.5 μm between reads 1 and 2. Up to 37,916 distinct cluster pairs were identified within the expected mapping separation range (Table 2; FIG. 33 and FIGS. 32C and 32D). Of these, over 99% were cluster pairs that gave reads on opposite template strands going in the opposite direction, which is the is expected orientation based on the design of the in situ library preparation. With this approach of serially obtaining paired reads, cluster pairs closer than 0.94 μm were clearly demarcated, including some that were almost completely overlapping (FIG. 34B). The mean mapping separation for the cluster pair libraries was 946 bp, 1,770 bp, and 2,995 bp for the 1, 2, and 3 kb libraries, respectively (FIG. 34B, top histogram). The 2 kb library was likely a little low due to a wider size selection.

Separation distances were calculated based on a freely-jointed chain model of DNA tethered to a surface. Using a freely-jointed chain model, the free-space distribution function for the end-to-end vector of a DNA molecule is Gaussian. It is described by the equation:

$$G(\vec{r}, \vec{r_0}) = C_0 e^{\left(-\frac{3(\vec{r}-\vec{r_0})^2}{2bL}\right)} \qquad (1)$$

where L is the contour length, b is the Kuhn length (twice the persistence length), and $C_0$ is a normalization constant. In the case where we have a surface at z=0 and the molecule starting at [0, 0, $z_0$], the distribution function becomes $$G_{surf}(\vec{r}\,[0,0,z_0]) = C_0'(G(\vec{r},[0,0,z_0]) - G(\vec{r},[0,0,-z_0])) \qquad (2)$$

where $C_0'$ is a new normalization constant and the second term represents the entropic repulsion from the surface. As $z_0 \to 0$, the difference becomes a derivative which gives $$G_{surf}(\vec{r},[0,0,0]) = C_0'' r_z G(\vec{r},[0,0,0]) \qquad (3)$$

where $C_0''$ is a normalization constant. Plots of $G_{surf}$ for the x, y and z components of $\vec{r}$ are shown in FIGS. 39A and 39B.

The mode physical cluster separation for the 1 kb pairs was 0.44 μm and for the 2 kb and 3 kb pairs it was 0.67 μm, with the tail of the distribution showing some cluster pairs separated by >1.0 μm. These observed physical separation distances between Infinipair reads were significantly larger (3-4 fold) than expected (FIG. 39A). For example, the mean physical distance between 3 kb cluster pairs was ~1000 nm which roughly corresponds to the contour length of the molecule. At least two possible explanations were contemplated for this discrepancy: 1) the image offsets are slightly off thereby giving rise to overestimates of the true physical distances, or 2) the large separation distances arise as an artifact during cluster formation. To verify the offsets, histograms showing the distribution of angles between every cluster pair were generated and the cumulative direction vector for all pairs was calculated. One would expect a random distribution of angles between pairs if the images are properly aligned and a net zero vector sum; a bias towards a subset of angles within a given tile or a non-zero vector sum suggests the offsets are slightly off. This did not appear to be a significant source of error. Therefore, these large separation distances arise as an artifact during cluster formation. Therefore, this observed discrepancy arises due to the way in which the clusters were generated on the flowcell (FIG. 39C). If two cluster-capable molecules are hybridized within 50-100 nm of each other, there will be a highly localized depletion of available adapters between the templates during the initial cycles of bridge PCR. This effectively forces the clusters to grow away from each other. As a result, the X-Y coordinate of each cluster will not accurately reflect the X-Y coordinate of the initial seed templates.

Using read 1 as a reference, the closest nearest neighbor was screened for from either read 1 and read 2 (FIG. 33). For pairs within the expected mapping distance and in the correct orientation, fewer than 1% had a different nearest neighbor in the combined dataset, and this observation remained true when using read 2 as the reference. Applying a more restrictive filter that requires mutual exclusivity (i.e., the nearest neighbor of cluster A is B and that of B is A) reduces the number of candidate pairs by up to 10% but does not yield any significant gain in sensitivity. It is also noted that as the library size increases, a greater fraction of the total cluster pairs give rise to pairs within the target size range with reads in the correct orientation. This may be due to steric effects whereby larger molecules occupy larger volumes, and thereby prevent other molecules from hybridizing to the surface nearby.

Although the number of related cluster pairs represented only accounts for approximately 1% of the total reads mapping to *E. coli*, it demonstrates that in situ transposition and library preparation is technically feasible. At least two factors may contribute to the low efficiency: 1) a low probability for DNA to adopt the appropriate conformation to favor both ends annealing to the surface; and 2) transposon insertion in close proximity to the ligated adaptor sequence. The 3D probability distribution for the end-to-end vector of a DNA molecule with one end tethered to a surface indicates that the free end has a much higher probability of being far away from the surface than close to it. This problem is exacerbated with increasing DNA length. When only one end hybridizes and the molecule undergoes transposition, it generates a singleton read and not have a related nearest neighbor. Further, factor (2) is evidenced by the finding of 9,294 nearest-neighbor cluster pairs where read 1 mapped to *E. coli* and read 1 mapped to transposase mosaic and/or flowcell adaptor sequence. Fine tuning of the transposase concentration and incubation time may help improve this but it may be difficult to completely eliminate it.

Figure 37A:
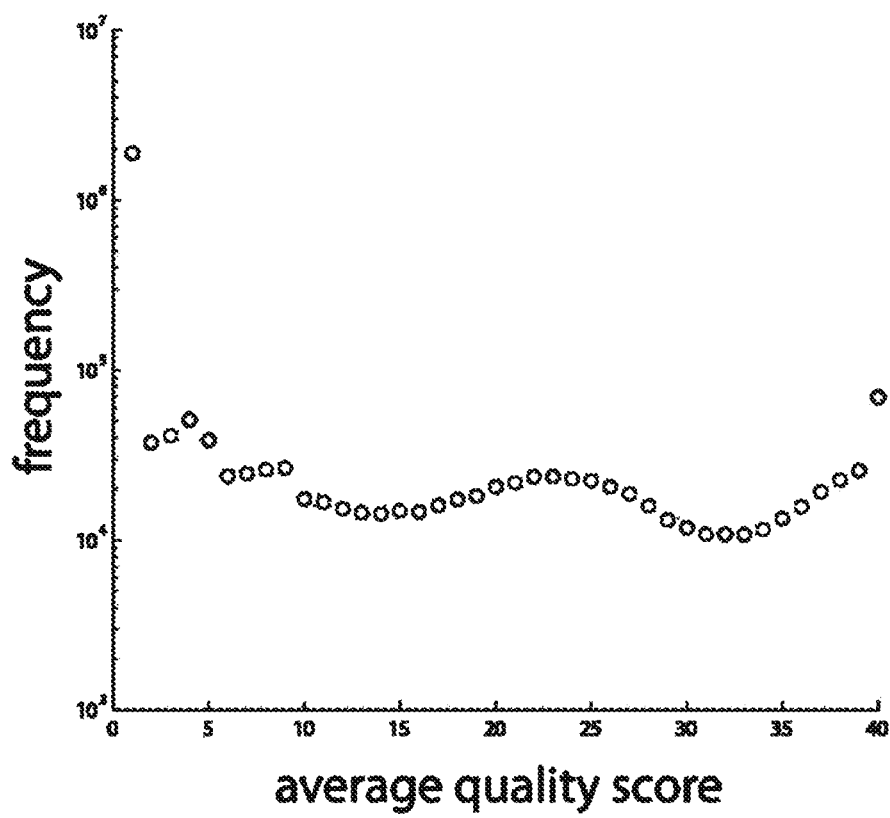
FIGS. 37A and 37B illustrate distribution of average raw quality score for all unmapping read 1's in the 3 kb library (37A) and for all nearest neighbor (NN) pairs consisting of one E. coli and one unmapped read, the average raw quality score for the unmapped read is shown in a histogram.
Figure 37B:
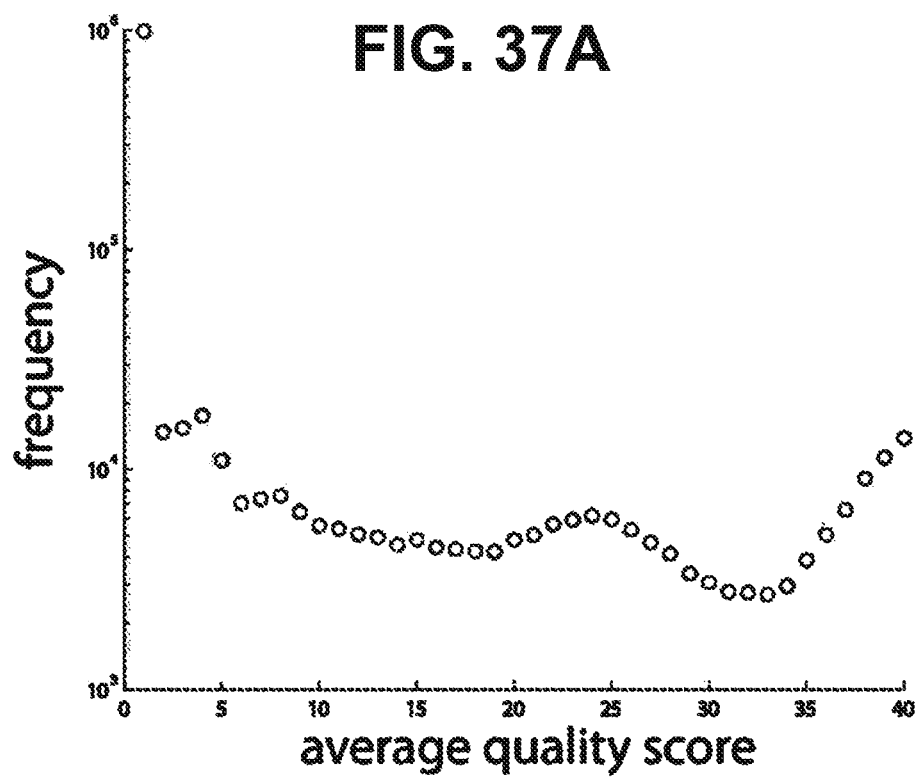

Surprisingly, the majority of reads for all three libraries did not map to human, *E. coli*, or adapter sequences (Table 1). The average quality score for the unmapping reads was typically low: only 8% had average raw quality scores>30 and 69% had the lowest possible average raw quality score of 2 (FIG. 37A). When all reads were considered, and not just those mapping to *E. coli* for nearest-neighbor proximity, 15.7% of the nearest neighbor pairs had one read mapping to *E. coli* and one unmapping read, and 6.8% had both mapped to *E. coli*. For the pairs that had one unmapping read, only 6% of them had an unmapping read with an average raw quality score>30 and 78% had the lowest possible raw quality score (FIG. 37B). Although the source of these unmapping reads is not clear, they can largely be filtered out based solely on quality score alone.

Figure 35A:
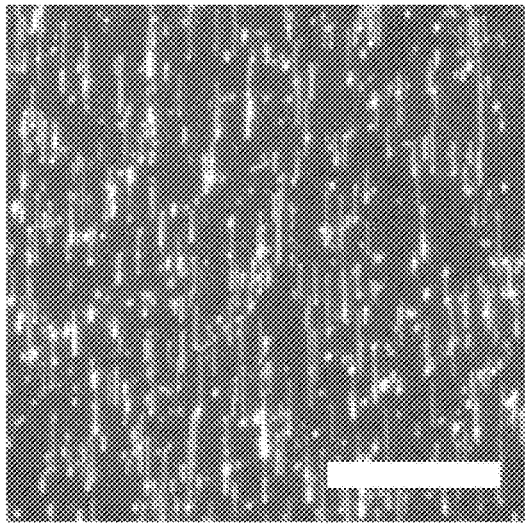
FIGS. 35A and 35B show illustrative images of stretched DNA according to one embodiment. (35A) 48.5 kb lambda genomes were stained with JOJO-1, tethered to a modified Illumina flowcell, and stretched with a 15V/cm electric field. Imaging was performed on an Illumina GA2x. (35B) The stretched DNA was then treated with transposomes for 5 minutes at 55° C. and imaged again. Scale bars=20 μm.
Figure 35B:
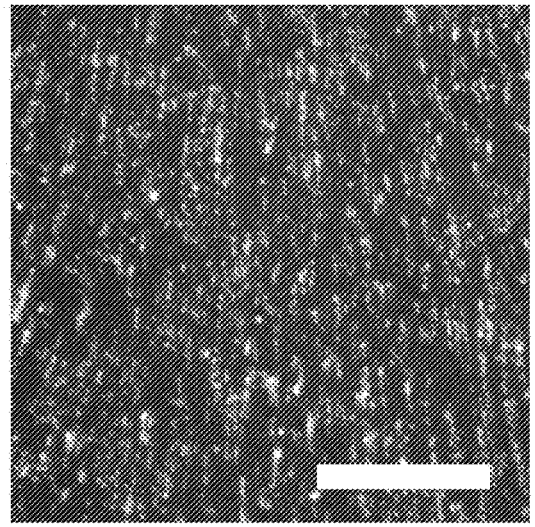

In situ stretching and tagging of HMW molecules. In an effort to improve the hybridization efficiency and explore further applications of this sequencing paradigm, in situ stretching and fragmentation of HMW molecules was successfully performed within Illumina flow cells. Briefly, flowcells were cleaned using Piranha solution, treated with 2% 3-aminopropyltriethoxysilane (APTES), and loaded with JOJO-1 stained lambda DNA. The flowcell was then loaded with 6M KCl and an electric field of 15V/cm was applied at the input and output ports for 90 sec. Surfaces were imaged directly on an Illumina GA2 sequencer (FIG. 35A) to demonstrate that the ends of single 48.5 Kb molecules can be physically stretched over ~40 pixels of imaging space. Surfaces were then treated in situ with transposome and re-imaged (FIG. 35B). Individual molecules were clearly fragmented in multiple locations, demonstrating the enzyme's ability to maintain high activity levels even on a surface-immobilized template. It should be straightforward to build on these methods to incorporate flowing in the "lock-down" bridge prior to fragmentation on native flowcells, so that clusters may be generated at the ends of long templates.

Figure 40A:
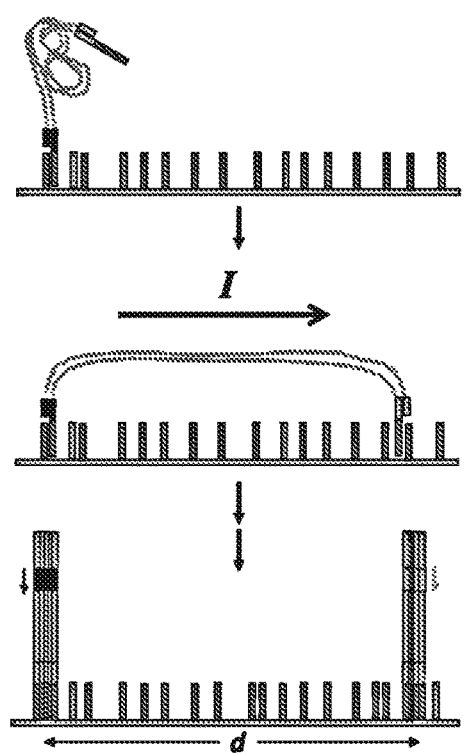
FIG. 40A is a schematic illustration of the in situ stretching process described herein. One end of a HMW molecule was hybridized to a surface prior to the application of an electric field. While the field is applied, molecules with a free end are stretched in the direction of the current flow. The free end is then able to hybridize and sequencing proceeds as usual.
Figure 40B:
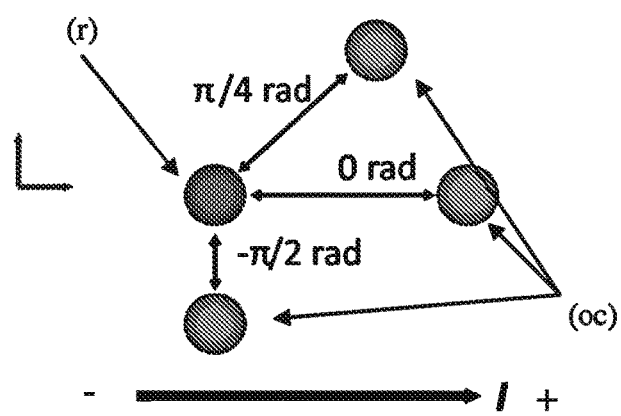
FIG. 40B shows angles between clusters determined by selecting the cluster furthest from the positive electrode as the reference (r). The angle to the other cluster (oc) was then calculated.
Figure 41A:
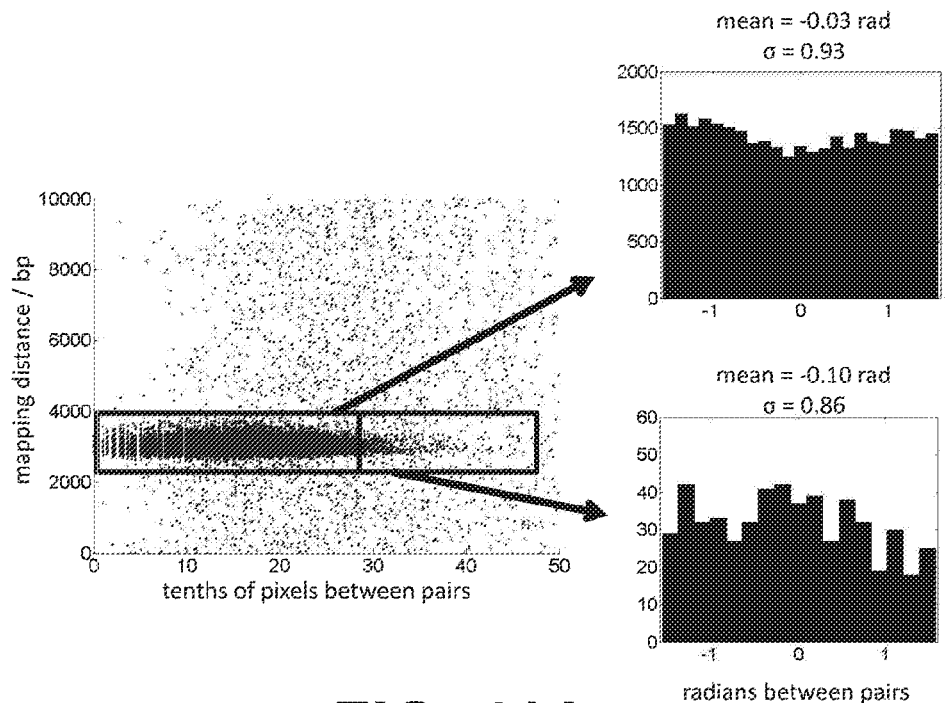
FIG. 41A is a set of scatterplots showing mapping distance vs. physical separation for the 3 kb E. coli library in the absence of an applied external electric field. For the points shown in the boxes, histograms of the relative angle (in radians) between pairs are shown on the right.
Figure 41B:
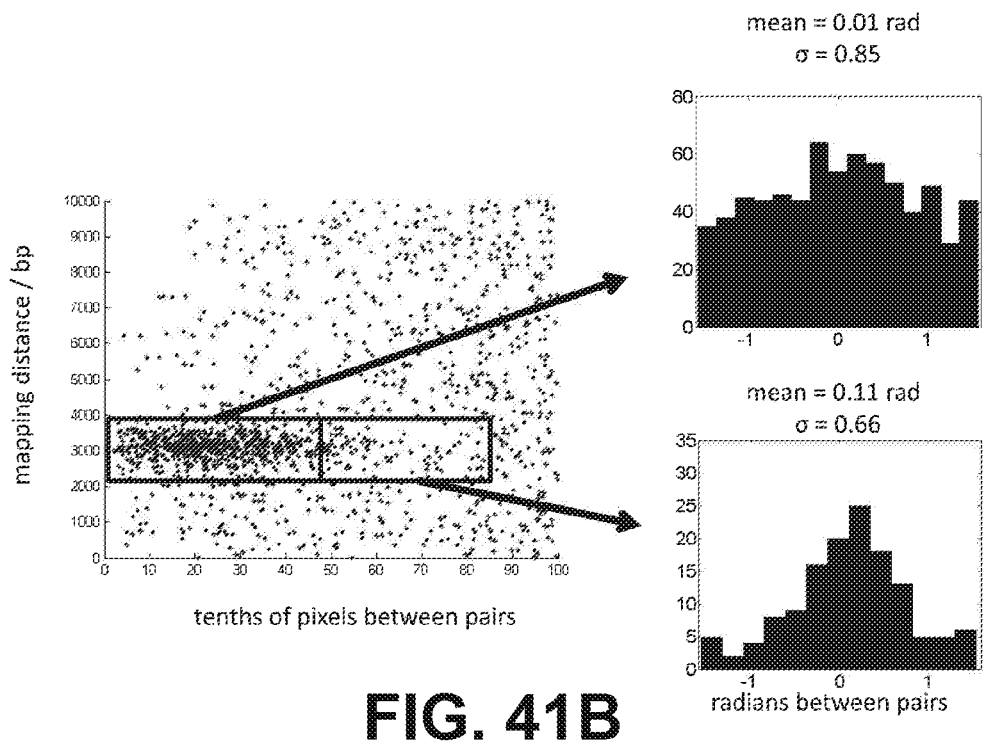
FIG. 41B shows the plots as in FIG. 41A but under-hybridization was performed in the presence of a 28 V/cm electric field. Cluster pairs that were separated by at least 4.5 pixels appear to be aligned along the axis of the flowcell and parallel to the electric field (bottom right).

Using the 3 kb *E. coli* library described above, in situ stretching and sequencing of the ends of stretched molecules was also successfully performed within Illumina flow cells (FIG. 40A). Template libraries were loaded into a flow cell at 75° C. and the chamber was slowly cooled at 0.1° C./s to 55° C. Next, hybridization buffer containing 5×SSC and 200 mM KCl was flowed into the chamber and a 28 V/cm electric field was applied for either 0 or 2 seconds. Wash buffer was then flushed through the chamber prior to in situ transposition and sequencing. In the absence of an applied electric field, the angles between clusters in a pair were randomly distributed and not correlated with the distance between the clusters. For cluster pairs that were separated by at least 45 tenths of pixels (~1.6 µm), 46% had angles (FIG. 40B) between ~7/4 and 7/4 with respect to the axis of current flow in the chamber (FIG. 41A). However, in the presence of the electric field, 78% of cluster pairs separated by >45 tenths of pixels had angles within this range (FIG. 41B). This is strongly indicative that these pairs had at least one end of the molecule hybridized at the time the field was applied, at which point the other end was stretched by the electric field before it hybridized to the surface. These results demonstrate that in situ stretching and sequencing of HMW DNA can be accomplished within native flowcells.

Discussion

Diverse technologies currently exist for determining contiguity information on a variety of length scales, including optical mapping (Schwartz et al. 1993), stretching single molecules in nanochannels (Riehn et al. 20057), single chromosome sorting (Fan et al. 2011), long-read single molecule sequencing (Eid et al. 2009), large insert cloning (Kitzman et al. 2011), and transmission electron microscopy. However, all of these technologies remain prohibitive for widescale use due to capital equipment costs or the expertise required for implementation. In the experiments described above, it was successfully demonstrated that in situ library preparation of HMW DNA molecules enables the capture of long-range sequence information up to 3 kb apart on an existing sequencing platform. The method described herein may overcome these limitations by taking advantage of existing sequencing hardware and single-step enzyme-based in situ library preparation. Further, the methods described have shown that paired-end sequencing can be accomplished without circularization.

There are at least four factors that affect the generation of related nearest neighbor clusters: 1) the production of a HMW library with uniform single-stranded flowcell compatible 3' adapters, 2) the hybridization of both ends to the flowcell surface, 3) the uniform and nondestructive in situ transposition of bridged molecules, and 4) the generation of clusters that are largely overlapping. Control experiments suggest that the aforementioned approach using hairpin adapters followed by Exo III/VII treatment is highly effective at eliminating any library molecules that do not have two hairpin adapters. Additional control experiments have shown that USER™ treatment is also very efficient at uracil excision for making adapters single stranded, suggesting that the initial library construction is robust. Although it may be argued that having both ends of a molecule be situated near the surface is unfavored due to entropic arguments, it is more favorable than the circularization of a same-length single molecule due to the fact that each end can hybridize to any one of thousands of flowcell adapters. There may also be ways to force both ends to be closer to the surface to improve the hybridization efficiency, such as with the use of tethered magnetic beads or an electric field. For the in situ transposition step, a range of transposase concentrations and incubation times were used to identify the optimal balance between too little activity and too much activity, both of which result in a failure to generate clusters.

Figure 38A:
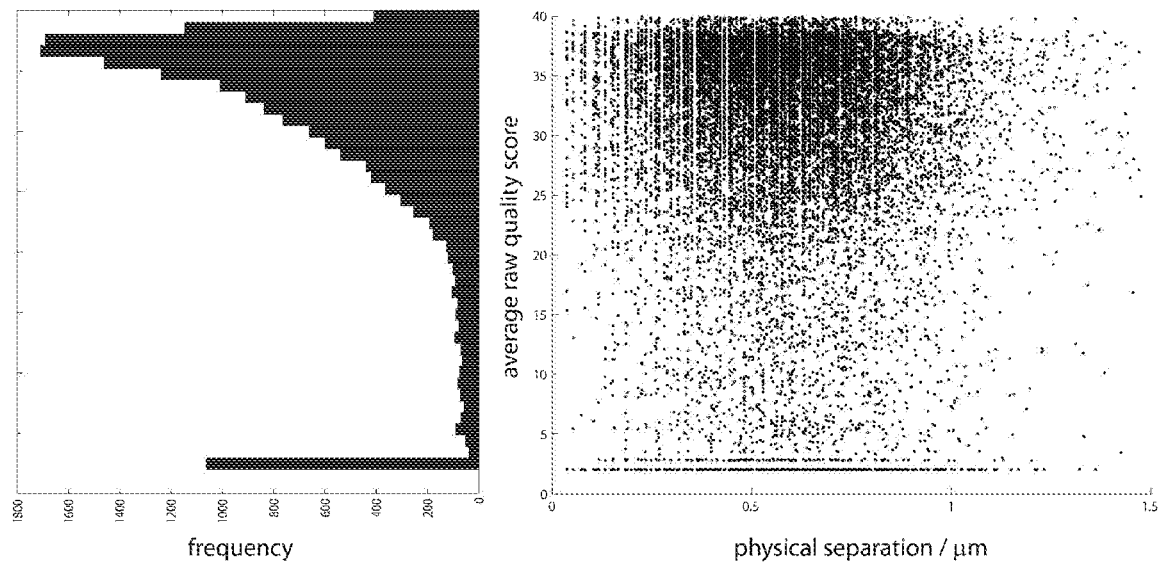
FIGS. 38A and 38B illustrate the average raw quality score across all bases for read 1 (38A) and read 2 (38B) in the 3 kb library. Reads are those found in nearest neighbor pairs that mapped to E. coli, separation<1.5 µm, and mapped between 2500 and 3500 bp.
Figure 38B:
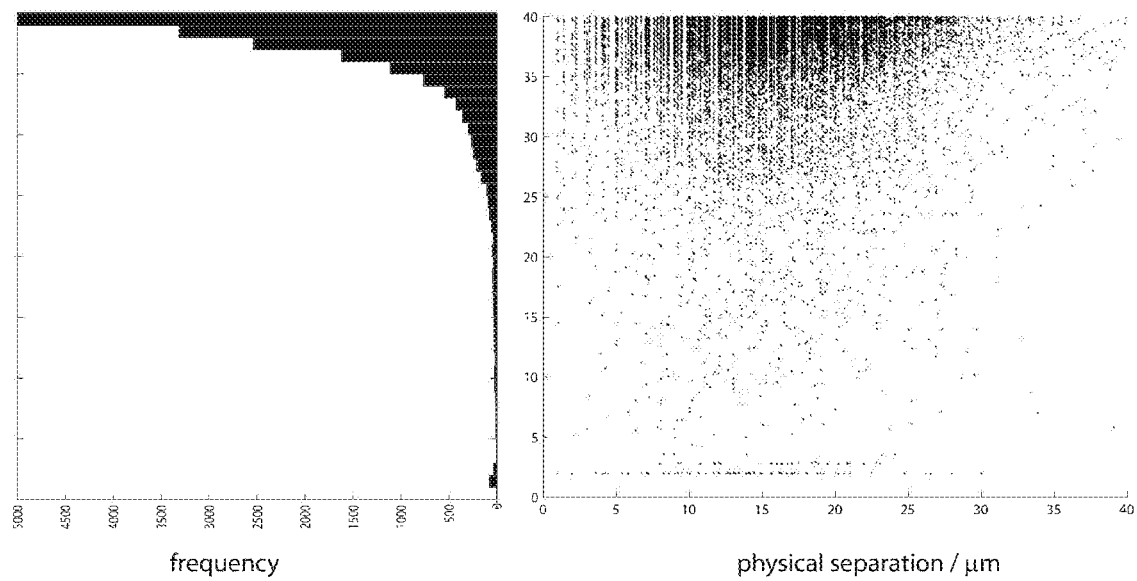

The effect on sequence quality of intentionally generating clusters that are largely overlapping is harder to interrogate. For example, it may be that when there are two cluster-ready templates hybridized on the surface in close proximity that one of them will out-compete the other during bridge amplification, as often happens during conventional bulk solution PCR. This can be due to differences in sequence composition, melting temperature, length, and the stochasticity of polymerase binding events. In the method described herein, control of the final length of the related nearby templates has been limited after transposition (one could be 200 bp and the other could be 800 bp). While it could a concern that the clusters are too close together, this does not appear to be the case here. In such a case, the quality scores would decrease with nearest neighbor cluster distance due to having fewer numbers of molecules within either cluster and/or the potential for mixed reads. Here, however, quality scores for read 2 were generally better than for read 1 and there does not appear to be a correlation between average quality score and nearest neighbor cluster distance (FIGS. 38A and 38B).

Although the high background currently makes the approach impractical to use for de novo assembly, further improvements to the library preparation and in situ transposition methods mal lead to a concomitant improvement in signal to noise. Ultimately in situ library preparation methods may enable the generation of reads whose physical relationship to one another on a flow cell is correlated with genomic distance, enabling the routine optical sequencing of multiple, ordered reads from many single HMW molecules as described below.

3.B. Achieving Multiple In Situ Reads Per Single DNA Molecule

Figure 15:
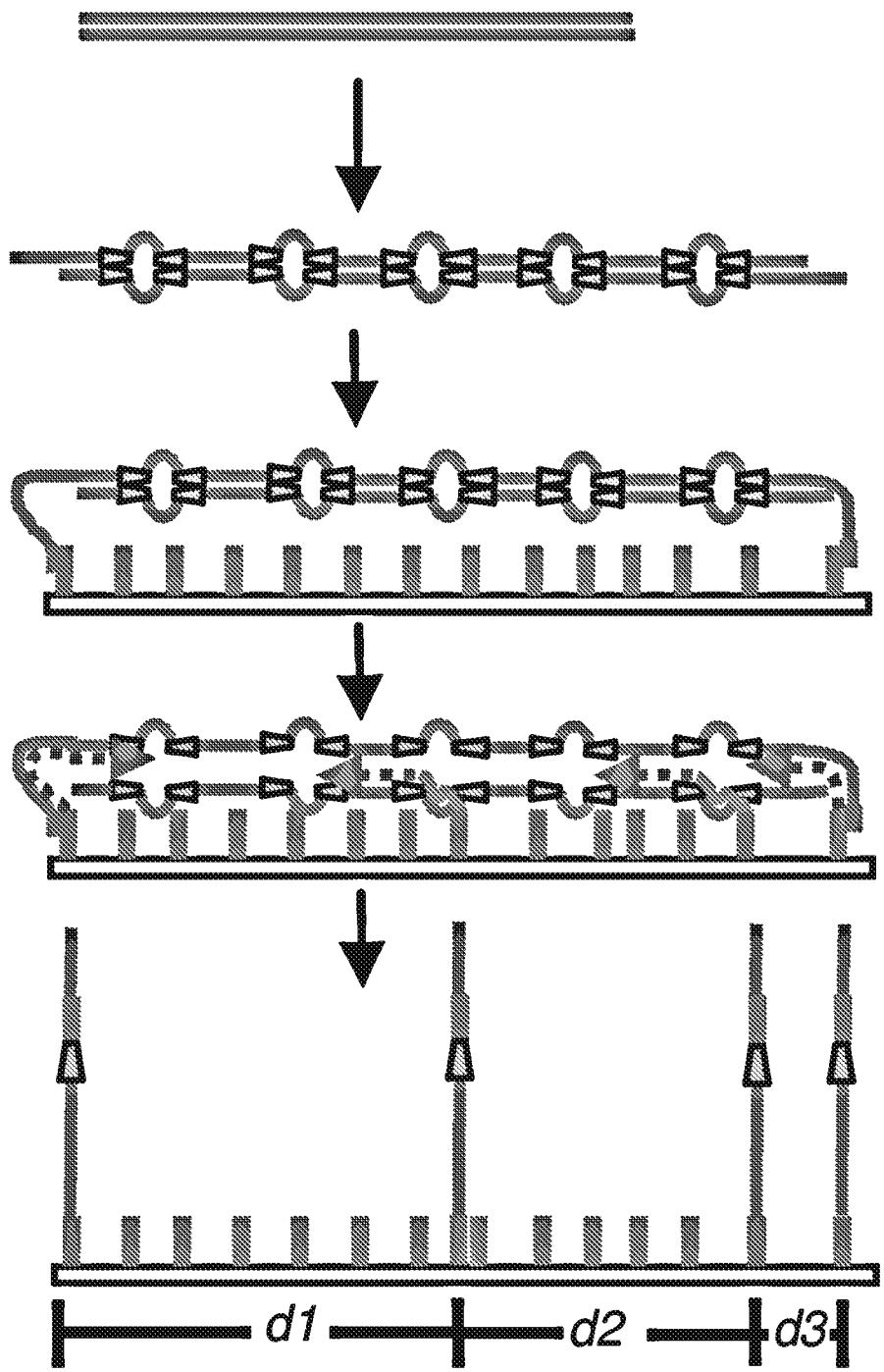
FIG. 15 is a schematic diagram illustrating pretreatment of the library to insert flowcell compatible adapters, without fragmentation, allowing for multiple read pairs to be generated along the axis of the stretched molecule.

Stretching prior to in situ transposition offers a number of advantages over the random-coil method. First, with stretching, the physical distance between co-linear clusters is expected to be directly proportional to the distance between reads, rather than proportional to the square root, thereby providing greater resolution. Second, stretching is more readily amenable to the second goal of this aim, which is to generate large numbers of independent reads along the full length of arbitrarily long single DNA molecules. In one scheme, diagrammed in FIG. 15, stretched single molecules are subjected to in vitro transposition with synthetic, continuous transposons, containing the 19 bp ME sequences that are connected by sequence that includes a single-stranded bubble. This is similar to the first steps of the strategy in FIG. 4, except that rather than degenerate sequences, each arm of the bubble is corresponds to the forward or reverse sequences of the primers that coat the flowcell. Once these synthetic, continuous transposons are inserted to high density (every 35 to 600 bp), the highly interspersed single molecules are stretched on the flowcell with current (without removal of the transposome complexes, such that there is no need for repair of the 9 bp lesions). Assuming a modest efficiency of hybridization and cluster PCR initiation from each bubble, this will likely yield multiple sequencing reads along the length of each stretched molecule.

The full area of each lane of the flow-cells that are used according to the long-range contiguity method described above is 245,760 pixels in the dimension of flow (2.5 cM) and 3,776 pixels in the orthogonal dimension. As lambda DNA (48.5 Kb) was stretched to ~30 pixels, as many as 400×1 Mb molecules may be stretched end-to-end along the full lane. At ~$\frac{1}{20}^{th}$ density, a single lane would be sufficient to support 14× physical coverage of a diploid human genome. For data analysis, published algorithms for optical mapping (Zhou et al. 2009; Zhou et al. 2007; Lin et al. 1999; Lim et al. 2001; Lai et al. 1999; Schwartz et al. 1993) may be used as well as previous experience in image analysis for sequencing applications (Shendure et al. 2005; Mitra et al. 2003). Such analysis may be performed directly from images, or alternatively from platform-generated sequence reads annotated with position-of-origin information. The positional information can be correlated with sequence data generated from co-linear or overlapping clusters.

The resulting data should be similar to that generated by optical maps, but has the following advantages:
1) Sequence reads represent data points that have much greater information content than restriction enzyme sites for both de novo assembly and haplotype resolution;
2) Issues that impact optical mapping such as restriction enzyme star activity and incomplete digestion will not occur with this approach; and
3) The positions of data points along the length of stretched DNA molecules will be random, rather than dependent on the restriction enzyme cut-site distribution.

The effect of extra templates hybridizing near to the stretched or coiled templates (which can confound the interpretation of the physical coordinates) can be mitigated by size-restricting the single DNA molecule populations and/or tuning template concentrations. However, these methods can be implemented without major sacrifices to cluster density, as the sequencing should be as dense as would normally be the case on the same platform.

Figure 21:
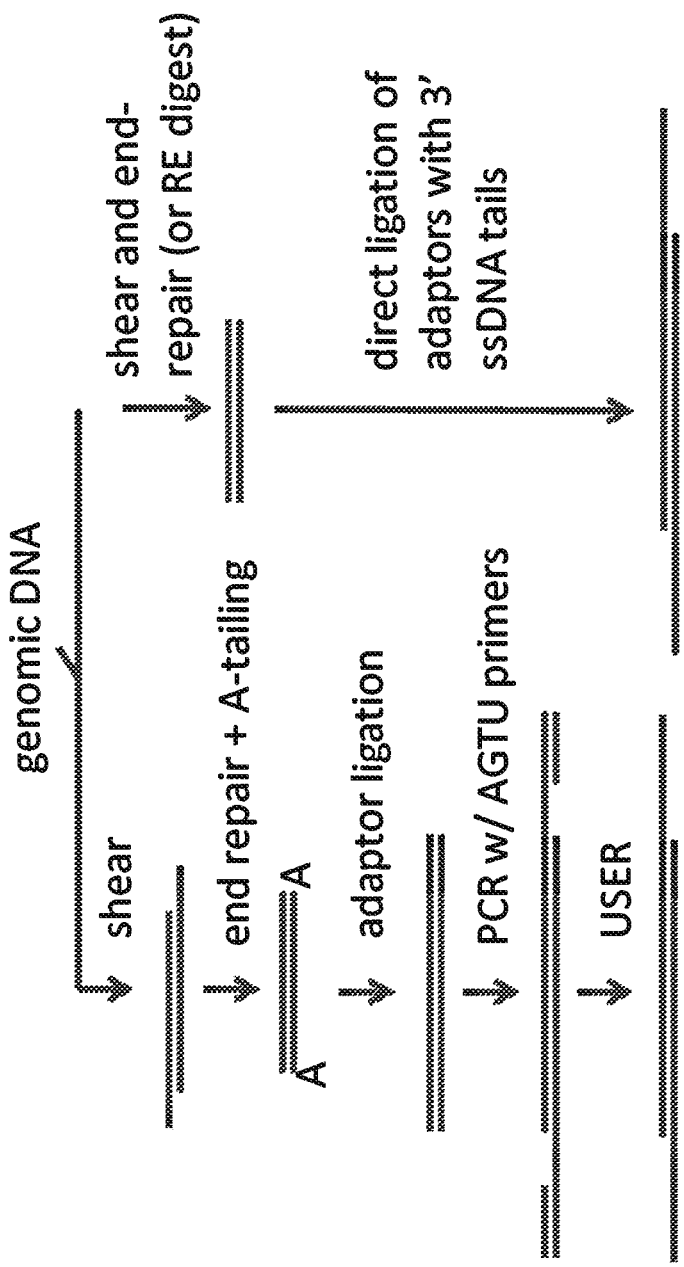
FIG. 21 illustrates two methods to generate shotgun HMW genomic DNA fragments with appropriate adaptors and 3' ssDNA tails corresponding to flow-cell sequence.

To generate HMW DNA with single-stranded tails corresponding to A1 and A2 appended to each end, two strategies are pursued. In the first (FIG. 21, left), genomic DNA is physically sheared (e.g. with HydroShear), and then end-repaired, A-tailed, and ligated to adaptor sequences corresponding to A1 and A2. The library is then PCR amplified using primers corresponding to A1 and A2 in which all thymine bases are replaced by uracil. Post-PCR treatment with USER™ is expected to yield the desired 3' single-stranded, flow-cell compatible tails flanking the double-stranded HMW DNA molecule. One advantage of this approach is that self-complementarity of end-sequences is expected to limit accumulation of A1-A1 and A2-A2 products, whereas a disadvantage is that it may not be practical for HMW fragment sizes that are largely incompatible with PCR, i.e. >10 Kb. As an alternative, libraries were generated in which A1 and A2 adaptors containing single-stranded, flow-cell compatible tails are directly ligated to blunt-end or restriction digested HMW genomic DNA (FIG. 21, right). An advantage of this method is that it is independent of the length of the HMW molecules. However, only 50% of products will be A1-A2 flanked (with the remainder either A1-A1 or A2-A2).

Both library preparation methods shown in FIG. 21 were applied to generate adaptor A (A1/A2) flanked shotgun HMW molecules from *E. coli* genomic DNA. Then, transposase loaded with synthetic transposons that include adaptor B for in situ fragmentation on the flow-cell surface (i.e. the method shown in FIG. 12B) was used.

Figure 22:
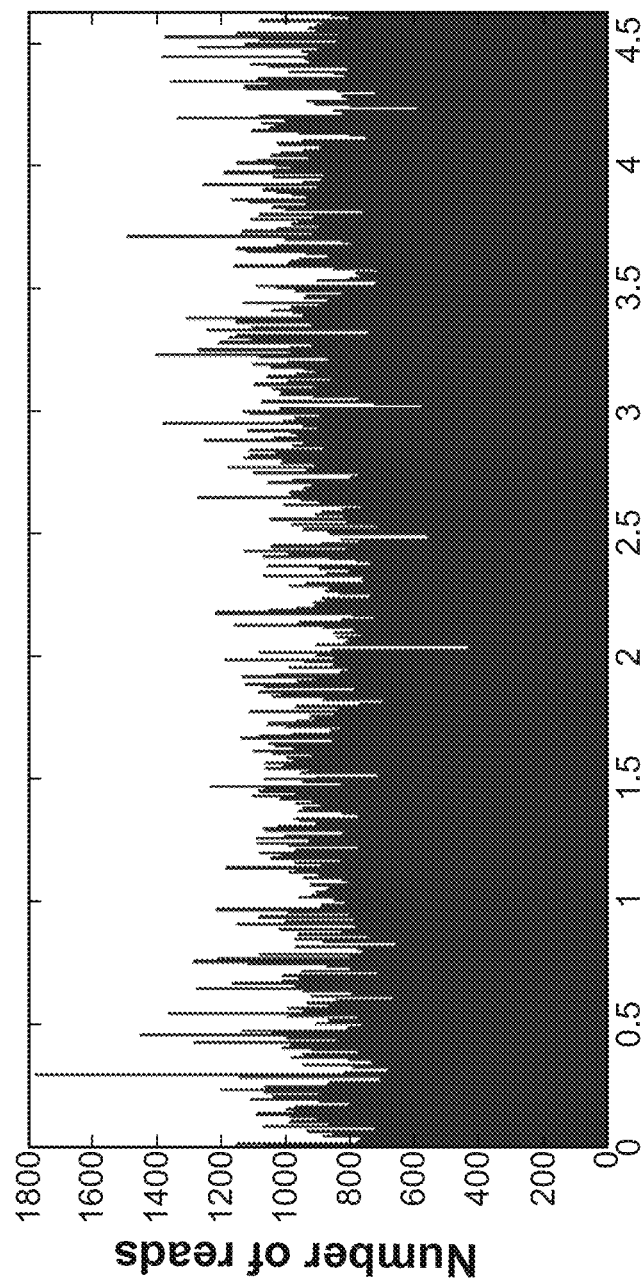
FIG. 22 shows coverage of *E. coli* genome with reads derived from in situ transposition method. X-axis=genomic coordinates. Y-axis=number of reads (10 Kb bins).

The results showed that in situ transposition may be successfully performed to introduce adaptor B into shotgun, A1/A2 adaptor-flanked HMW genomic DNA molecules that are pre-hybridized to the flow-cell. This is an improvement over the experiment described above and in FIGS. 13A and 13B, which involved only a single puc19 fragment. Mapping density across the *E. coli* genome of a representative experiment is shown in FIG. 22. The distribution is largely uniform, indicating that introduction of a cluster PCR compatible adaptor via in situ transposition does not result in overt biases in genomic representation.

Further, the conversion of library molecules into useful sequencing templates is currently quite inefficient. The data shown in FIG. 22 was from a single Illumina GA2x lane loaded with 10× the amount of usual template, but generated 100-fold fewer clusters than expected. Several reasons may explain this inefficiency, including: (a) Inefficient generation of properly tailed molecules: these approaches (FIG. 21) may be significantly less than 100% efficient in their conversion of target material to appropriately adapted molecules, and require further optimization; (b) Inefficient capture of 3' tailed dsDNA molecules to flow-cell primers: It is possible that additional manipulations of the flow-cell prior to cluster PCR (e.g. the transposase reaction; a wash including SDS to remove transposase, etc.) remove a substantial fraction of library molecules. (c) Failure of first strand synthesis on the flow-cell: Phusion DNA polymerase, which is normally used for first strand synthesis on the Illumina platform, has a very low strand displacement activity. Strand displacement during this first cycle is required for the method but not for conventional sequencing on this platform. Alternatives have shown, for example, that Bst polymerase can be substituted for Phusion for first strand synthesis on the flow-cell. (d) Transposase loading and/or in situ transposition is inefficient: Even if the molecules are hybridizing properly and first strand synthesis is successful, it won't form a cluster pair unless it receives at least one transposase insertion relatively proximal to an end.

Finally, although the data represented in FIG. 22 represents over 200,000 reads from a single lane, only a negligible fraction of these reads came from clusters that had a "paired read" from a neighboring cluster (as in FIGS. 13A and 13B). This problem may be related to the lower than expected densities of cluster formation (i.e. inefficient generation of molecules with proper tails at both ends, inefficient in situ transposition). Alternatively, this may be consequent to the relative rigidity of double-stranded DNA limiting both ends of a molecule with single-stranded tails from hybridizing to the surface.

Figure 24:
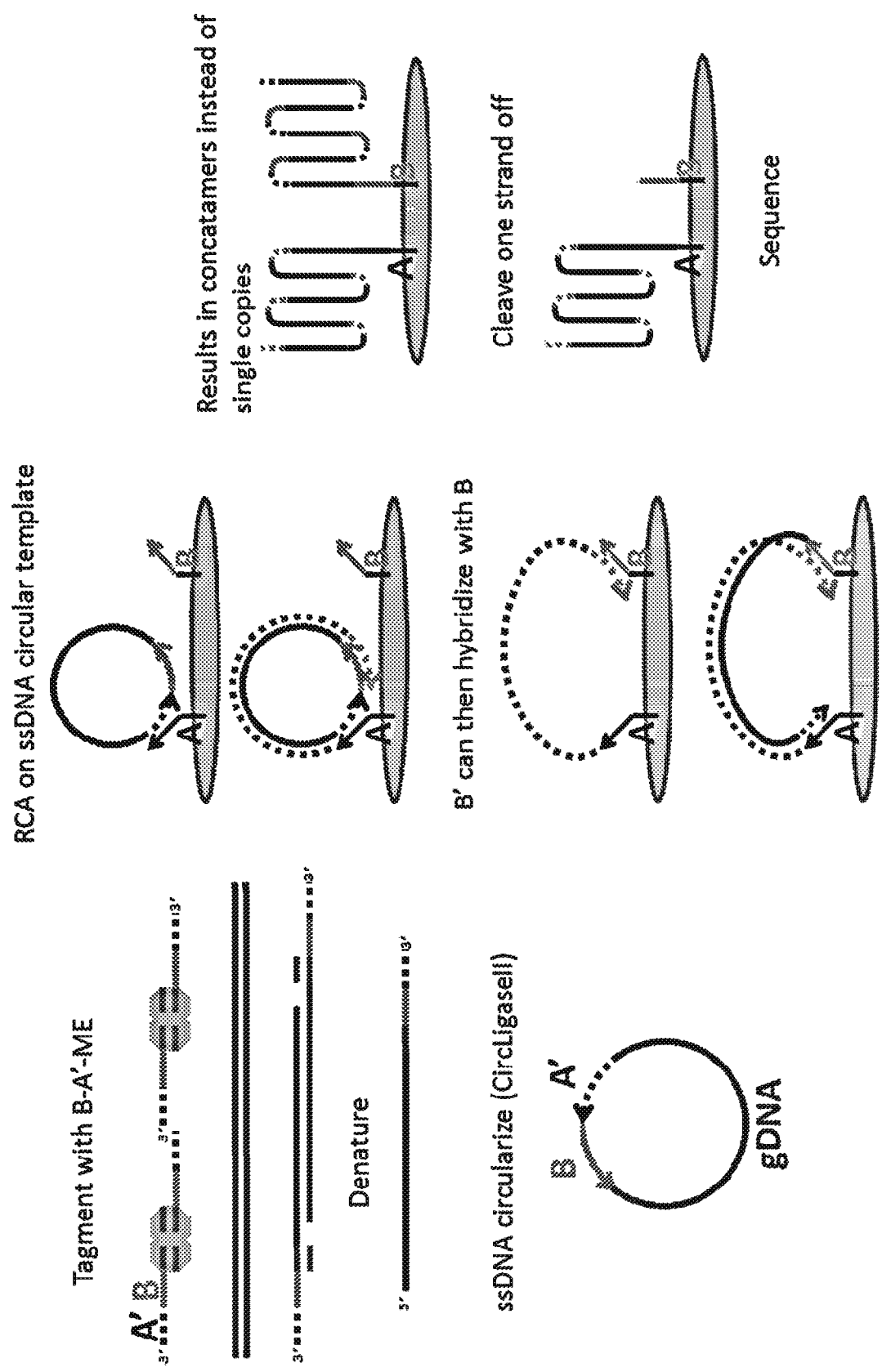
FIG. 24 illustrates the production of multiple displacing branching rolling circle amplification and polony (i.e., polymerase colony) formation according to some embodiments.

3.C. Transposase Followed by ssDNA Circularization and Multiple Displacing, Branching RCA In another embodiment, as shown in FIG. 24, transposase may be loaded with discontinuous oligos terminating in 5' phosphorylated A', followed by B and the dsDNA transposase recognition sequence. Transposition followed by denaturation will result in ssDNA terminating in a 5' phosphate, A', B, ME and then genomic DNA. Next, ssDNA circularization may be performed and then rolling-circle amplification (RCA) using flowcell bound A and B primers will result in multiple displacing branching rolling circle amplification and polony (i.e., polymerase colony) formation.

In an alternative embodiment, fosmids may be used in place of ssDNA which may result in long-range amplification and may allow production of 40 kb mate paired libraries.

3.D. Ordered Transposition Using Long ssDNA Backbones for DNA Nanoball Formation or Barcode Association In another embodiment, a circularized ssDNA template may be prepared using four primers (A, B, C, and D) interspersed with ~100 bp of filler DNA sequence and circularized (dsDNA sticky-end circularization, followed by selective digestion of one strand). Rolling-circle amplification (RCA) then results in long ssDNA molecules of repeating A, B, C, and D primer sites with intervening filler DNA sequences.

Next, a set of four differently loaded transposase complexes may be pooled where the first has complementarity to the A sequence and includes a mid-way cut site, and the other three are complementary to the B, C, and D sequences. Transpositon into genomic DNA likely allows for partial or complete insertions occurring in the A, B, C, and D order. After gap repair, the A restriction sites may be digested and the molecules circularized which results in circularized molecules of A, gDNA, B, gDNA, C, gDNA, D, gDNA. These molecules may then be used as templates in RCA that will generate DNA nanoballs containing 4 adaptor sites.

In an alternative embodiment, the original backbone template may be comprised of an adaptor flanked degenerate barcode with ~100 bp of filler sequence which is circularized, denatured, and subjected to RCA. The resulting backbone includes many repeats of the original template in succession. The transposase complexes are loaded with oligos that terminate in sequence complementary to the adaptors that flank the barcode where the transposase adaptors will anneal in a padlock formation. Gap repair of the degenerate region allows each transposome bound to any given backbone to have the same barcode. Transposition results in adjacent transposition events, likely occurring from transposomes of the same barcode, thereby allowing association of numerous reads with one original large progenitor molecule.

3.E. Direct Sequencing of Transposon Bubbles Containing Flowcell Primers

In another embodiment, a transposon that forms a "bubble" such as those described above may be inserted, wherein the bubble within the transposon includes primers complementary to flowcell bound primers as the bubble adaptors.

After insertion and subsequent gap repair, these long molecules can be directly hybridized to the flowcell either with or without stretching. Some portion of tandem transposons will be A and B' or A' and B which will be able to form clusters via standard bridge PCR methods. This will allow clusters originating proximal to one another will likely have arisen from the same high molecular weight progenitor molecule.

Alternatively, long molecules of known (to allow for an expected distance) or unknown length can have adaptors ligated to both ends containing a 5' overhang complementary to one of the flowcell primers. Transposition of a bubble transposon containing the other flowcell primer followed by gap repair will result in a molecule terminating in the complement to one flowcell primer and interspersed with the other. Hybridization to the flowcell with or without stretching will allow for the ends of the molecule to anneal. An initial displacing extension will copy through the transposon inserted second adaptor and produce the reverse complement. Subsequently, standard bridge PCR can be performed and after sequencing a proportion of proximal clusters will have arisen from the terminal ends of the original long molecule.

3.F. Transposomes Assembled on the Flowcell

In another embodiment, a flowcell is reprogrammed to include (1) oligos terminating in the transposase recognition sequence, or (2) bridge oligos that are hybridized that terminate in the transposase recognition sequence. The transposase is then added to the loading buffer and allowed to load the flowcell bound oligos.

Genomic DNA is then added to the transposase reaction buffer and wherever a molecule comes in contact with the flowcell, the immobilized transposase will attack at multiple positions along its length. After an initial extension, bridge PCR may be performed on the resulting fragments. Sequencing results in a portion of proximal clusters having arisen from the same large progenitor molecule.

In an alternative embodiment, long molecules may be added in which adaptors have been ligated containing one of the primer sequences that is not part of the flowcell-immobilized transposomes. Post transposition, one strand may be denatured and removed and the other is able to form clusters. A portion of resulting proximal clusters originate from the ends of the same large progenitor molecule.

Example 4: Low-Input Transposase Library Preparation for Bisulfite Sequencing

Figure 36A:
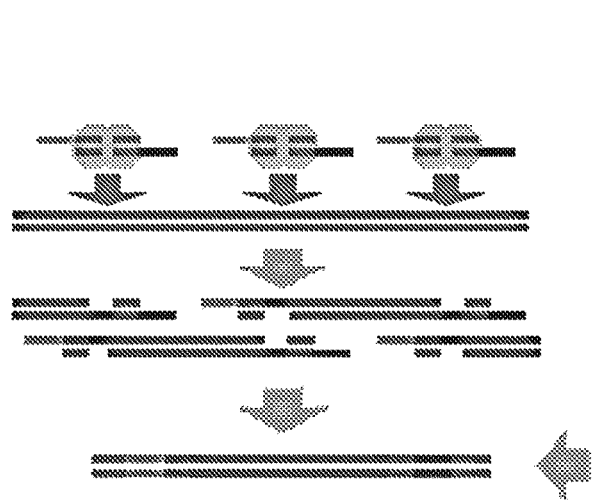
FIGS. 36A-36F the tn5mC-seq method and resulting methylation profiles according to one embodiment. (36A) Tagmentation-based DNA-seq library construction. Genomic DNA is attacked by transposase homodimers loaded with synthetic, discontinuous oligos (yellow, purple) that allow for fragmentation and adaptor incorporation in a single step. Subsequent PCR appends outer flowcell-compatible primers (pink, green). (36B) tnsmC-seq library construction. Loaded transposase attacks genomic DNA with a single methylated adaptor (yellow). An oligo-replacement approach anneals a second methylated adaptor (purple) which is then subject to gap-repair. Bisulfite treatment then converts unmethylated cytosine to uracil (orange) followed by PCR to append outer flowcell-compatible primers (pink, green). Methylation is represented as black lollipops. (36C) Coverage of cytosine positions genome-wide. >96% of Cs in all three contexts are covered at least once. Slight decrease in CpG coverage is due to reduced read alignment ability at regions with a high density of methylation. (36D) Normalized methylated cytosine over total cytosine positions in 10 kb windows across chromosome 12 (max set to 1.0), black box indicates centromere. (36E) Normalized methylated CpG over total CpG residues at annotated genic loci. Promoter is defined as 2 kb region upstream of TSS. (36F) Elevated CpG methylation levels in gene body (intron, exon) compared to intergenic regions.

As described above, a transposase-based in vitro shotgun library construction method ("tagmentation") that allows for construction of sequencing libraries from greatly reduced amounts of DNA (FIG. 36A) (Adey et al. 2010). Briefly, the method utilizes a hyperactive derivative of the Tn5 transposase loaded with discontinuous synthetic oligonucleotides to simultaneously fragment and append adaptors to genomic DNA. The resulting products are subjected to PCR amplification followed by high-throughput sequencing. The increased efficiency of genomic DNA conversion to viable amplicons and the greatly reduced number of steps allows the construction of low-bias, highly complex libraries from less than 50 nanograms of genomic DNA.

Figure 36B:
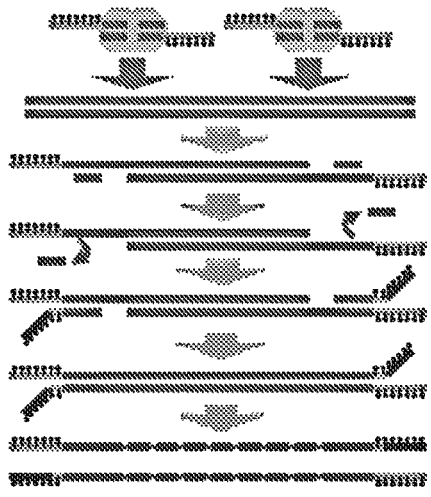

An approach, referred to herein as tn5mC-seq, that retains the advantages of transposase-based library preparation in the context of whole-genome bisulfite sequencing is described herein. Because the target of the transposition reaction is double-stranded DNA, whereas bisulfite treatment yields single stranded DNA, the method was extensively modified such that the tagmentation reaction could take place prior to bisulfite treatment (FIG. 36B). First, the adaptors to be incorporated were methylated at all cytosine residues to maintain cytosine identity during bisulfite treatment, with the exception of the 19 base-pair transposase recognition sequence (in order to minimize differential binding during transposome assembly). Second, an oligonucleotide replacement scheme (Grunenwald et al. 2011) was utilized to ensure that each strand would have adaptors covalently attached to both ends of the molecule. Specifically, this entails initial transposition with a single adaptor in which the double-stranded transposase recognition sequence is truncated to 16 base-pairs (Tm=36° C.), thereby facilitating its post-incorporation removal by denaturation. A second adaptor is then annealed and the gap repaired, resulting in each strand being covalently flanked by both a 3' and 5' adaptor. The fragmented, adapted, double-stranded genomic DNA is then subjected to standard bisulfite treatment for the conversion of unmethylated cytosine to uracil. This yields single-stranded, converted DNA that is PCR-amplified and sequenced.

Materials and Methods tn5mC-seq library construction and sequencing. Transposome complexes were generated by incubating 2.5 µl of 10 µM tn5mC-A1 (tn5mC-A1top: 5'-GAT [5mC] TA [5mC] A[5mC] G [5mC] [5mC] T [5mC] [5mC] [5mC] T [5mC] G [5mC] G [5mC] [5mC] AT [5mC] AGA GAT GTG TAT AAG AGA CAG-3', IDT (SEQ ID NO:1), annealed to tn5mC-A1bot: 5'-[Phos]-CTG TCT CTT ATA CAC A-3', IDT (SEQ ID NO:2), by incubating 10 µl of each oligo at 100 µM and 80 µl of EB (QIAGen) at 95° C. for 2 minutes then cooling to RT at 0.1° C./s) with 2.5 µl 100% glycerol and 5 µl Ez-Tn5 transposase (Epicentre—Illumina) for 20 minutes at RT.

Genomic DNA prepared from NA20847 cell lines was used at respective input quantities with 4 µl Nextera® HMW Buffer (Epicentre—Illumina), nuclease-free water (Ambion) to 17.5 µl and 2.5 µl prepared tn5mC transposomes (regardless of the quantity of DNA used). Reactions were incubated at 55° C. for 8 minutes in a thermocycler followed by SPRI bead cleanup (AMPure) using 36 µl of beads and the recommended protocol with elution in 14 µl nuclease-free water (Ambion). Adaptor 2 annealing was then carried out by adding 2 µl of 10× Ampligase Reaction Buffer (Epicentre—Illumina), 2 µl 10× dNTPs (2.5 mM each, Invitrogen), and 2 µl 10 µM tn5mC-A2top (IDT) to each reaction and incubating at 50° C. for 2 minutes followed by 45° C. for 10 minutes and cooling at 0.1° C./s to 37° C. and subsequent incubation for 10 minutes. Gap repair was then performed by adding 3 µl of Ampligase at 5 U/µl (Epicentre—Illumina) and 1 µl of either T4 DNA Polymerase (tn5mC libraries A-G, NEB) or Sulfolobus DNA Polymerase IV (tn5mC libraries H-J, NEB) and additional incubation at 37° C. for 30 minutes. Reactions were then cleaned up using SPRI beads (AMPure) according to recommended protocol using 36 µl beads and elution in 50 µl nuclease-free water (Ambion).

Bisulfite treatment was performed using an EZ DNA Methylation™ Kit (Zymo) according to recommended protocols with a 14 hour 50° C. incubation and 10 µl elution. Eluate was then used as the template for PCR using 12.5 µl Kapa 2G Robust HotStart ReadyMix (Kapa Biosystems), 1 µl 10 µM tn5mC-P1 (5'-[Phos]-CTG TCT CTT ATA CAC ATC TCT GAG [5mC] GGG [5mC] TGG [5mC] AAG G [5mC] AGA [5mC] [5mC] GAT [5mC]-3', IDT) (SEQ ID NO:3), 1 µl 10 µM Barcoded P2 (From Adey et. al. (2010)), 0.15 µl 100×SYBR Green (Invitrogen), and 0.35 µl nuclease-free water (Ambion). Thermocycling was carried out on a BioRad Opticon Mini real-time machine with the following parameters: 5:00@95° C.; (0:15@95° C.; 0:15@62° C.; 0:40@72° C.; Plate Read; 0:10@72° C.)×99. Reactions were monitored and removed from thermocycler as soon as plateau was reached (12-15 cycles).

Sequencing was carried out using either a full or partial lane on an Illumina HiSeq2000 using custom sequencing primers: Read 1: tn5mC-R1 (5'-GCC TCC CTC GCG CCA TCA GAG ATG TGT ATA AGA GAT AG-3', IDT) (SEQ ID NO:4), Index Read: tn5mC-Ix (5'-TTG TTT TTT ATA TAT ATT TCT GAG CGG GCT GGC AAG GC-3', IDT) (SEQ ID NO:5), Read 2: tn5mC-R2 (5'-GCC TTG CCA GCC CGC TCA GAA ATA TAT ATA AAA AAC AA-3', IDT) (SEQ ID NO:6). Read lengths were either single-read at 36 bp with a 9 bp index (SE36, libraries A and B, not included in table) or 101 bp paired-end with a 9 bp index (PE101, libraries C-J). Libraries were only sequenced on runs that did not have lanes containing Nextera® libraries as a precaution due to the similarity between sequencing primers.

Read Alignment.

The hg19 reference genome was first bisulfite-converted in silico for both the top (C changed to T, C2T) and bottom (G changed to A, G2A) strands. Prior to alignment reads were first filtered based on the run metrics, as several libraries were run on lanes in which instrument valve failures resulted in poor quality or reads consisting primarily of "N" bases. Next, reads were filtered to contain no more than 3 "N"s in the first 75 bases and subsequently aligned to both the C2T and G2A strands using BWA with default parameters. Reads that aligned to both strands were removed. Read pairs in which neither aligned to either strand were then pulled and trimmed to 76 bp (except for SE36 runs) and again aligned to both C2T and G2A strands. For library F, an initial trimming of 25 bp from the start of read 2 was performed due to instrument valve failure during those cycles. Duplicate reads (pairs sharing the same start positions for both reads 1 and 2) were removed and complexity determined. Reads with an alignment score<10 were then filtered out prior to secondary analysis. Total fold coverage was calculated using the total bases aligned from unique reads over the total alignable bases of the genome (slightly below 3 Gb per strand).

5mC Calling.

Methylated cytosines were called using a binomial distribution as in Lister et. al. (2009) whereby a probability mass function is calculated for each methylation context (CpG, CHG, CHH) using the number of reads covering the position as the number of trials and reads maintaining cytosine status as successes with a probability of success based on the total error rates which were determined by the combined non-conversion rate and sequencing error rate. The total error rate was initially determined by unmethylated lambda DNA spike-ins, however we found that the error rate estimation from the gap-repair portion of reads (as described in the main text) gave a more comprehensive estimate which was slightly higher than that of the lambda estimate, therefore to be conservative, we used the highest determined error rate at 0.009. If the probability was below the value of M, where M*(num. total unmethylated CpG)<0.01*(num. total methylated CpG), the position was called as being methylated, thus enforcing that no more than 1% of positions would be due to the error rate.

Results

Ultra-Low-Input Transposase-Based WGBS Library Performance.

tn5mC-seq was performed to sequence the methylome of a lymphoblastoid cell line (NA20847) using libraries constructed from 1 nanogram to 200 nanograms of input genomic DNA. Each library was barcoded during PCR amplification and subjected to either a spike-in (5%) or majority (80-90%) of a lane of sequencing on an Illumina HiSeq2000 (PE100; v2 chemistry). These data are summarized in Table 3, below.

TABLE 3

Summary of tn5mC-seq libraries and sequencing

| Name | Input DNA (ng) | Percent Aligning | Percent Unique | Unique Aligned Reads | Mean Insert Size (bp) |
|---|---|---|---|---|---|
| tn5mC-C | 200 | 68 | 93 | 127,098,152 | 198 |
| tn5mC-D | 50 | 75 | 90 | 133,383,834 | 254 |
| tn5mC-E* | 1 | 12 | 76 | 11,181,960 | 134 |
| tn5mC-F* | 10 | 65 | 95 | 118,170,302 | 168 |
| tn5mC-G* | 50 | 61 | 97 | 87,294,793 | 180 |
| tn5mC-H | 1 | 11 | 78 | 12,393,357 | 126 |
| tn5mC-I** | 10 | 62 | n/a | 29,546,077 | n/a |
| tn5mC-J | 50 | 71 | 95 | 132,144,644 | 196 |
| TOTAL | | | | 651,213,119 | |

*Valve failures in Read 2 resulted in extensive read trimming (50-70 bp)
**Complete valve failure on Read 2.

Raw reads were initially filtered for instrument valve failures at specific locations of reads and then removal of reads containing over three Ns or extremely low quality bases (phred score<=2) in the first 50 bases. Alignment was then performed using BWA (Li and Durbin 2009) to in silico converted top and bottom strand references of hg19 (GRC37) followed by trimming and re-alignment. Duplicate reads were identified and removed according to their start position and insert size. The percentage of post-filtering reads that align for each library is shown, as is the percentage of these that are non-duplicates.

Reads were aligned to an in silico converted hg19 (GRC37) to both the top (C=>T) and bottom (G=>A) strands using BWA (Li and Durbin 2009) followed by read trimming of unmapped reads and secondary alignment using the same parameters. Because unmethylated nucleotides are incorporated during the gap-repair step (first 9 base-pairs of the second read and last 9 base-pairs before the adaptor as determined by insert size on the first read), the gap-repair regions must be excluded from methylation analysis. However, these bases also serve as an internal control for the conversion rate of the bisulfite treatment. This was found to be >99% for all libraries, and this was independently confirmed using unmethylated lambda DNA spike-ins to two libraries.

Figure 36C:
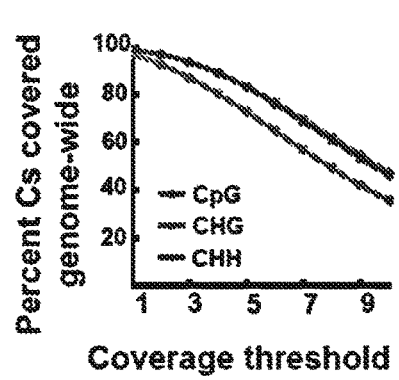

For each library constructed using 0 nanograms of genomic DNA, over 100 million aligned reads were obtained (60-75% of total filtered reads; see Methods) of high complexity (90-97% non-duplicates). Despite the significantly reduced performance of libraries prepared from 1 nanogram, approximately 12 million reads were still aligned and the library was of reasonable complexity (78% non-duplicates). Post-alignment reads were merged and quality filtered for a total of 51.7 gigabases of aligned, unique sequence. The average read depth was 8.6× per strand with >96% of CpG and >98% of non-CpG cytosines covered genome-wide (FIG. 36C).

Lymphoblastoid Cell Line Methylation.

Figure 36D:
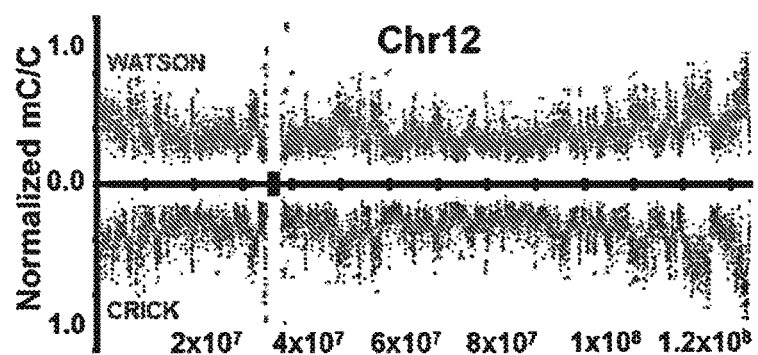
Figure 36E:
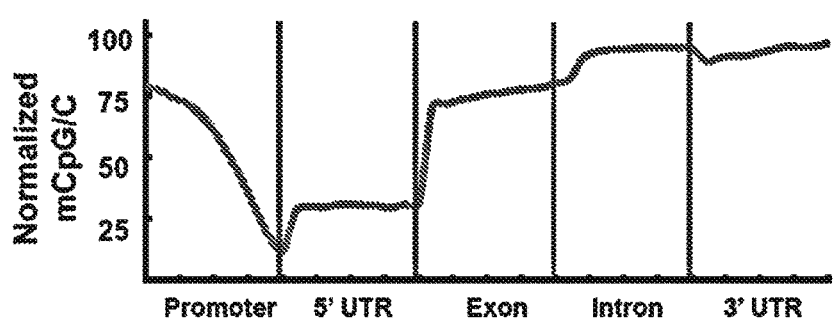
Figure 36F:
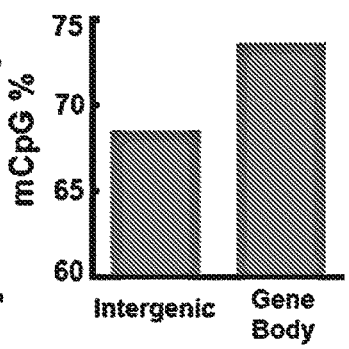

Approximately 46 million 5mC positions (1% FDR; see Methods) were detected, accounting for 4.2% of total cytosines with coverage. The majority of methylation observed was in the CpG context (97.1%), and the global CpG methylation level was 69.1%. This level is similar to that of the fetal fibroblast cell line IMR90 sequenced by Lister and colleagues (Lister et al. 2009) (67.7%), and consistent with the observation that CpG methylation levels are reduced in differentiated cell types. Additionally, CHG and CHH methylation levels were substantially lower than in ES cells, at 0.36% and 0.37% respectively, again consistent with the differentiated cell type. On the chromosome scale, the methylation was greater in sub-telomeric regions (FIG. 36D), as expected by the miRNA-mediated pathways that act to control telomere length (Benetti et al. 2008). An analysis of functionally annotated genic regions revealed a sharp decrease in CpG methylation through the promoter region followed by a minor increase in the 5'UTR and then elevated levels of methylation throughout the gene body, particularly at introns (FIGS. 36E and 36F), consistent with previously described CpG methylation profiles (Lister et al. 2009).

Discussion tn5mC-seq was developed as a novel method for rapidly preparing complex, shotgun bisulfite sequencing libraries for WGBS. In brief, the method utilizes a hyperactive Tn5 transposase derivative to fragment genomic DNA and append adaptors in a single step, as previously characterized for the construction of DNA-seq libraries (Adey et al. 2010). In order for library molecules to withstand bisulfite treatment, the adaptors are methylated at all cytosine residues and an oligonucleotide replacement strategy is employed to make each single-strand covalently flanked by adaptors. The high efficiency of the transposase and overall reduction in loss-associated steps permits construction of high quality bisulfite sequencing libraries from as little as 10 ng as well as useful sequence from 1 ng of input DNA.

These results illustrate how derivatives of the transposase-based method for DNA-Seq library preparation enable important applications of next-generation sequencing where its advantages are perhaps even more relevant. The ability to generate such libraries from very low amounts of input genomic DNA substantially improves the practicality of whole methylome sequencing, and removes an important advantage of less comprehensive methods such as RRBS (Meissner et al. 2005; Harris et al. 2010). Specifically, low-input WGBS with tn5mC-seq may make possible the comprehensive interrogation of methylation in many contexts where DNA quantity is a bottleneck, e.g. developing anatomical structures, microdissected tissues, or pathologies such as cancer, where the epigenetic landscape is of interest but tissue quantity limits resolution.

Example 5: Identifying Distant Regulatory Sites and Measuring Chromosome Conformation Recent studies have shown the importance and complexity of physical interactions between genetic elements within a genome. Measuring these interactions can help to explain how distant cis and trans regulatory DNA plays a role in gene regulation (including which genes are affected by which enhancers, how chromosomes are arrayed within a cell, how certain transcription factors like AR and ER bind and influence gene expression). It can also provide clues to the formation of the rearrangements and inversions involved in cancer and other genetic diseases.

Current methods of assaying physical interactions using high throughput sequencing include chromatin interaction analysis using paired end tag sequencing (ChIA-PET; interactions of transcription factor-binding sites) and Hi-C (method of producing maps of genome). Both approaches have limitations that can be attributed to the low efficiency and specificity of intramolecular ligation, which the methods use to pair distant regions of DNA together for sequencing. Such a ligation step requires large amounts of input DNA (100+ ug) and can result in technical artifacts in which fragments of DNA are ligated to each other even when they are not typically associated with each other.

These problems are important when trying to understand the genomic architecture of a small population of cells, like embryonic stem cells and cancer cells. It also means that any inferences of DNA interactions resulting from transcription factor binding that are measured are on average of extremely large cell populations (e.g., $10^8$ cells or ~500 micrograms of DNA). Given that different cells can have different genomic architectures or patterns of transaction factor binding, an approach that requires less starting DNA may be useful.

Figure 28:
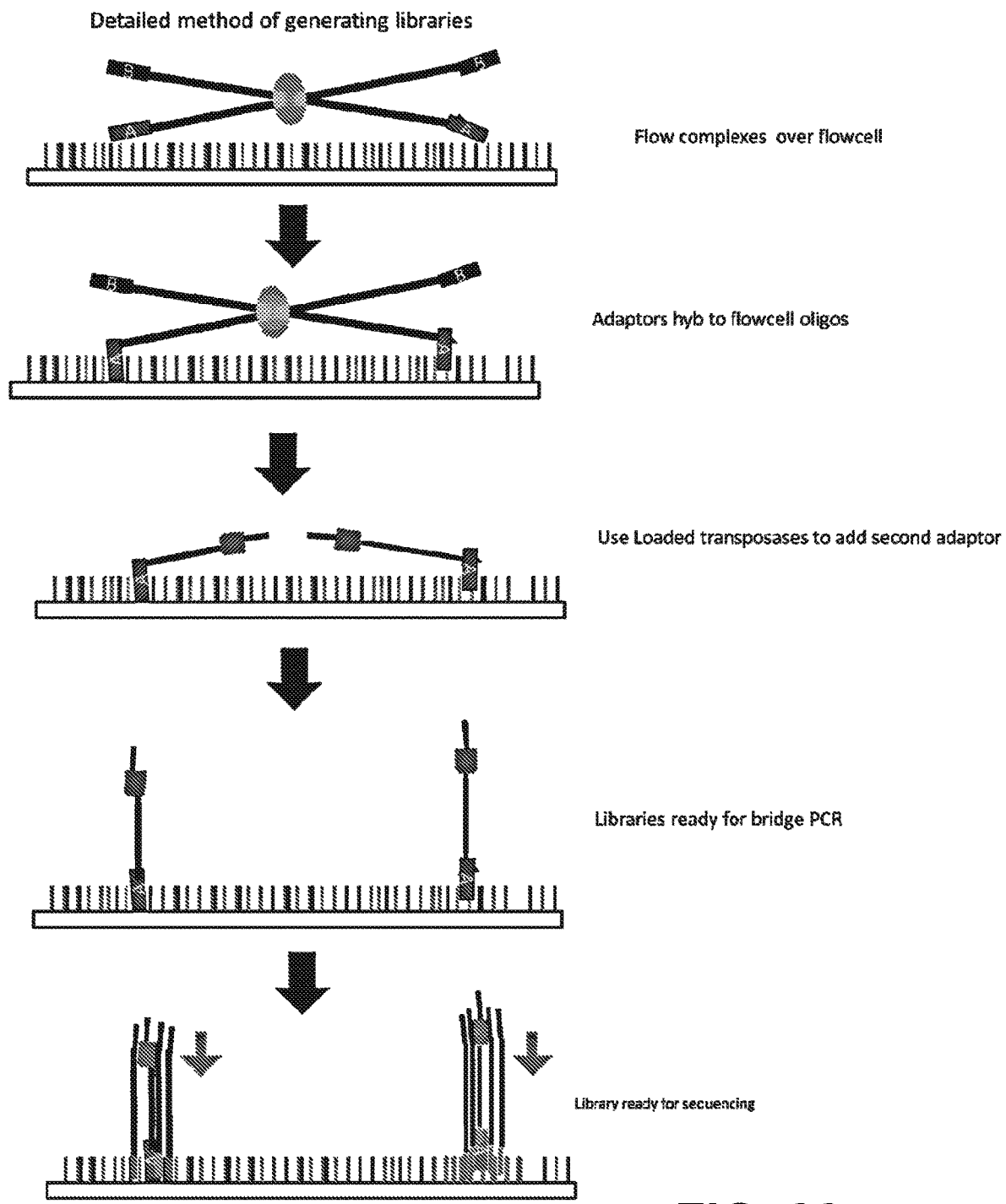
FIG. 28 illustrates a method used to generate clusters on flowcell: Any combination of the four arms could hybridize to the flowcell and generate a library. In this case, only two arms do.

Therefore, methods for measuring DNA-DNA and DNA-protein interactions within smaller populations of cells are provided below. Such methods use the "infinipair" technology (described in example 3A above) to directly sequence multiple fragments off of immunoprecipitated DNA that has been crosslinked (FIG. 28). These methods differ from the CHIA-PET and Hi-C methods because they directly assay crosslinked fragments of DNA without the extra step of intramolecular ligation.

5.A. Identification of Distant Regulatory Binding Sites

Figure 29:
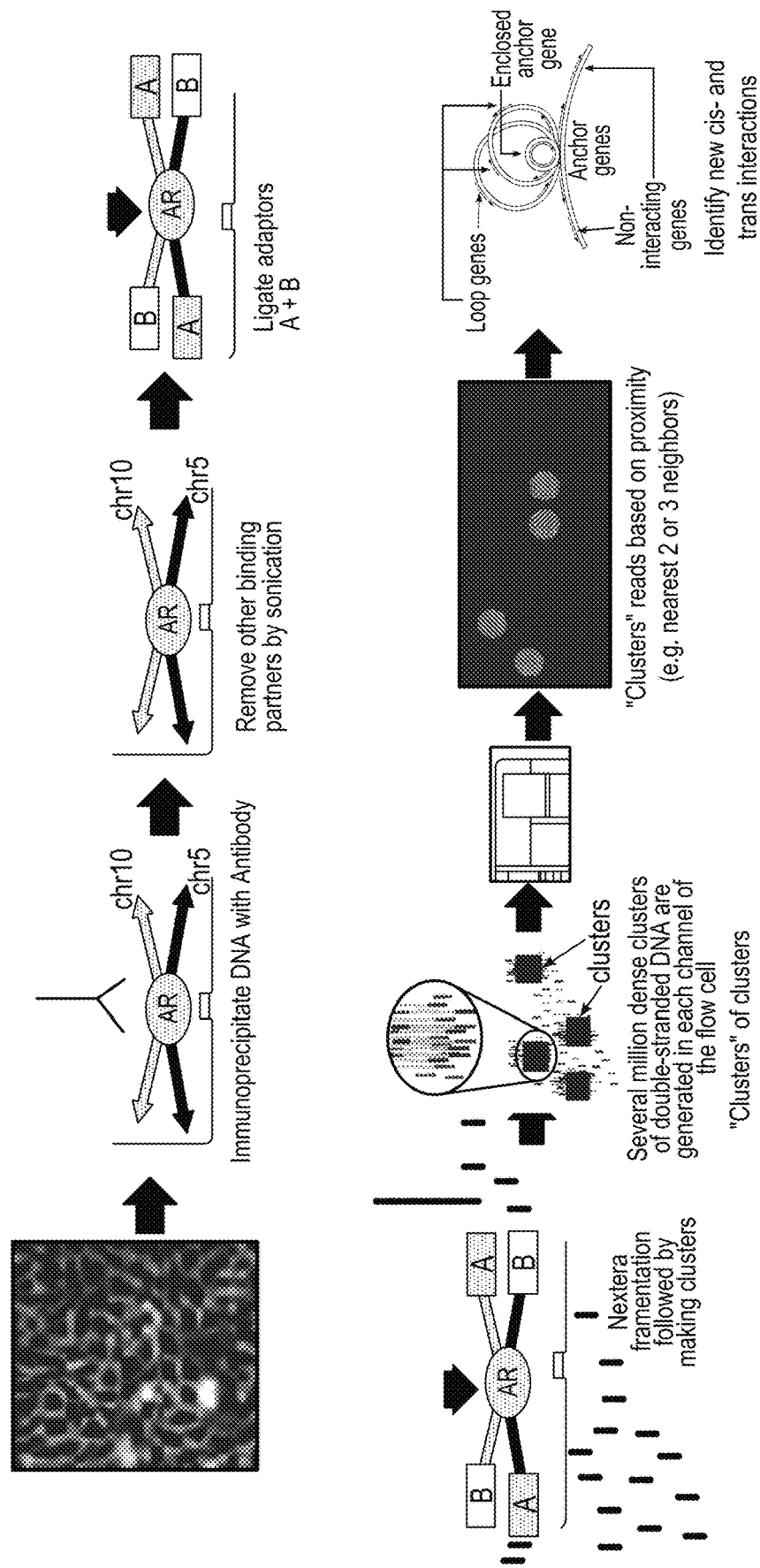
FIG. 29 illustrates a method that uses "infinipair" to identify interactions between transcription factor binding sites. Cells may be cross linked with formaldehyde subjected to ChIP to pull down DNA:protein complexes. Modified sequencing adaptors may be ligated onto the complexes and used to generate infinipair clusters. The reads may be clustered using "infinipair" technology and used to match clusters. Identification of new cis and trans interactions may be identified using previously described methods (16).

In one embodiment, modifications of the technology described in example 3A (referred to herein as the "inifinpair" technology) may be used to identify interactions between transcription factor (TF) binding sites, such as, for example, those found on the Estrogen receptor. As shown in FIG. 29, approximately $10^4$ cells are induced with hormone (~10 ng), followed by chromatin immunoprecipitation of the cells. Next, the chromatin fibers are broken by cross-linking the cells with 1% formaldehyde followed by sonication. An ER/AR/receptor specific antibody is then used to enrich binding chromatin fragments.

Next, end repair is performed using T4 polymerase to ligate to A+B adaptors. No phosphorylation, ligation of half linkers or dilution of ligation is necessary in this method. The infinipair technology is then used to generate clusters corresponding to immunoprecipitated complexes. Neighboring clusters are paired together to create a list of interactions between chromosomal positions.

To narrow down the list of putative interactions, the data collected is then intersected with CHIP-Seq information, which provides information on known binding sites of transcription factors. Information from multiple libraries is overlapped to increase confidence in called interactions. The structure of the chromatin interactions is characterized using this data, and is also used to link regulatory regions to DNA (i.e link genes to enhancers).

Some of the benefits of using this method may include, but are not limited to, (1) Higher accuracy in pairing interactions—(no inter-fragment ligation), (2) Lower input DNA required, resulting in more applications may be used (i.e., interactions within smaller sets of samples (ES cells/cancer cells/smaller groups of healthy cells) may be identified, (3) Easier workflow—no dilute ligations, no PCR, no MmeI digestions etc., and (4) Less sequencing required.

5.B. Inferring Chromosome Conformation

Figure 30:
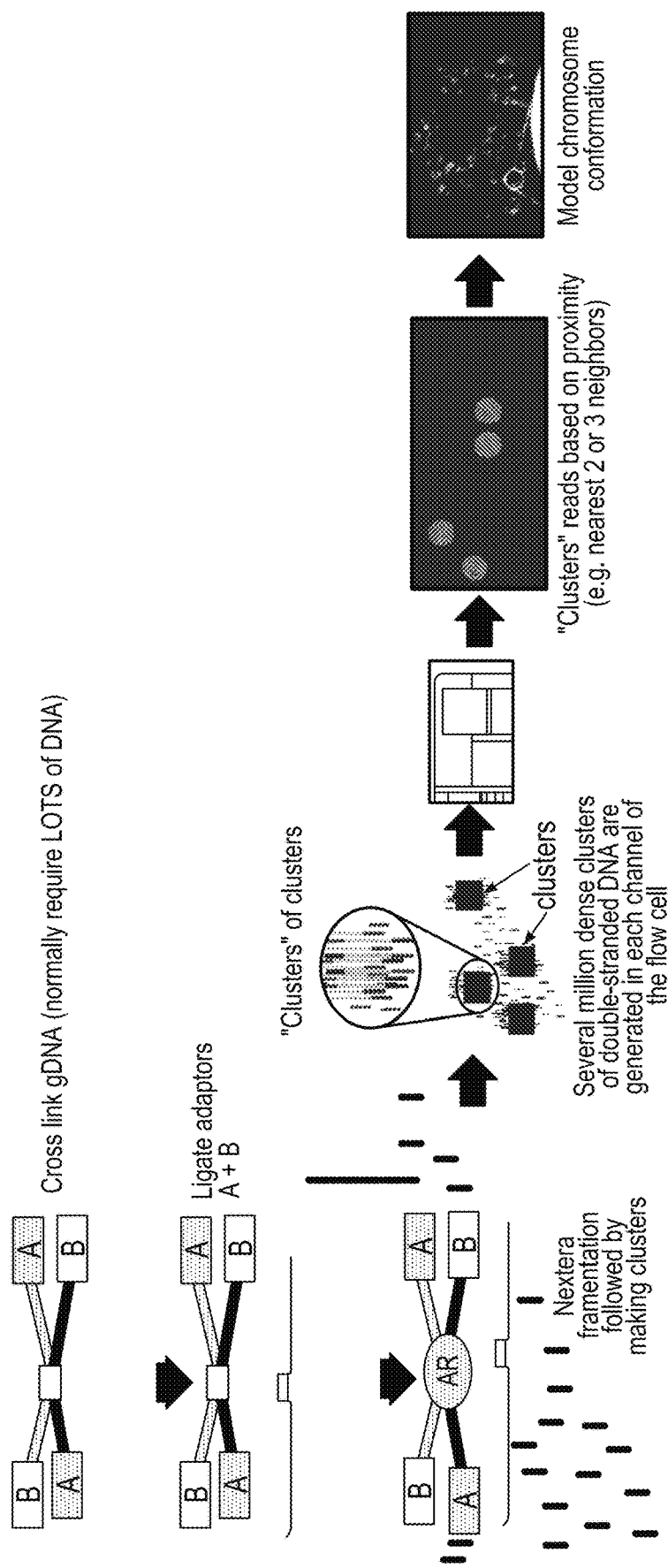
FIG. 30 illustrates a method using infinipair to model chromosome conformation in small numbers of cells.

In another embodiment, infinipair technology is used to model chromosome conformation in small numbers of cells. Previous methods such as the Hi-C method required a larger number of cells (~$10^7$ cells; ~50 ug DNA). As shown in FIG. 30, genomic DNA is cross linked. The cells are lysed using a homogenizer and the chromatin is then spun down. Chromatin proteins are removed by incubating in 1% SDS followed by Triton X-100. Chromatin is then digested by incubating in HindIII overnight.

Chromatin is purified using columns with beads directed against an anti-chromatin antibody. A and B adaptors are then ligated to DNA fragments without the need to biotinylate. Next, the infinipair technology is used to generate inifinipair clusters corresponding to complexes. Neighboring clusters are paired together to create a list of interactions between chromosomal positions. The information generated is then used to generate 3 dimensional models and to better understand the conformation of specific cell types.

Example 6: Integration of Short-Range, Mid-Range and Long-Range Contiguity for a More Cost-Effective Sequencing Method The focus of this Example includes 1) integrating methods developed in Examples 1-3 for the high-quality de novo assembly of the mouse genome; 2) integrating these same methods for the haplotype-resolved resequencing of a human genome; and 3) extending compatibility to other next-generation sequencing paradigms.

6.A. Cost Analysis and the Path to the $1,000 Mark

An important aspect of the methods described herein is that the costs are almost entirely dependent on the costs of the sequencing platform with which they are integrated. If "X" is the cost of genome resequencing, then the cost the methods described herein can be abstracted as "a+bX", where "a" is the fixed cost per sample of capturing contiguity information (e.g. the cost of an in situ transposition reaction), and "b" is the proportion of sequencing required to recover that information relative to genome resequencing. Estimates for "a" are low, i.e. less than $30 per method. This is because reactions such as in situ transposition and PCR manipulate genomic DNA en masse within single reagent volumes. Furthermore, reagents such as degenerate oligonucleotides and microfluidic devices are relatively inexpensive, and their costs can be amortized over many uses. The value of "b" is more difficult to predict, and is dependent on the extent of success in implementing and optimizing each method. However, it is noted that the barcodes themselves are short as compared to the primary reads with which they are in cis (e.g. SE25 barcode versus PE76 primary).

Sequencing costs associated with each of the following application of the methods described herein should be roughly the same as the cost of 40× resequencing of a mammalian genome with the same platform, i.e. "b≈1". As demonstrated by the original assemblies of the mouse and human genomes, it is possible to achieve a high quality de novo assembly of a mammalian genome with substantially less sampling than is currently used for genome resequencing, provided that sufficient contiguity information is also obtained.

6.B. De Novo Assembly of the Mouse Genome

Using the contiguity information obtained from the methods described above, a high-quality de novo assembly of a mammalian genome may be obtained de novo To accomplish this, existing tools for either conventional or 'next-generation' de novo assembly (Schatz et al. 2010) will be repurposed and applied to these data, and additional software will be developed as necessary. To minimize costs without significantly compromising quality, the optimal mix of contiguity mapping methods (i.e. at different scales) will be determined. This may require, for example, oversampling the genome with each contiguity mapping method, and then downsampling to include different proportions of data from each method and evaluating the impact on the quality of de novo assembly. Focusing on the de novo assembly of the mouse genome as a test case, the contiguity of the original assembly (i.e. contig N50 of 24.8 Kb; supercontig N50 of 16.9 Mb) will be exceeded with the same amount of data as is required for 40× resequencing (2.5 Gb×40=~100 Gb), i.e. "b≈1". Initially, sequencing costs will predominate, i.e. "bX>>a", but even as this changes the total costs of preparatory reactions ("a") should be kept to <$100, even if all scales of contiguity mapping methods are used (i.e. Short-Range, Mid-Range and Long-Range Contiguity).

6.C. Haplotype Resolved Resequencing of a Human Genome

Preliminary data (2.D) shows that a modest amount of contiguity information may provide extensive haplotype resolving power. For this data, the software required for haplotype-resolved genome resequencing has been developed or will be developed. Additionally, algorithms will be developed to discover SNPs resolve haplotypes using the same data, as accurately calling haploid genotypes requires less than half as much sequencing as calling diploid genotypes. Contiguity mapping methods will be integrated to resequence and simultaneously haplotype resolve a human genome, with a target of >95% coverage in haplotype-resolved blocks with an N50 of at least 1 Mb while maintaining >99.5% concordance with HapMap data at D'>0.90. As with de novo assembly of the mouse genome, this may be achieved with the same amount of sequencing as would be required for 40× haplotype-blind resequencing of the human genome (3 Gb×40=~120 Gb), i.e. "b≈1".

6.D. Extending the Compatibility of Contiguity Mapping Methods to Other Sequencing Paradigms Although the methods for capturing contiguity information as described herein are directed to being used with the sequencing technologies with which they are integrated, such methods may be developed for other sequencing technologies and with other sequencing platforms. These include other cyclic-array platforms (e.g. Polonator, SOLiD), as well as emerging paradigms such as nanopore sequencing.

REFERENCES

The references, patents and published patent applications listed below, and all references cited in the specification above are hereby incorporated by reference in their entirety, as if fully set forth herein.

Adey A, Morrison H G, Asan, Xun X, Kitzman J O, Turner E H, Stackhouse B, MacKenzie A P, Caruccio N C, Zhang X et al. 2010. Rapid, low-input, low-bias construction of shotgun fragment libraries by high-density in vitro transposition. Genome Biol 11(12): R119.

Ball M P, Li J B, Gao Y, Lee J H, LeProust E M, Park I H, Xie B, Daley G Q, Church G M. 2009. Targeted and genome-scale strategies reveal gene-body methylation signatures in human cells. Nat Biotechnol 27(4): 361-368.

Bansal V, Bafna V. HapCUT: an efficient and accurate algorithm for the haplotype assembly problem. Bioinformatics. 2008; 24(16):i153-9.

Benetti R, Gonzalo S, Jaco I, Munoz P, Gonzalez S, Schoeftner S, Murchison E, Andl T, Chen T, Klatt P et al. 2008. A mammalian microRNA cluster controls DNA methylation and telomere recombination via Rbl2-dependent regulation of DNA methyltransferases. Nat Struct Mol Biol 15(3): 268-279.

Bentley D R, Balasubramanian S, Swerdlow H P, Smith G P, Milton J, Brown C G, et al. Accurate whole human genome sequencing using reversible terminator chemistry. Nature. 2008; 456(7218):53-9. PMCID: PMC2581791.

Branton D, Deamer D W, Marziali A, Bayley H, Benner S A, Butler T, et al. The potential and challenges of nanopore sequencing. Nat Biotechnol. 2008; 26(10):1146-53. PMCID: PMC2683588.

Braslaysky I, Hebert B, Kartalov E, Quake S R. Sequence information can be obtained from single DNA molecules. Proc Natl Acad Sci USA. 2003; 100(7):3960-4. PMCID: PMC153030.

Clark S J, Harrison J, Paul C L, Frommer M. 1994. High sensitivity mapping of methylated cytosines. Nucleic Acids Res 22(15): 2990-2997.

Cokus S J, Feng S, Zhang X, Chen Z, Merriman B, Haudenschild C D, Pradhan S, Nelson S F, Pellegrini M, Jacobsen S E. 2008. Shotgun bisulphite sequencing of the *Arabidopsis* genome reveals DNA methylation patterning. Nature 452(7184): 215-219.

Deng J, Shoemaker R, Xie B, Gore A, LeProust E M, Antosiewicz-Bourget J, Egli D, Maherali N, Park I H, Yu J et al. 2009. Targeted bisulfite sequencing reveals changes in DNA methylation associated with nuclear reprogramming. Nat Biotechnol 27(4): 353-360.

Down T A, Rakyan V K, Turner D J, Flicek P, Li H, Kulesha E, Graf S, Johnson N, Herrero J, Tomazou E M et al. 2008. A Bayesian deconvolution strategy for immunoprecipitation-based DNA methylome analysis. Nat Biotechnol 26(7): 779-785.

Dressman D, Yan H, Traverso G, Kinzler K W, Vogelstein B. Transforming single DNA molecules into fluorescent magnetic particles for detection and enumeration of genetic variations. Proc Natl Acad Sci USA. 2003; 100 (15):8817-22. PMCID: PMC166396.

Drmanac R, Sparks A B, Callow M J, Halpern A L, Burns N L, Kermani B G, et al. Human genome sequencing using unchained base reads on self-assembling DNA nanoarrays. Science. 2009; 327(5961):78-81.

Duan Z, Andronescu M, Schutz K, McIlwain S, Kim Y J, Lee C, et al. A three-dimensional model of the yeast genome. Nature 2010; 465(7296):363-7. PMCID: PMC2874121.

Eid J, Fehr A, Gray J, Luong K, Lyle J, Otto G, et al. Real-time DNA sequencing from single polymerase molecules. Science. 2009; 323(5910):133-8.

Fan H C, Wang J, Potanina A, & Quake S R (2011) Whole-genome molecular haplotyping of single cells. Nat Biotech 29(1):51-57.

Fullwood, M. J. et al. An oestrogen-receptor-α-bound human chromatin interactome. Nature 462, 58-64 (2009).

Geiss G K, Bumgarner R E, Birditt B, Dahl T, Dowidar N, Dunaway D L, et al. Direct multiplexed measurement of gene expression with color-coded probe pairs. Nat Biotechnol. 2008; 26(3):317-25.

Gnerre S, Maccallum I, Przybylski D, Ribeiro F J, Burton J N, Walker B J, Sharpe T, Hall G, Shea T P, Sykes S, Berlin A M, Aird D, Costello M, Daza R, Williams L, Nicol R, Gnirke A, Nusbaum C, Lander E S, Jaffe D B. High-quality draft assemblies of mammalian genomes from massively parallel sequence data. Proc Natl Acad Sci USA. 2010 Dec. 27. [Epub ahead of print] PubMed PMID: 21187386.

Grunenwald H, Baas B, Goryshin I, Zhang B, Adey A, Hu S, Shendure J, Caruccio N, Maffitt M. 2011. Nextera PCR-Free DNA Library Preparation for Next-Generation Sequencing. (Poster Presentation, AGBT).

Gu H, Smith Z D, Bock C, Boyle P, Gnirke A, Meissner A. 2011. Preparation of reduced representation bisulfite sequencing libraries for genome-scale DNA methylation profiling. Nat Protoc 6(4): 468-481.

Harris R A, Wang T, Coarfa C, Nagarajan R P, Hong C, Downey S L, Johnson B E, Fouse S D, Delaney A, Zhao Y et al. 2010. Comparison of sequencing-based methods to profile DNA methylation and identification of monoallelic epigenetic modifications. Nat Biotechnol 28(10): 1097-1105.

Hiatt J B, Patwardhan R P, Turner E H, Lee C, Shendure J. Parallel, tag-directed assembly of locally derived short sequence reads. Nat Methods. 2010; 7(2):119-22. PMCID: 2848820.

http://www.epibio.com/nextera/nmeth_f_269.pdf.

Johnson D S, Mortazavi A, Myers R M, Wold B. Genome-wide mapping of in vivo protein-DNA interactions. Science. 2007; 316(5830):1497-502.

Kidd J M, Cooper G M, Donahue W F, Hayden H S, Sampas N, Graves T, et al. Mapping and sequencing of structural variation from eight human genomes. Nature. 2008; 453 (7191):56-64. PMCID: PMC2424287.

Kitzman J O, Mackenzie A P, Adey A, Hiatt J B, Patwardhan R P, Sudmant P H, Ng S B, Alkan C, Qiu R, Eichler E E, Shendure J. Haplotype-resolved genome sequencing of a Gujarati Indian individual. Nat Biotechnol. 2011 January; 29(1):59-63. Epub 2010 Dec. 19. PubMed PMID: 21170042.

Kitzman J O, et al. (2011) Haplotype-resolved genome sequencing of a Gujarati Indian individual. Nat Biotech 29(1):59-63.

Lai Z, Jing J, Aston C, Clarke V, Apodaca J, Dimalanta E T, et al. A shotgun optical map of the entire *Plasmodium falciparum* genome. Nat Genet. 1999; 23(3):309-13.

Lander E S, Linton L M, Birren B, Nusbaum C, Zody M C, Baldwin J, et al. Initial sequencing and analysis of the human genome. Nature. 2001; 409(6822):860-921.

Levy S, Sutton G, Ng P C, Feuk L, Halpern A L, Walenz B P, et al. The diploid genome sequence of an individual human. PLoS Biol. 2007; 5(10):e254. PMCID: PMC1964779.

Li R, Zhu H, Ruan J, Qian W, Fang X, Shi Z, et al. De novo assembly of human genomes with massively parallel short read sequencing. Genome Res. 2010; 20(2):265-72. PMCID: PMC2813482.

Li Y, Kim H J, Zheng C, Chow W H, Lim J, Keenan B, et al. Primase-based whole genome amplification. Nucleic Acids Res. 2008; 36(13):e79. PMCID: PMC2490742.

Li H, Durbin R. 2009. Fast and accurate short read alignment with Burrows-Wheeler transform. Bioinformatics 25(14): 1754-1760.

Li Y, Zhu J, Tian G, Li N, Li Q, Ye M, Zheng H, Yu J, Wu H, Sun J et al. 2010. The DNA methylome of human peripheral blood mononuclear cells. PLoS Biol 8(11): e1000533.

Lieberman-Aiden E, van Berkum N L, Williams L, Imakaev M, Ragoczy T, Telling A, et al. Comprehensive mapping of long-range interactions reveals folding principles of the human genome. Science. 2009; 326(5950):289-93. PMCID: PMC2858594.

Lim A, Dimalanta E T, Potamousis K D, Yen G, Apodoca J, Tao C, et al. Shotgun optical maps of the whole *Escherichia coli* O157:H7 genome. Genome Res. 2001; 11(9): 1584-93. PMCID: PMC311123.

Lin J, Qi R, Aston C, Jing J, Anantharaman T S, Mishra B, et al. Whole-genome shotgun optical mapping of Deinococcus radiodurans. Science. 1999; 285(5433):1558-62.

Lister R, Pelizzola M, Dowen R H, Hawkins R D, Hon G, Tonti-Filippini J, Nery J R, Lee L, Ye Z, Ngo Q M et al. 2009. Human DNA methylomes at base resolution show widespread epigenomic differences. Nature 462(7271): 315-322.

Margulies M, Egholm M, Altman W E, Attiya S, Bader J S, Bemben L A, et al. Genome sequencing in microfabricated high-density picolitre reactors. Nature. 2005; 437 (7057):376-80. PMCID: PMC1464427.

Mazutis L, Araghi A F, Miller O J, Baret J C, Frenz L, Janoshazi A, et al. Droplet-based microfluidic systems for high-throughput single DNA molecule isothermal amplification and analysis. Anal Chem. 2009; 81(12):4813-21.

Meissner A, Gnirke A, Bell G W, Ramsahoye B, Lander E S, Jaenisch R. 2005. Reduced representation bisulfite sequencing for comparative high-resolution DNA methylation analysis. Nucleic Acids Res 33(18): 5868-5877.

Mitra R D, Shendure J, Olejnik J, Edyta Krzymanska O, Church G M. Fluorescent in situ sequencing on polymerase colonies. Anal Biochem. 2003; 320(1):55-65.

Mortazavi A, Williams B A, McCue K, Schaeffer L, Wold B. Mapping and quantifying mammalian transcriptomes by RNA-Seq. Nat Methods. 2008; 5(7):621-8.

MGSC (2002) Initial sequencing and comparative analysis of the mouse genome. Nature 420(6915):520-562.

Ng S B, Turner E H, Robertson P D, Flygare S D, Bigham A W, Lee C, et al. Targeted capture and massively parallel sequencing of 12 human exomes. Nature. 2009; 461 (7261):272-6. PMCID: PMC2844771.

Ramanathan A, Huff E J, Lamers C C, Potamousis K D, Forrest D K, Schwartz D C. An integrative approach for the optical sequencing of single DNA molecules. Anal Biochem. 2004; 330(2):227-41.

Riehn R, et al. (2005) Restriction mapping in nanofluidic devices. Proceedings of the National Academy of Sciences of the United States of America 102(29):10012-10016. Schatz M C, Delcher A L, Salzberg S L. Assembly of large genomes using second-generation sequencing. Genome Res. 2010; 20(9):1165-73. PMCID: PMC2928494.

Ritz A, Bashir A, Raphael B J. Structural variation analysis with strobe reads. Bioinformatics. 2010; 26(10):1291-8.

Schwartz D C, Li X, Hernandez L I, Ramnarain S P, Huff E J, Wang Y K. Ordered restriction maps of *Saccharomyces cerevisiae* chromosomes constructed by optical mapping. Science. 1993; 262(5130):110-4.

Shendure J, Ji H. Next-generation DNA sequencing. Nat Biotechnol. 2008; 26(10):1135-45.

Shendure J, Mitra R D, Varma C, Church G M. Advanced sequencing technologies: methods and goals. Nat Rev Genet. 2004; 5(5):335-44.

Shendure J, Porreca G J, Reppas N B, Lin X, McCutcheon J P, Rosenbaum A M, et al. Accurate multiplex polony sequencing of an evolved bacterial genome. Science. 2005; 309(5741):1728-32.

Steensel B and Dekker J. Genomics tools for unraveling chromosome architecture. Nature Biotechnology 13 Oct. 2010.

van Berkum, N. L., Lieberman-Aiden, E., Williams, L., Imakaev, M., Gnirke, A., Mirny, L. A., Dekker, J., Lander, E. S., Hi-C: A Method to Study the Three-dimensional Architecture of Genomes. http://www.jove.com/details.stp?id=1869 doi: 10.3791/1869. J Vis Exp. 39 (2010).

Waterston R H, Lander E S, Sulston J E. More on the sequencing of the human genome. Proc Natl Acad Sci USA. 2003; 100(6):3022-4; author reply 5-6. PMCID: PMC152236.

Waterston R H, Lander E S, Sulston J E. On the sequencing of the human genome. Proc Natl Acad Sci USA. 2002; 99(6):3712-6. PMCID: PMC122589.

Waterston R H, Lindblad-Toh K, Birney E, Rogers J, Abril J F, et al. Initial sequencing and comparative analysis of the mouse genome. Nature. 2002; 420(6915):520-62.

Zeng Y, Novak R, Shuga J, Smith M T, Mathies R A. High-performance single cell genetic analysis using microfluidic emulsion generator arrays. Anal Chem. 2010; 82(8):3183-90. PMCID: PMC2859697.

Zhou S, et al. (2007) Validation of rice genome sequence by optical mapping. BMC Genomics 8(1):278.

Zhou S, et al. (2009) A Single Molecule Scaffold for the Maize Genome. PLoS Genet 5(11):e1000711.

Zilberman D, Henikoff S. 2007. Genome-wide analysis of DNA methylation patterns. Development 134(22): 3959-3965.

---

What is claimed is:

1. A method of preparing a sequencing library, comprising:
   (a) contacting a target DNA molecule with a plurality of transposases to insert continuous transposons at a plurality of internal locations in the target DNA molecule to produce a modified target DNA molecule, wherein the continuous transposons each comprise a first flowcell sequence corresponding to a first surface-bound flowcell primer;
   (b) contacting the modified target DNA molecule produced in step (a) with a flowcell to allow hybridization of the first flowcell sequences in the plurality of internally inserted continuous transposons to a plurality of copies of the first surface-bound flowcell primer at co-linear coordinates on the flowcell;
   (c) performing cluster amplification of a plurality of subsequences of the target DNA molecule on the flowcell to produce a plurality of clusters at the co-linear coordinates on the flowcell, wherein each of the plurality of subsequences is adjacent to one of the plurality of internally inserted continuous transposons within the modified target DNA molecule produced in step (a); and
   (d) capturing contiguity information by associating sequences of the plurality of subsequences derived from the plurality of clusters at the co-linear coordinates on the flowcell with positions along an axis of the target DNA molecule.

2. The method of claim 1, further comprising sequencing the plurality of subsequences of the target DNA molecule thereby producing the sequences.

3. The method of claim 1, wherein the plurality of transposons are inserted at a density of about one transposon per every 35 bases to about transposon per every 600 bases.

4. The method of claim 1, further comprising, before step (b), attaching a flowcell-compatible end adaptor to each end of the target DNA molecule wherein each of the end adaptors comprises a flowcell sequence that hybridizes to a surface-bound flowcell primer.

5. The method of claim 4, wherein the flowcell sequence is the first flowcell sequence and the surface-bound flowcell primer is the first surface-bound flowcell primer.

6. The method of claim 4, wherein step (b) comprises stretching the modified target DNA molecule along the flowcell surface.

7. The method of claim 6, wherein the modified target DNA molecule comprising the added end adaptors is stretched under flow or an electric field.

8. The method of claim 1, wherein the contiguity information comprises a positional order of the plurality of sequences obtained from the target DNA molecule.

9. The method of claim 1, wherein the contiguity information comprises a physical distance between a pair of sequences within the target DNA molecule.

10. The method of claim 9, wherein the distance between a pair of co-linear cluster positions on the flowcell surface is directly proportional to the distance between corresponding sequence positions along the axis of the target DNA molecule.

11. The method of claim 1, further comprising performing the method for a plurality of target DNA molecules on the same flowcell.

12. The method of claim 1, wherein insertion of the continuous transposons at internal locations in the target DNA molecule results in a plurality of single-stranded bubble structures at the internal locations in the target DNA molecule.

13. The method of claim 1, wherein the plurality of internal locations in the target DNA molecule are randomly determined.

14. The method of claim 1, wherein prior to step (a) high molecular weight DNA is sheared followed by end repair to produce the target DNA molecule with blunt ends.

15. The method of claim 14, wherein the blunt ends are A-tailed.

16. The method of claim 1, wherein prior to step (a) high molecular weight DNA is sheared followed by end repair to produce the target DNA molecule with blunt ends or digested with a restriction enzyme, and the method further comprises ligating a flowcell-compatible end adaptor to each end of the target DNA molecule.

17. The method of claim 16, wherein each of the end adaptors comprises a flowcell sequence that hybridizes to a surface-bound flowcell primer.

18. The method of claim 17, the flowcell sequence is the first flowcell sequence and the surface-bound flowcell primer is the first surface-bound flowcell primer.

* * * * *

UNITED STATES PATENT AND TRADEMARK OFFICE
CERTIFICATE OF CORRECTION

| | |
|---|---|
| PATENT NO. | : 11,299,730 B2 |
| APPLICATION NO. | : 16/665800 |
| DATED | : April 12, 2022 |
| INVENTOR(S) | : J. Shendure et al. |

It is certified that error appears in the above-identified patent and that said Letters Patent is hereby corrected as shown below:

In the Claims

Column 35 Line 35 change "about transposon" to -- about 1 transposon --

Signed and Sealed this
Eleventh Day of April, 2023

Katherine Kelly Vidal
*Director of the United States Patent and Trademark Office*

SEQUENCE LISTING

```
<160> NUMBER OF SEQ ID NOS: 6

<210> SEQ ID NO 1
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(47)
<223> OTHER INFORMATION: n=5mC
<220> FEATURE:
<221> NAME/KEY: misc_feature
<222> LOCATION: (1)..(47)
<223> OTHER INFORMATION: tn5mC-A1 top sequence

<400> SEQUENCE: 1
gatntanang nntnnntngn gnnatnagag atgtgtataa gagacag          47

<210> SEQ ID NO 2
<211> LENGTH: 16
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(16)
<223> OTHER INFORMATION: tn5mC-A1 bottom sequence

<400> SEQUENCE: 2
ctgtctctta tacaca                                                        16

<210> SEQ ID NO 3
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(47)
<223> OTHER INFORMATION: n=5mC
<220> FEATURE:
<221> NAME/KEY: misc_feature
<222> LOCATION: (1)..(47)
<223> OTHER INFORMATION: tn5mC-P1

<400> SEQUENCE: 3
ctgtctctta tacacatctc tgagngggnt ggnaaggnag anngatn                      47

<210> SEQ ID NO 4
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(38)
<223> OTHER INFORMATION: Read 1: tn5mC-R1 custom sequencing primer

<400> SEQUENCE: 4
gcctccctcg cgccatcaga gatgtgtata agagatag                                38

<210> SEQ ID NO 5
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(38)
<223> OTHER INFORMATION: Index Read: tn5mC-Ix custom sequencing primer

<400> SEQUENCE: 5 ttgttttta tatatatttc tgagcgggct ggcaaggc                                  38

<210> SEQ ID NO 6
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(38)
<223> OTHER INFORMATION: Read 2: tn5mC-R2 custom sequencing primer

<400> SEQUENCE: 6
gccttgccag cccgctcaga aatatatata aaaaacaa                                38
```